US006800637B2

(12) United States Patent
Stack et al.

(10) Patent No.: US 6,800,637 B2
(45) Date of Patent: Oct. 5, 2004

(54) ANTIDEPRESSANT INDOLEALKYL DERIVATIVES OF HETEROCYCLE-FUSED BENZODIOXAN METHYLAMINES

(75) Inventors: Gary Paul Stack, Ambler, PA (US); Michael Byron Webb, Levittown, PA (US); Deborah Ann Evrard, Hamilton Square, NJ (US); Dahul Zhou, East Brunswick, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/659,238

(22) Filed: Sep. 10, 2003

(65) Prior Publication Data

US 2004/0138222 A1 Jul. 15, 2004

Related U.S. Application Data

(60) Provisional application No. 60/410,347, filed on Sep. 12, 2002.

(51) Int. Cl.$^7$ .................... C07D 491/02; C07D 498/02; A61K 31/421; A61K 31/436
(52) U.S. Cl. ........................ 514/291; 514/375; 546/90; 548/218
(58) Field of Search ................................ 514/291, 375; 546/90; 548/218

(56) References Cited

U.S. PATENT DOCUMENTS

| | | | | | |
|---|---|---|---|---|---|
| 5,756,532 | A | * | 5/1998 | Stack et al. | 514/411 |
| 5,869,490 | A | * | 2/1999 | Stack | 514/252.19 |
| 5,962,465 | A | * | 10/1999 | Stack et al. | 514/291 |
| 6,525,075 | B2 | * | 2/2003 | Tran et al. | 514/338 |
| 6,599,915 | B2 | * | 7/2003 | Tran et al. | 514/291 |
| 6,613,913 | B2 | * | 9/2003 | Tran et al. | 548/218 |
| 6,693,197 | B2 | * | 2/2004 | Chan et al. | 546/90 |

FOREIGN PATENT DOCUMENTS

| | | |
|---|---|---|
| EP | 0 464 558 A1 | 1/1992 |
| EP | 0 771 800 A2 | 5/1997 |
| WO | WO 00/35872 A1 | 6/2000 |
| WO | 02/088142 A1 | 11/2002 |

OTHER PUBLICATIONS

Artigas, F., et al., "Pindolol induces a rapid improvement of depressed patients treated with serotonin reuptake inhibitors," *Arch Gen Psychiatry*, Mar. 1994, 51, 248–251.
Blier, P., et al., "Effectiveness of pindolol with selected antidepressant drugs in the treatment of major depression," *J. of Clinical Psychopharmacology*, 1995, 15(3), 217–222.
Bundgaard, H., "Means to enhance penetration; Prodrugs as a means to improve the delivery of peptide drugs," *Advanced Drug Deliver Reviews*, 1992, 8, 1–38.
Cheetham, S.C., et al., "[$^3$H]paroxetine binding in rat frontal cortex strongly correlates with [$^3$H]5–HT uptake: effect of administration of various antidepressant treatments," *Neuropharmacol.*, 1993, 32(8), 737–743.

Hall, M.D., et al., "[$^3$H] 8–hydroxy–2–(Di–n–propylamino)tetralin binding to pre- and postsynaptic 5–hydroxytryptamine sites in various regions of the rat brain," *J. Neurochem.*, 1985, 44, 1685–1696.
Krogsgaard–Larsen, et al. (Eds.), "Design and Application of Prodrugs," *Textbook of Drug Design and Development*, 1991, Chap. 5, 113–191.
Lazareno, S., et al., "Pharmacological characterization of acetylcholine–stimulated [$^3$S]–GTPγS binding mediated by human muscarinic m1–m4 receptors: antagonist studies," *Br. J. Pharmacol.*, 1993, 109, 1120–1127.
Ostrowski, S., "A synthesis of fused pyrimidine mono–n–oxides," *Heterocycles*, 1996, 43(2), p. 389–396.
Perez, V., et al., "Randomised, double–blind, placebo–controlled trial of pindolol in combination with fluoxetine antidepressant treatment," *The Lancet*,m May 31, 1997, 349, 1594–1597.
Tome, M.B., et al., "Serotonergic autoreceptor blocade in the reduction of antidepressant latency: personality variables and response to paroxetine and pindolol," *J. Affect Disord*, 1997, 44, 101–109.
Tome, M.B., et al., "Paroxetine and pindolol: a randomized trial of serotonergic antoreceptor blockade in the reduction of antidepressant latency," *Int. Clin. Psychopharmacol*, 1997, 12, 81–89.
Wilen, S.H., "Tables of Resolving Agents and Optical Resolutions," *Univ. of Notre Dame Press, Notre Dame, IN*, E.L. Eliel (Ed.), 1972, p. 268–298.
Wilen, S.H., et al., "Strategies in optical resolutions," *Tetrahedron*, 1977, 33, 2725–2736.

* cited by examiner

*Primary Examiner*—Fiona T. Powers
(74) *Attorney, Agent, or Firm*—Woodcock Washburn LLP

(57) ABSTRACT

Compounds of the formula:

are useful for the treatment of depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder, social anxiety disorder, generalized anxiety disorder, obesity, eating disorders such as anorexia nervosa, bulimia nervosa, vasomotor flushing, cocaine and alcohol addiction, sexual dysfunction and related illnesses.

76 Claims, No Drawings

ANTIDEPRESSANT INDOLEALKYL DERIVATIVES OF HETEROCYCLE-FUSED BENZODIOXAN METHYLAMINES

CROSS-REFERENCE TO RELATED APPLICATIONS

This application is a Provisional application of U.S. Application Serial No. 60/410,347, filed Sep. 12, 2002, the disclosure of which is incorporated herein by reference in its entirety.

FIELD OF THE INVENTION

This invention relates to antidepressant indolealkyl derivatives of heterocycle-fused benzodioxan methylamines, to processes for preparing them, methods of using them and to pharmaceutical compositions containing them.

BACKGROUND OF THE INVENTION

Major depression is a serious health problem affecting more than 5% of the population, with a lifetime prevalence of 15–20%.

Selective serotonin reuptake inhibitors have produced success in treating depression and related illnesses and have become among the most prescribed drugs. They nonetheless have a slow onset of action, often taking several weeks to produce their full therapeutic effect. Furthermore, they are effective in less than two-thirds of patients.

Serotonin selective reuptake inhibitors (SSRIs) are well known for the treatment of depression and other conditions. SSRIs work by blocking the neuronal reuptake of serotonin, thereby increasing the concentration of serotonin in the synaptic space, and thus increasing the activation of postsynaptic serotonin receptors.

However, although a single dose of an SSRI can inhibit the neuronal serotonin transporter which would be expected to increase synaptic serotonin, long-term treatment is required before clinical improvement is achieved.

It has been suggested that the SSRIs increase the serotonin levels in the vicinity of the serotonergic cell bodies and that the excess serotonin activates somatodendritic autoreceptors, $5HT_{1A}$ receptors, causing a decrease in serotonin release in major forebrain areas. This negative feedback limits the increment of synaptic serotonin that can be induced by antidepressants.

A $5HT_{1A}$ antagonist would limit the negative feedback and should improve the efficacy of the serotonin reuptake mechanism (Perez, V., et al., *The Lancet*, 349:1594–1597 (1997)). Such a combination therapy would be expected to speed up the effect of the serotonin reuptake inhibitor.

Thus, it is highly desirable to provide improved compounds which both inhibit serotonin reuptake and which are antagonists of the $5HT_{1A}$ receptor.

DESCRIPTION OF THE INVENTION

In accordance with this invention, there is provided a group of novel compounds of Formula I:

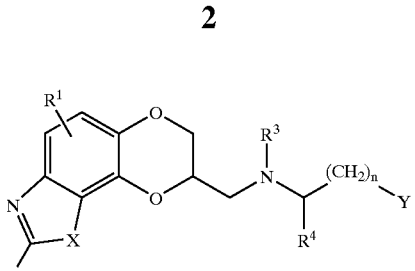

wherein Y is 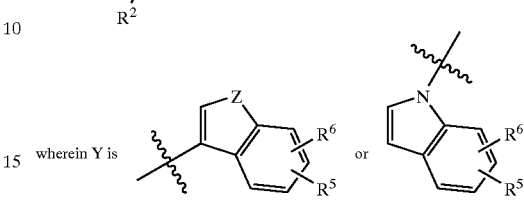

X is O, N=CH, $CR^7$=CH or $CR^7$=N, in which $R^7$ is hydrogen or alkyl of 1 to 6 carbon atoms;

Z is O, S or $NR^8$, in which $R^8$ is hydrogen or alkyl of 1 to 6 carbon atoms;

$R^1$, $R^5$ and $R^6$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyl of 2 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, alkanesulfonyl of 1 to 6 carbon atoms or alkanesulfonamido of 1 to 6 carbon atoms;

$R^2$ is hydrogen, halo, amino, mono- or di-alkylamino in which each alkyl group has 1 to 6 carbon atoms or alkyl of 1 to 6 carbon atoms;

$R^3$ and $R^4$ are, independently, hydrogen or alkyl of 1 to 6 carbon atoms;

n is 1, 2 or 3;

or a pharmaceutically acceptable salt thereof.

$R^1$ is preferably hydrogen, halo, cyano, trifluoromethyl, alkyl of 1 to 6 carbon atoms or alkoxy of 1 to 6 carbon atoms. More preferably, $R^1$ is hydrogen, halo or alkoxy of 1 to 6 carbon atoms. In still more preferred embodiments of the present invention, $R^1$ is hydrogen.

$R^2$ is preferably hydrogen, amino or alkyl of 1 to 6 carbon atoms. More preferably, $R^2$ is hydrogen or alkyl of 1 to 3 carbon atoms.

$R^3$, $R^4$, $R^7$ and $R^8$ are preferably independently selected from hydrogen or alkyl of 1 to 3 carbon atoms. More preferably, $R^3$ is hydrogen or alkyl of 1 to 3 carbon atoms and $R^4$ is hydrogen.

$R^5$ and $R^6$ are preferably independently selected from hydrogen, hydroxy, halo, cyano, carboxamido, alkyl of 1 to 6 carbon atoms, or alkoxy of 1 to 6 carbon atoms. In still more preferred embodiments of the present invention $R^5$ and $R^6$ are preferably independently selected from hydrogen, cyano or halogen.

X is preferably O or $CR^7$=CH. When X is $CR^7$=CH, $R^7$ is preferably hydrogen or alkyl of 1 to 3 carbon atoms.

Z is preferably $NR^8$. When Z is $NR^8$, $R^8$ is preferably hydrogen or alkyl of 1 to 3 carbon atoms.

n is preferably 2 or 3.

In other preferred embodiments of the invention is provided compounds of Formula Ia:

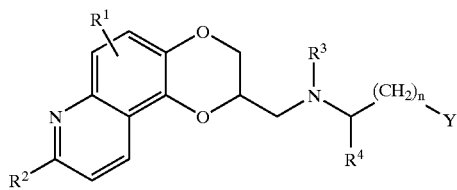

Ia wherein R¹, R², R³, R⁴, R⁵, R⁶, n, and Y are as described above.

In still other preferred embodiments of the invention is provided compounds of Formula Ib:

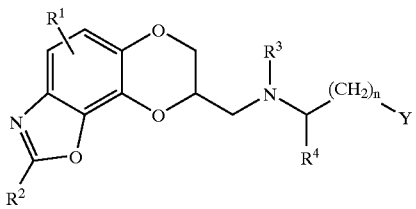

wherein R¹, R², R³, R⁴, R⁵, R⁶, n, and Y are as described above.

This invention relates to both the R and S stereoisomers of the aminomethyl-2,3-dihydro-1,4-dioxino[2,3-f] quinolines, -quinazolines, quinoxalines and aminomethyl-7,8-dihydro[1,4]dioxino[2,3-g][1,3]benzoxazoles as well as to mixtures of the R and S stereoisomers. Throughout this application, the name of the product of this invention, where the absolute configuration of the compounds of the invention is not indicated, is intended to embrace the individual R and S enantiomers as well as mixtures of the two. In some embodiments of the present invention the S enantiomer is preferred. Certain of the compounds of this invention (i.e., R⁴ is alkyl) contain two stereogenic centers and thus may exist as diastereomers. This invention relates to both diastereomers, as well as to mixtures of diastereomers.

Where a stereoisomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. "Substantially free," as used herein, means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

"Alkyl," as used herein, refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

"Alkanamido," as used herein, refers to the group R—C(=O)—NH— where R is an alkyl group of 1 to 5 carbon atoms.

"Alkanoyl," as used herein, refers to the group R—C(=O)— where R is an alkyl group of 1 to 5 carbon atoms.

"Alkanoyloxy," as used herein, refers to the group R—C(=O)—O— where R is an alkyl group of 1 to 5 carbon atoms.

"Alkanesulfonamido," as used herein, refers to the group R—S(O)₂—NH— where R is an alkyl group of 1 to 6 carbon atoms.

"Alkanesulfonyl," as used herein, refers to the group R—S(O)₂— where R is an alkyl group of 1 to 6 carbon atoms.

"Alkoxy," as used herein, refers to the group R—O— where R is an alkyl group of 1 to 6 carbon atoms.

"Carboxamido," as used herein, refers to the group NH₂—C(=O)—.

"Carboalkoxy," as used herein, refers to the group R—O—C(=O)— where R is an alkyl group of 1 to 5 carbon atoms.

"Halogen" (or "halo"), as used herein, refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific examples of compounds of Formula I are:

N-[2-(5Methoxy-1H-indol-3-yl)-ethyl]-N-(8-methyl-2,3-dihydro-[1,4]dioxino[2,3-f]quinolin-2-ylmethyl)-amine;
N-[2-(5-Chloro-1H-indol-3-yl)ethyl]-N-(8-methyl-2,3-dihydro-[1,4]dioxino[2,3-f]quinolin-2-ylmethyl)amine;
N-[3-(5-Fluoro-1H-indol-3-yl)propyl]-N-(8-methyl-2,3-dihydro-[1,4]dioxino[2,3-f]quinolin-2-ylmethyl)amine;
N-[2-(5-Fluoro-1H-indol-3-yl)ethyl]-N-(8-methyl-2,3-dihydro-[1,4]dioxino[2,3-f]quinolin-2-ylmethyl)amine;
N-[3-(5-Fluoro-1H-indol-3-yl)propyl]-N-(8-ethyl-2,3-dihydro-[1,4]dioxino[2,3-f]quinolin-2-ylmethyl)amine;
N-[3-(1H-indol-3-yl)propyl]-N-(8-methyl-2,3-dihydro-[1,4]dioxino[2,3-f]quinolin-2-ylmethyl)amine;
N-[3-(5-Fluoro-1H-indol-3-yl)propyl]-N-methyl-N-(8-methyl-2,3-dihydro-[1,4]dioxino[2,3-f]quinolin-2-ylmethyl)amine;
N-[3-(7-Fluoro-1H-indol-3-yl)propyl]-N-(8-methyl-2,3-dihydro-[1,4]dioxino[2,3-f]quinolin-2-ylmethyl)amine;
N-[4-(1H-indol-3-yl)butyl]-N-(8-methyl-2,3-dihydro-[1,4]dioxino[2,3-f]quinolin-2-ylmethyl)amine;
N-[4-(5-Fluoro-1H-indol-3-yl)butyl]-N-(8-methyl-2,3-dihydro-[1,4]dioxino[2,3-f]quinolin-2-ylmethyl)amine;
N-[4-(5-Fluoro-1H-indol-3-yl)-N-(8-methyl-2,3-dihydro-[1,4]dioxino[2,3-f]quinolin-2-ylmethyl)butan-2-amine;
N-[3-(5-Fluoro-1-methyl-1H-indol-3-yl)propyl]-N-(8-methyl-2,3-dihydro-[1,4]dioxino[2,3-f]quinolin-2-ylmethyl)amine;
N-[3-(5,7-Difluoro-1H-indol-3-yl)propyl]-N-(8-methyl-2,3-dihydro-[1,4]dioxino[2,3-f]quinolin-2-ylmethyl)amine;
N-(2,3-Dihydro-[1,4]dioxino[2,3-f]quinolin-2-ylmethyl)-N-[3-(5-fluoro-1H-indol-3-yl)propyl]amine;
N-(2,3-Dihydro-[1,4]dioxino[2,3-f]quinolin-2-ylmethyl)-N-[3-(5-fluoro-1H-indol-3-yl)propyl]-N-methylamine;

N-[3-(5,7-Difluoro-1H-indol-3-yl)propyl]-N-methyl-N-(8-methyl-2,3-dihydro-[1,4]dioxino[2,3-f]quinolin-2-ylmethyl)amine;

N-[2-(1-Benzofuran-3-yl)ethyl]-N-(8-methyl-2,3-dihydro-[1,4]dioxino[2,3-f]quinolin-2-ylmethyl)amine;

N-[3-(1-Benzofuran-3-yl)propyl]-N-(8-methyl-2,3-dihydro-[1,4]dioxino[2,3-f]quinolin-2-ylmethyl)amine;

N-[3-(7-Methoxy-1-benzofuran-3-yl)propyl]-N-(8-methyl-2,3-dihydro-[1,4]dioxino[2,3-f]quinolin-2-ylmethyl)amine;

N-[3-(1-Benzothien-3-yl)propyl]-N-(8-methyl-2,3-dihydro-[1,4]dioxino[2,3-f]quinolin-2-ylmethyl)amine;

N-[2-(1-Benzothien-3-yl)ethyl]-N-(8-methyl-2,3-dihydro-[1,4]dioxino[2,3-f]quinolin-2-ylmethyl)amine;

N-[3-(1-Benzothien-3-yl)propyl]-N-methyl-N-(8-methyl-2,3-dihydro-[1,4]dioxino[2,3-f]quinolin-2-ylmethyl)amine;

N-[3-(5-Fluoro-1H-indol-3-yl)propyl]-N-(2-methyl-7,8-dihydro-[1,4]dioxino[2,3-g][1,3]benzoxazol-8-ylmethyl)amine;

N-[3-(5-Fluoro-1H-indol-3-yl)propyl]-N-methyl-N-(2-methyl-7,8-dihydro-[1,4]dioxino[2,3-g][1,3]benzoxazol-8-ylmethyl)amine;

N-Ethyl-N-[3-(5-Fluoro-1H-indol-3-yl)propyl]-N-(8-methyl-2,3-dihydro-[1,4]dioxino[2,3-f]quinolin-2-ylmethyl)amine;

N-[3-(5,7-Difluoro-1-methyl-1H-indol-3-yl)propyl]-N-(8-methyl-2,3-dihydro-[1,4]dioxino[2,3-f]quinolin-2-ylmethyl)amine;

N-[3-(5,7-Difluoro-1-methyl-1H-indol-3-yl)propyl]-N-methyl-N-(8-methyl-2,3-dihydro-[1,4]dioxino[2,3-f]quinolin-2-ylmethyl)amine;

N-[4-(1-Benzofuran-3-yl)butyl]-N-(8-methyl-2,3-dihydro-[1,4]dioxino[2,3-f]quinolin-2-ylmethyl)amine;

3-{3-[(8-Methyl-2,3-dihydro-[1,4]dioxino[2,3-f]quinolin-2-ylmethyl)-amino]-propyl}-1H-indole-5-carbonitrile;

3-{3-[(2-Methyl-7,8-dihydro-[1,4]dioxino[2,3-g][1,3]benzoxazol-8-ylmethyl)amino]-propyl}-1H-indole-5-carbonitrile;

3-{3-[Methyl-(2-methyl-7,8-dihydro-[1,4]dioxino[2,3-g][1,3]benzoxazol-8-ylmethyl)-amino]-propyl}-1H-indole-5-carbonitrile;

3-{3-[Methyl-(8-methyl-2,3-dihydro-[1,4]dioxino[2,3-f]quinolin-2-ylmethyl)-amino]-propyl}-1H-indole-5-carbonitrile;

[3-(6-Fluoro-indol-1-yl)-propyl]-(8-methyl-2,3-dihydro-[1,4]dioxino[2,3-f]quinolin-2-ylmethyl)-amine;

[3-(6-Fluoro-indol-1-yl)-propyl]-methyl-(8-methyl-2,3-dihydro-[1,4]dioxino[2,3-f]quinolin-2-ylmethyl)-amine;

[4-(5-Fluoro-1-methyl-1H-indol-3-yl)-butyl]-(8-methyl-2,3-dihydro-[1,4]dioxino[2,3-f]quinolin-2-ylmethyl)-amine;

Ethyl-[3-(5-fluoro-1H-indol-3-yl)-propyl]-(2-methyl-7,8-dihydro-[1,4]dioxino[2,3-g][1,3]benzoxazol-8-ylmethyl)-amine;

1-Methyl-3-{3-[(8-methyl-2,3-dihydro-[1,4]dioxino[2,3-f]quinolin-2-ylmethyl)-amino]-propyl}-1H-indole-5-carbonitrile;

[4-(6-Fluoro-indol-1-yl)-butyl]-(8-methyl-2,3-dihydro-[1,4]dioxino[2,3-f]quinolin-2-ylmethyl)-amine;

3-{4-[(8-Methyl-2,3-dihydro-[1,4]dioxino[2,3-f]quinolin-2-ylmethyl)-amino]-butyl}-1H-indole-5-carbonitrile;

1-Methyl-3-{3-[methyl-(8-methyl-2,3-dihydro-[1,4]dioxino[2,3-f]quinolin-2-ylmethyl)-amino]-propyl}-1H-indole-5-carbonitrile;

3-{4-[Methyl-(8-methyl-2,3-dihydro-[1,4]dioxino[2,3-f]quinolin-2-ylmethyl)-amino]-butyl}-1H-indole-5-carbonitrile;

[3-(5-Fluoro-1-methyl-1H-indol-3-yl)-propyl]-methyl-(8-methyl-2,3-dihydro-[1,4]dioxino[2,3-f]quinolin-2-ylmethyl)-amine;

[4-(5-Fluoro-1H-indol-3-yl)-butyl]-methyl-(8-methyl-2,3-dihydro-[1,4]dioxino[2,3-f]quinolin-2-ylmethyl)-amine;

[4-(5-Fluoro-1-methyl-1H-indol-3-yl)-butyl]-methyl-(8-methyl-2,3-dihydro-[1,4]dioxino[2,3-f]quinolin-2-ylmethyl)-amine;

[3-(5-Fluoro-1H-indol-3-yl)-propyl]-(8-methyl-2,3-dihydro-[1,4]dioxino[2,3-f]quinolin-2-ylmethyl)-propyl-amine;

[3-(4-Fluoro-indol-1-yl)-propyl]-(8-methyl-2,3-dihydro-[1,4]dioxino[2,3-f]quinolin-2-ylmethyl)-amine;

[4-(6-Fluoro-indol-1-yl)-butyl]-methyl-(8-methyl-2,3-dihydro-[1,4]dioxino[2,3-f]quinolin-2-ylmethyl)-amine;

[3-(4-Fluoro-indol-1-yl)-propyl]-methyl-(8-methyl-2,3-dihydro-[1,4]dioxino[2,3-f]quinolin-2-ylmethyl)-amine;

N-[4[(5-Chloro-1-benzothien-3-yl)butyl]-N-{[(2S)-8-methyl-2,3-dihydro[1,4]dioxino[2,3-f]quinolin-2-yl]methyl};

N-[3-(5-Chloro-1-benzothien-3-yl)propyl]-N-{[(2S)-8-methyl-2,3-dihydro[1,4]dioxino[2,3-f]quinolin-2-yl]methyl}amine;

N-[3-(5-Fluoro-1-benzothien-3-yl)propyl]-N-{[(2S)-8-methyl-2,3-dihydro[1,4]dioxino[2,3-f]quinolin-2-yl]methyl}amine; and N-[4-(1-Benzofuran-3-yl)butyl]-N-ethyl-N-{[(2S)-8-methyl-2,3-dihydro[1,4]dioxino[2,3-f]quinolin-2-yl]methyl}amine.

Compounds of the present invention are prepared in accordance with the following general description and specific examples. Variables used are as defined for Formula I, unless otherwise noted. The 2,3-dihydro-1,4-dioxino[2,3-f]quinolin-2-ylmethylamines in which $R^2$ is H are prepared as illustrated in Scheme 1 below. Specifically, the appropriately substituted nitroguaiacol (1) is alkylated with allyl bromide in the presence of a suitable base such as sodium hydride and then demethylated by a reagent such as sodium hydroxide. The resulting 4-nitro-2-allyloxyphenol (3) is then alkylated with glycidyl tosylate or an epihalohydrin in the presence of a base such as sodium hydride and heated in a high boiling solvent such as mesitylene or xylene to effect both rearrangement of the allyl group and cyclization of the dioxan ring. The resulting primary alcohol (5) is converted to the tosylate by reaction with p-toluenesulfonyl chloride in the presence of a tertiary amine or pyridine, or alternatively to a halide by reaction with carbon tetrabromide or carbon tetrachloride in combination with triphenylphosphine. The allyl side chain is then isomerized by treatment with catalytic bis-acetonitrile palladium (II) chloride in refluxing methylene chloride or benzene. Allylic oxidation of 6 with selenium dioxide in refluxing dioxane/water gives the o-nitrocinnamaldehyde, which upon reduction with iron in acetic acid cyclizes to the 2,3-dihydro-1,4-dioxino[2,3-f]quinoline-2-methyltosylate (7) or halide. Replacement of the tosylate or halide with the appropriately substituted indolealkylamine in some high boiling solvent such as dimethyl sulfoxide gives the title compounds of the invention.

Scheme 1

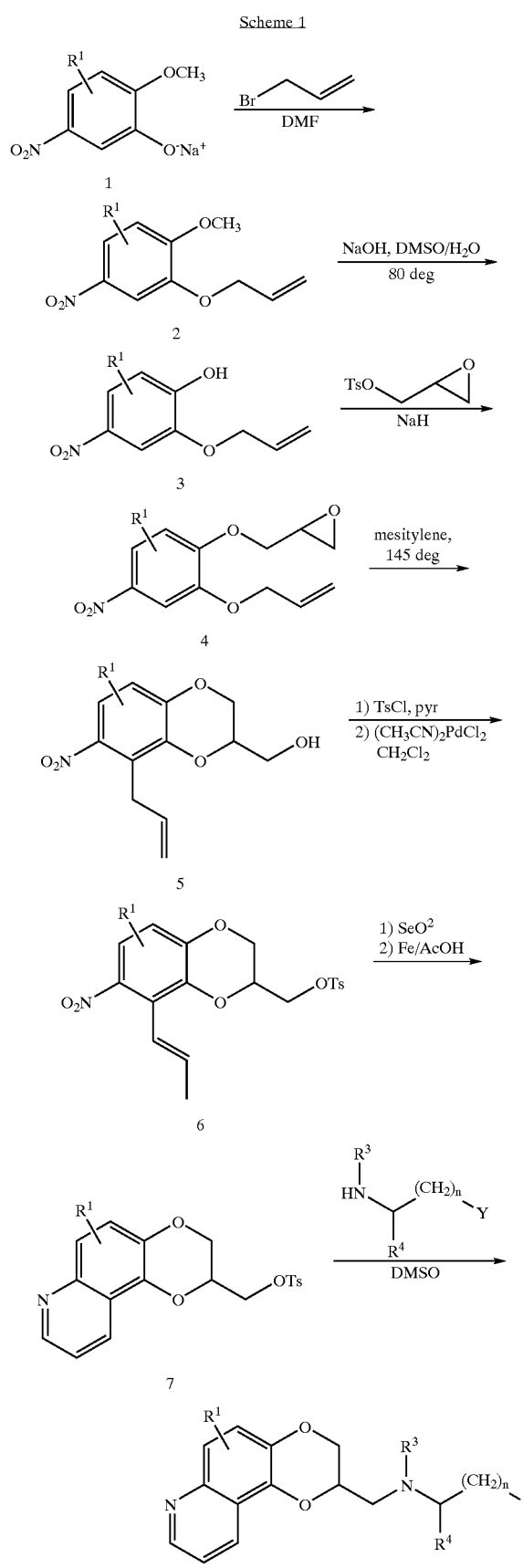

The 2,3-dihydro-1,4-dioxino[2,3-f]quinolin-2-ylmethylamines of the invention in which $R^2$ is alkyl may be prepared from the nitro olefin described above in the following manner (Scheme 2). The rearranged olefin (6) is treated sequentially with ozone and a tertiary amine or with osmium tetroxide and sodium periodate to give the o-nitrobenzaldehyde (8). Condensation with the appropriate triphenylphosphorylidene ketone under Wittig conditions gives the o-nitrocinnamyl ketone (9), which upon reduction by iron in acetic acid, cyclizes to the corresponding 2,3-dihydro-1,4-dioxino[2,3-f]quinoline-2-methyltosylate (10). Replacement of the tosylate with the appropriately substituted indolealkylamine as above gives the title compounds of the invention. Substitution of trimethyl phosphonoacetate for the triphenylphosphorylidene ketone in the Wittig procedure above, followed by reduction of the nitro group with tin (II) chloride and cyclization in acid gives the compounds of the invention in which $R^2$ is hydroxy. Treatment of the hydroxy derivative with an inorganic acid chloride such as phosphoryl chloride or bromide gives the compounds of the invention in which $R^2$ is halo. Substitution of diethyl cyanomethylphosphonate for the triphenylphosphorylidene ketone in the Wittig procedure above, followed by reduction of the nitro group with tin (II) chloride and cyclization in acid gives the compounds of the invention in which $R^2$ is amino.

Scheme 2

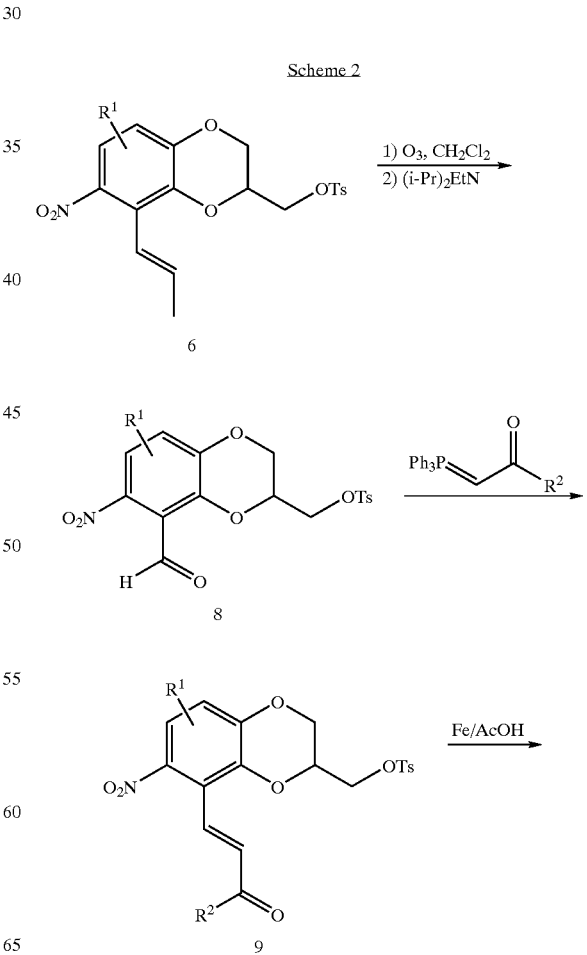

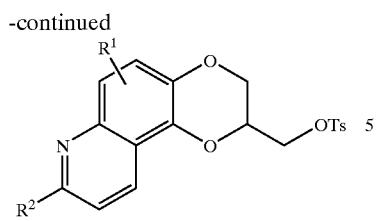

10

Compounds of the invention in which $R^1$ is attached to position 6 of the 2,3-dihydro-1,4-dioxino[2,3-f]quinolin-2-ylmethylamines may be alternatively prepared by a variation of the Skraup quinoline synthesis according to Scheme 3 below. The appropriately substituted benzodioxan methyltosylate (11) is nitrated under standard conditions with nitric acid in a solvent such as dichloroethane and the resulting nitro compound (12) reduced by treatment with hydrogen in the presence of a catalyst such as platinum on sulfide carbon. Treatment of the resulting aniline (13) with acrolein in the presence of hydrogen chloride and an oxidant such as p-chloranil or naphthoquinone gives the corresponding 2,3-dihydro-1,4-dioxino[2,3-f]quinoline (14). Replacement of the tosylate with the appropriately substituted indolealkylamine as above gives the title compounds of the invention.

Scheme 3

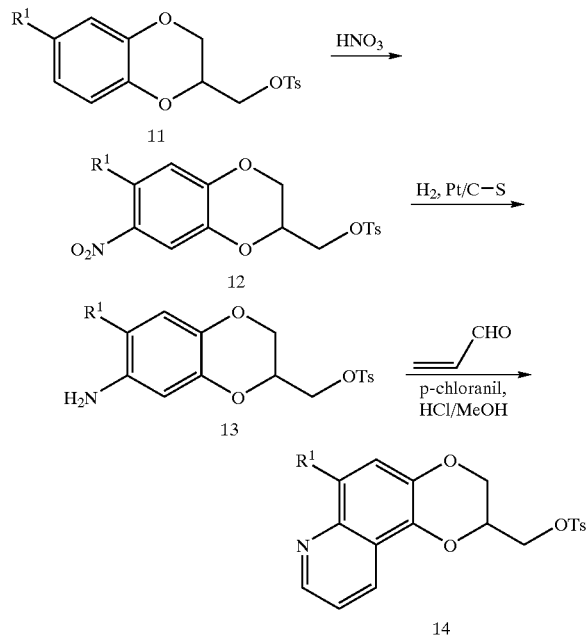

The 2,3-dihydro-1,4-dioxino[2,3-f]quinazolin-2-ylmethylamines of the invention are prepared as illustrated below (Scheme 4). The o-nitrobenzaldehyde (8) described above is converted to the oxime (15) by treatment with hydroxylamine hydrochloride in the presence of a suitable base such as sodium acetate and the nitro group reduced to the amine by hydrogenation over palladium on carbon. Cyclization to the quinazoline N-oxide is effected by treatment at reflux with the appropriate ortho ester according to the method of Ostrowski (Heterocycles, vol. 43, No. 2, p. 389, 1996). The quinazoline N-oxide may be reduced to the quinazoline (16) by a suitable reducing agent such as hydrogen over Raney-nickel. Alternatively, an extended period of reflux in the ortho ester gives the reduced quinazoline directly via a disproportionation reaction and the 2,3-dihydro-1,4-dioxino[2,3-f]quinazoline-2-methyltosylate or halide may be isolated by column chromatography. Replacement of the tosylate or halide with the appropriately substituted indolealkylamine in some high boiling solvent such as dimethyl sulfoxide gives the title compounds of the invention.

Scheme 4

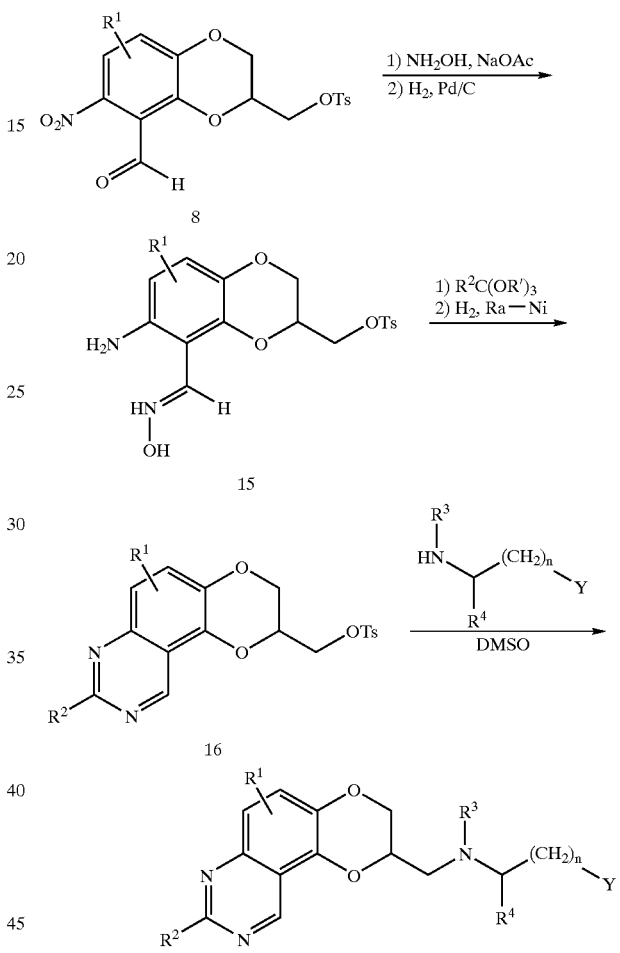

The 2,3-dihydro-1,4-dioxino[2,3-f]quinazolin-2-ylmethylamines of the invention may be alternatively prepared from the rearranged olefin described above by the method outlined in Scheme 5 below. The nitro olefin (6) is first reduced to the aniline by treatment with a suitable reducing agent such as stannous chloride dihydrate in refluxing ethyl acetate and the resulting amine acylated with the appropriate acyl halide or anhydride. The olefin (17) is then converted to the aldehyde (18) by cleavage with catalytic osmium tetroxide in the presence of excess sodium periodate. Cyclization directly to the 2,3-dihydro-1,4-dioxino[2,3-f]quinazoline-2-methyltosylate (16) or halide is effected by treatment of the amido aldehyde (18) with ammonia and replacement of the tosylate or halide with the appropriately substituted indolealkylamine in some high boiling solvent such as dimethyl sulfoxide as described above gives the title compounds of the invention.

Scheme 5

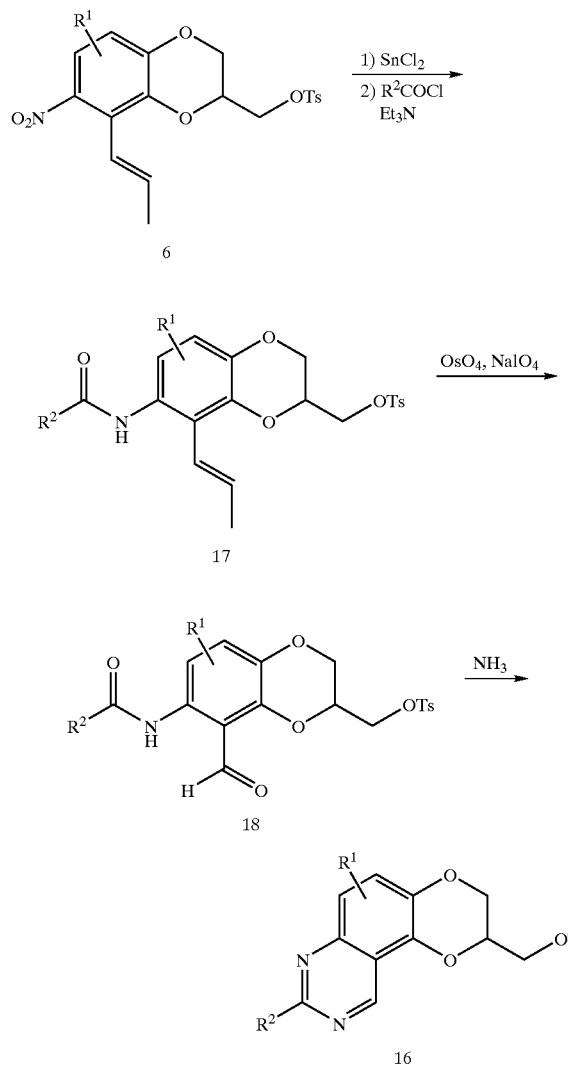

Scheme 6

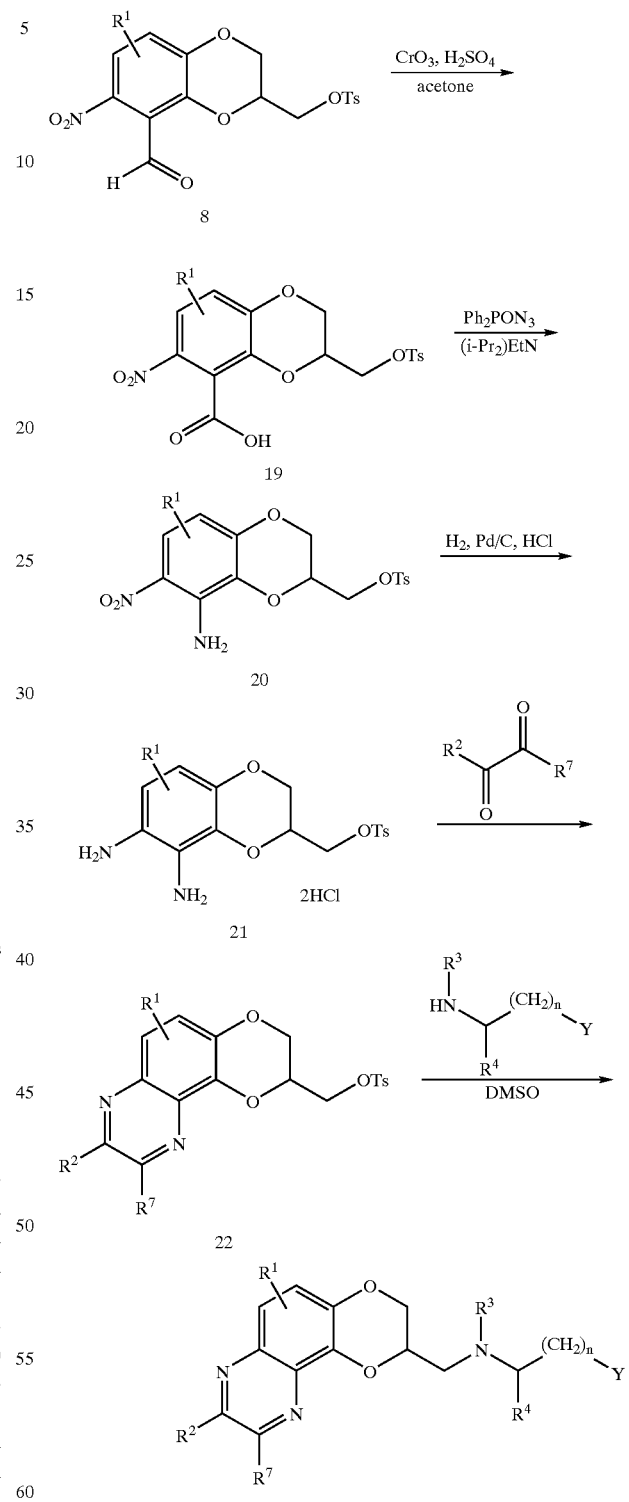

The 2,3-dihydro-1,4-dioxino[2,3-f]quinoxalin-2-ylmethylamines of the invention are prepared as illustrated in Scheme 6 below. The o-nitrobenzaldehyde (8) described above is oxidized to the o-nitrobenzoic acid (19) by a suitable oxidant such as chromium trioxide (Jones' oxidation) or sodium chlorite and the acid converted to the o-nitroaniline (20) with diphenylphosphoryl azide (DPPA) in the presence of a tertiary base such as diisopropylethylamine. Reduction of the resulting nitroaniline to the diamine (21) with hydrogen and palladium on carbon and cyclization by treatment with the appropriate dicarbonyl compound (for example, glyoxal, 2,3-butanedione, 3,4-hexanedione) gives the 2,3-dihydro-1,4-dioxino[2,3-f]quinoxaline-2-methyltosylate (22) or halide. Replacement of the tosylate or halide with the appropriately substituted indolealkylamine in some high boiling solvent such as dimethyl sulfoxide gives the title compounds of the invention.

The o-nitrobenzaldehyde (8) used in the chemistry described above may be alternatively prepared as shown in scheme 7 below. The appropriate mono-allylated catechol (23) is elaborated with glycidyl tosylate as described above and rearranged in refluxing mesitylene. Cyclization to the benzodioxan methanol (25) is effected by treatment with sodium bicarbonate in ethanol and the alcohol is converted to the tosylate (26) or halide as described above. After rearrangement of the double bond by treatment with catalytic bis-acetonitrile palladium (II) chloride in refluxing methylene chloride and cleavage with ozone or osmium tetroxide/sodium periodate as described above, the resulting aldehyde (27) is regioselectively nitrated with a combination of nitric acid and tin (IV) chloride.

meta-chloroperoxybenzoic acid in a Baeyer-Villager reaction and cyclization to the 7,8-dihydro[1,4]dioxino[2,3-g][1,3]benzoxazole (29) is effected by treatment at reflux with an appropriate dehydrating agent such as an ortho ester or an acid catalyst such as p-toluenesulfonic acid. Replacement of the tosylate or halide with the appropriately substituted indolealkylamine in some high boiling solvent such as dimethyl sulfoxide gives the title compounds of the invention.

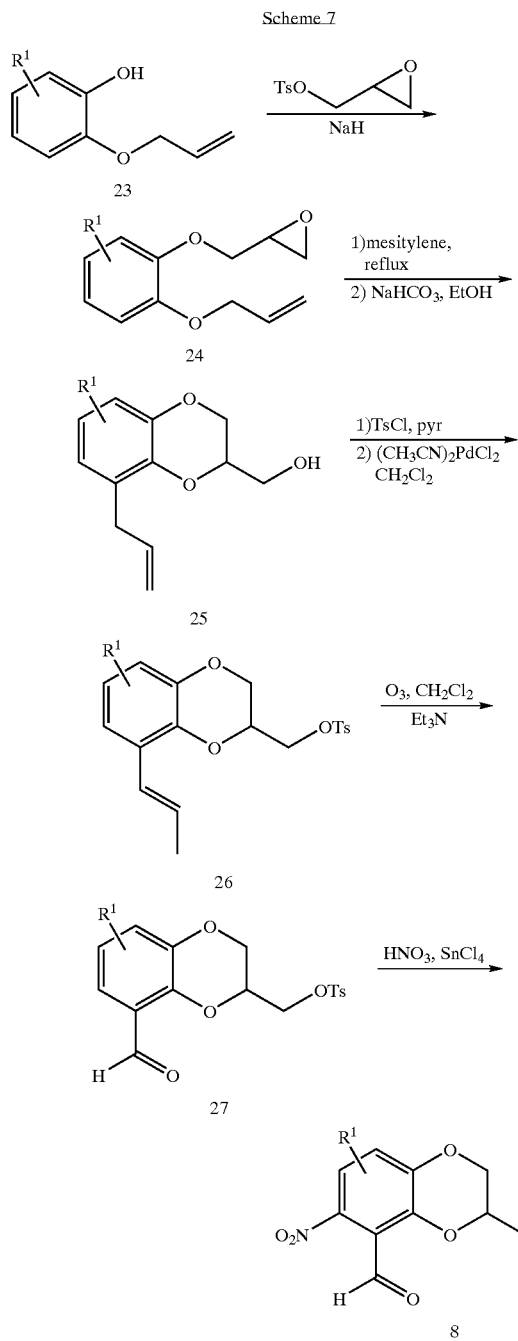

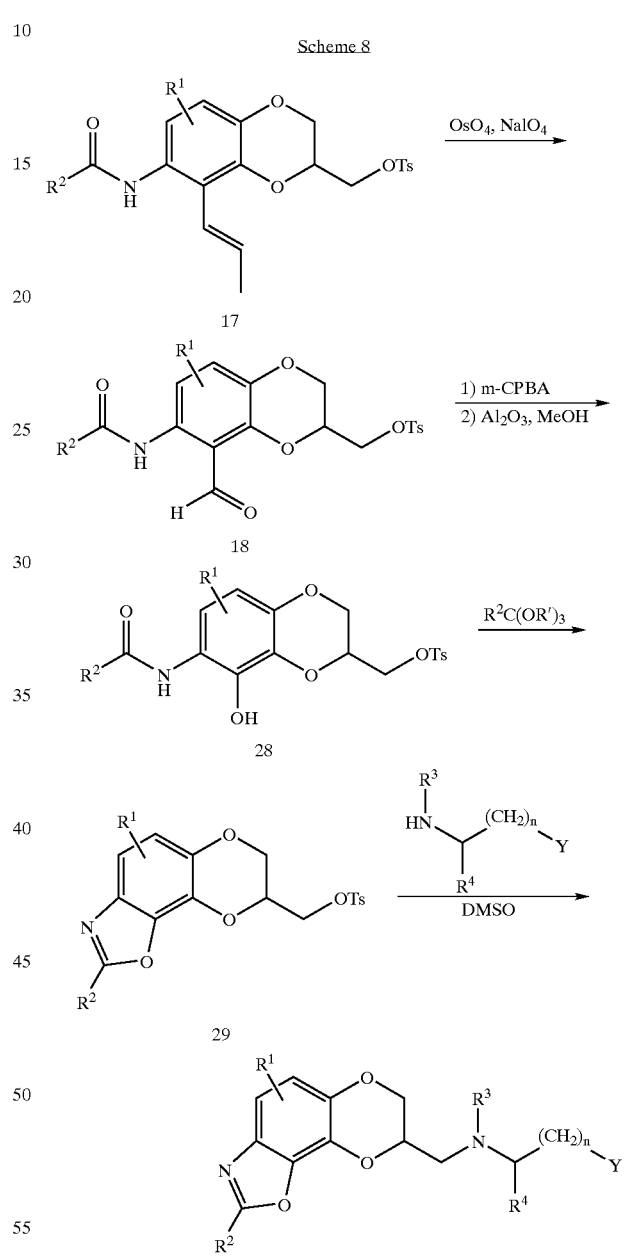

The 7,8-dihydro[1,4]dioxino[2,3-g][1,3]benzoxazol-8-ylmethylamines of the invention are prepared as illustrated in Scheme 8 below. The amido olefin (17) described in Scheme 5 is cleaved to the corresponding o-amidobenzaldehyde (18) by treatment with catalytic osmium tetroxide in the presence of sodium periodate. The aldehyde is converted to the phenol (28) by treatment with Alternatively (Scheme 9), the nitro olefin (6) may be reduced with tin (II) chloride as described in Scheme 5 above and protected with a suitable protecting group such as carbobenzoxy (Cbz) before the olefin is cleaved to the aldehyde (31) by treatment with osmium tetroxide/sodium periodate and the aldehyde converted to a phenol (32) by the Baeyer-Villager procedure. Deprotection by treatment with hydrogen over palladium on carbon gives the o-aminophenol, (33) which is cyclized to the 7,8-dihydro[1,4]dioxino[2,3-g][1,3]benzoxazole (29) by treatment with the appropriate ortho ester, carboxylic acid or anhydride. Treatment of the o-aminophenol with cyanogen bromide or chloride or a suitably substituted carbarmoyl chloride leads to compounds of the invention in which $R^2$ is amino. Treatment of the o-aminophenol with carbonyl diimidazole gives the oxazolone which leads to compounds of the invention in which $R^2$ is halo via treatment with an inorganic anhydride such as phosphoryl chloride or bromide. Replacement of the tosylate with the appropriately substituted indolealkylamine as above gives the title compounds of the invention.

Scheme 9

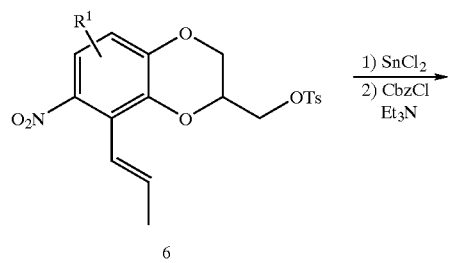

6

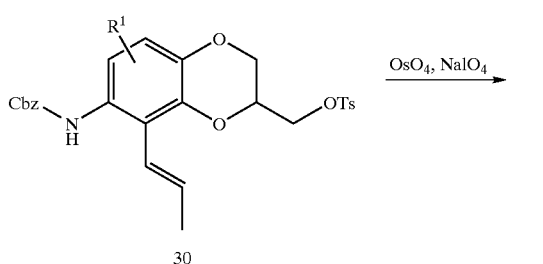

30

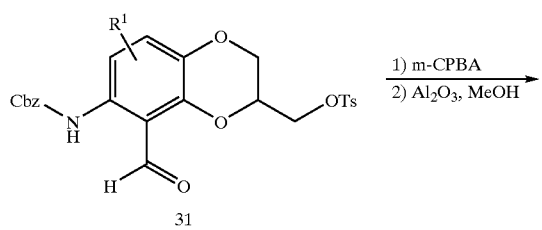

31

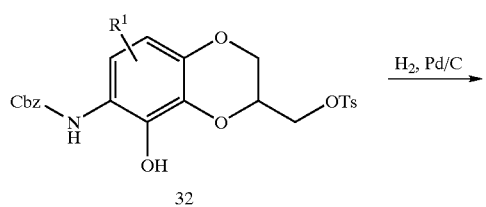

32

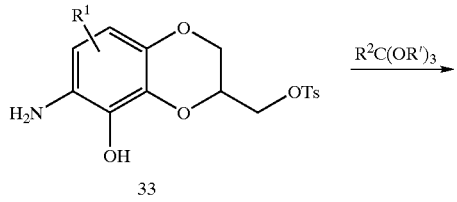

33

-continued

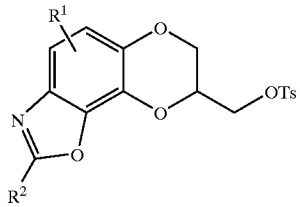

29

Compounds of the invention in which $R^1$ is hydrogen and $R^2$ is alkyl are most conveniently prepared according to scheme 10 below. The appropriate 2',3',4'-trihydroxyacylphenone (34) is regioselectively alkylated with glycidyl tosylate or an epihalohydrin in the presence of a base such as sodium carbonate to give the corresponding 7-acyl-8-hydroxybenzodioxan-2-methanol (35). Following conversion of the ketone to the oxime (36) by reaction with hydroxylamine hydrochloride and sodium acetate, cyclization to the oxazole (37) is effected by treatment with phosphoryl chloride in the appropriate dimethylalkanoic acid amide. The resulting 7,8-dihydro-1,6,9-trioxa-3-aza-cyclopenta[a]naphthalene-8-methanol is converted to the tosylate (38) by treatment with p-toluenesulfonyl chloride in pyridine and combined with the appropriate indolealkylamines as described to give the title compounds of the invention.

Scheme 10

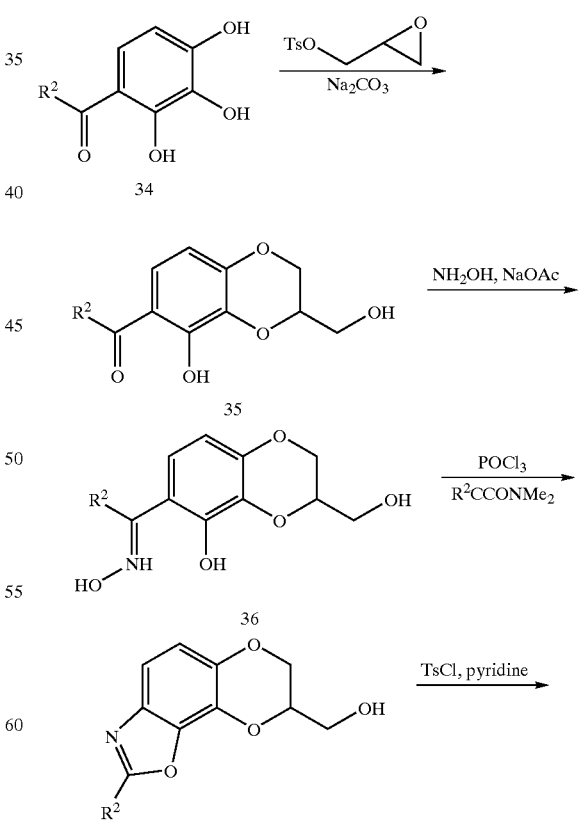

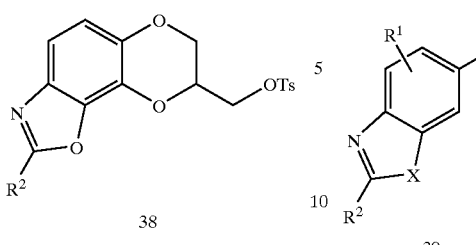

38

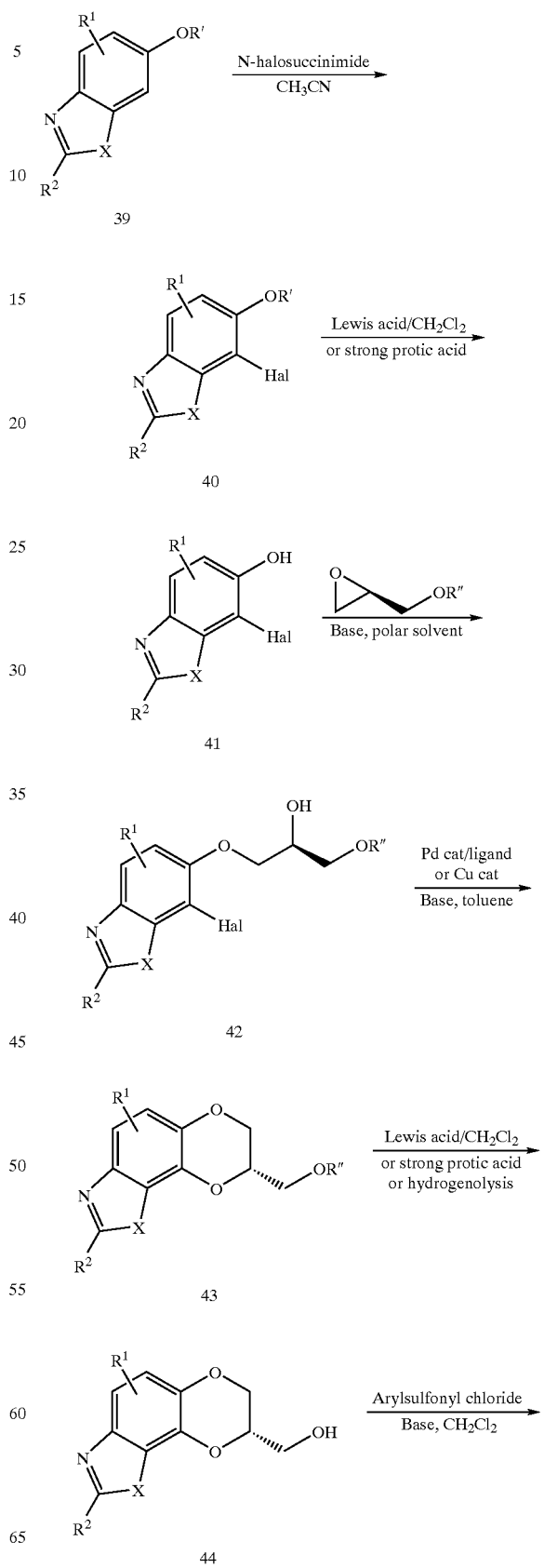

The compounds of the invention may be resolved into their enantiomers by conventional methods or, preferably, the individual enantiomers may be prepared directly by substitution of (2R)-(−)glycidyl 3-nitrobenzene-sulfonate or tosylate (for the S benzodioxan methanamine) or (2S)-(+)-glycidyl 3-nitrobenzene-sulfonate or tosylate (for the R enantiomer) in place of epihalohydrin or racemic glycidyl tosylate in the procedures above.

In yet another method, compounds of the present invention may be prepared in accordance with Scheme 11. The synthesis of compound I is comprised of steps that begin with halogenation of 39 where R' is alkyl of 1–6 carbon atoms, with reagents such as N-halosuccinimide in acetonitrile to give 40 (where Hal is halogen such as Br, Cl or I). Deprotecting 40 with Lewis acids such as boron tribromide, boron trichloride, aluminum trichloride, ferric chloride, or trimethylsilyl iodide in a suitable solvent such as methylene chloride, or with strong protic acids such as HBr and HCl gives the salt 41. Free base 41 may be obtained by neutralization with an Amberlyst A-21 resin slurry in polar solvents such as ethanol or methanol.

Alkylation of 41, either as the free base or as the salt, with benzyl or substituted benzyl protected glycidyl ethers

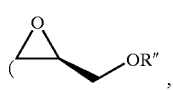, where R″ is benzyl, substituted benzyl such as 4-bromobenzyl, 3,4-dimethoxybenzyl, 2- or 4-nitrobenzyl, or 4-methoxybenzyl) in suitable polar solvents such as DMSO, DMF, or DMA in the presence of bases such as sodium carbonate, potassium carbonate, or triethylamine gives 42. 42 was then cyclized using palladium catalysts such as tris(dibenzylideneacetone)dipalladium, tetrakis(triphenylphosphine)palladium, or palladium acetate with ligands from the group consisting of (±) BINAP and separate enantiomers thereof, (±) Tol-BINAP and separate enantiomers thereof; 1-1'-bis(diphenylphosphino)ferrocene, 1,3-bis(diphenylphosphino)propane, and 1,2 bis(diphenylphosphino)ethane in the presence of bases such as NaH, LiH, KH, potassium carbonate, sodium carbonate, titanium carbonate, cesium carbonate, potassium t-butoxide or potassium phosphate tribasic in suitable solvent such as toluene, or alternatively, with copper catalyst such as copper iodide in the presence of bases such NaH, LiH, KH in a suitable solvent such as toluene to afford 43.

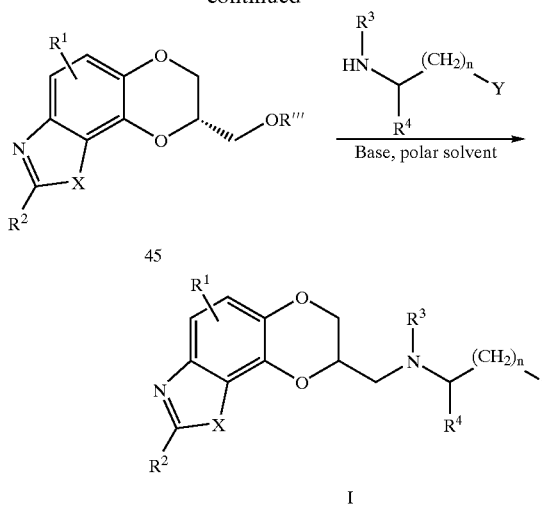

Deprotection of quinoline 43 with Lewis acids such as boron tribromide, boron trichloride, aluminum trichloride, ferric chloride, trimethylsilyl iodide in a suitable solvent such as methylene chloride, or with strong protic acids such as HBr and HCl or under reductive cleavage conditions using Pd catalyst and hydrogen transfer reagents such as hydrogen, cyclohexene, methyl cyclohexene, or ammonium formate gives the heterocycle-fused benzodioxanmethanol 44. The hydroxyl moiety of 44 can be activated with an aryl- or alkylsulfonyl chloride such as p-toluenesulfonyl chloride, methanesulfonyl chloride, 2-, 3- or 4-nitrobenzenesulfonyl chloride, or 2- or 4-bromobenzenesulfonyl chloride in the presence of bases such as triethylamine or pyridine in suitable solvents such as methylene chloride, THF, or toluene to afford 45 where R''' is a sulfonate such as p-toluenesulfonate, methanesulfonate, 2-, 3-, or 4-nitrobenzenesulfonate, or 2- or 4-bromobenzenesulfonate. The final coupling of 45 with indolealkylamines appropriate to the invention, in the presence of bases such as Hünig's base (diisopropyl ethylamine), potassium carbonate, or sodium carbonate in polar solvents such as THF, dioxane, DMSO, DMF, or DMA affords the compounds of Formula I.

The compounds of the invention may alternatively be prepared from the heterocycle-fused benzodioxan methyltosylate (45) by the method outlined below in Scheme 11. The tosylate is heated with sodium azide in an appropriate solvent such as DMF to give the azide 46, which is then reduced to the primary amine (47) by a suitable reducing agent such as hydrogen over palladium on carbon, sodium borohydride in isopropanol or triphenylphosphine. The primary amine 47 may either be reductively alkylated by treatment with a suitably substituted aldehyde or ketone in the presence of a reducing agent such as sodium cyanoborohydride or alkylated with a suitably substituted indolealkyl halide, alkylsulfonate or arylsulfonate in the presence of a base such as triethylamine or Hunig's base to give the compounds of the invention in which $R^3$ is hydrogen. The secondary amines thus derived may be further alkylated if desired by treatment with the appropriate alkyl halide in the presence of a tertiary base or alkanal in the presence of a reducing agent such as sodium cyanoborohydride to give the compunds of the invention in which $R^3$ is alkyl.

Scheme 12

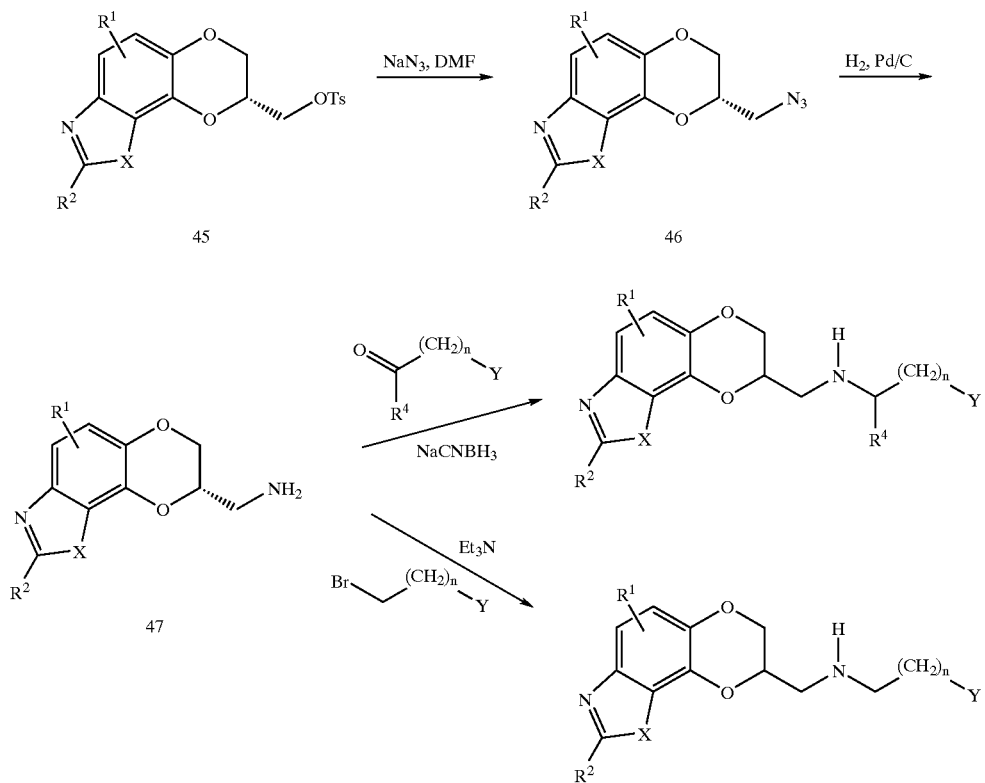

The gualacols, catechols, 2',3',4'-trihydroxyacylphenones and benzodioxan methyltosylates appropriate to the above chemistry are known compounds or can be prepared by one schooled in the art. The indole alkyl ketones, halides, alkylsulfonates and arylsulfonates are known compounds or they can readily be prepared by one schooled in the art using the procedures outlined by Smith, Yocca, Yevich and Matson in EP 464 558 A1 or by Bathe and Tilly in WO 0035872 A1. The indolealkylamines are known compounds or can readily be prepared by one schooled in the art from the halides or sulfonates by treatment with sodium azide or sodium cyanide, followed by reduction with hydrogen over the appropriate catalyst, either palladium on carbon or rhodium on alumina. The benzofuranylalkylamines and benzothiophenylalkylamines are known compounds or can readily be prepared by one schooled in the art from the known alcohols by first converting them to the bromides by treatment with triphenylphosphine and carbon tetrabromide, then displacing the bromide with either sodium azide or sodium cyanide and finally by reduction with hydrogen as described above for the indolealkylamines.

A protocol similar to that used by Cheetham et al. (*Neuropharmacol.* 32:737, 1993) was used to determine the affinity of the compounds of the invention for the serotonin transporter. The compound's ability to displace $^3$H-paroxetine from male rat frontal cortical membranes was determined using a Tom Tech filtration device to separate bound from free $^3$H-paroxetine and a Wallac 1205 Beta Plate® counter to quantitate bound radioactivity. $K_i$'s thus determined for standard clinical antidepressants are 1.96 nM for fluoxetine, 14.2 nM for imipramine and 67.6 nM for zimelidine. A strong correlation has been found between $^3$H-paroxetine binding in rat frontal cortex and $^3$H-serotonin uptake inhibition.

High affinity for the serotonin 5-HT$_{1A}$ receptor was established by testing the claimed compound's ability to displace [$^3$H] 8-OHDPAT (dipropylaminotetralin) from the 5-HT$_{1A}$ serotonin receptor following a modification of the procedure of Hall et al., *J. Neurochem.* 44, 1685 (1985) which utilizes CHO cells stably transfected with human 5-HT$_{1A}$ receptors. The 5-HT$_{1A}$ affinities for the compounds of the invention are reported below as $K_i$'s.

Antagonist activity at 5-HT$_{1A}$ receptors was established by using a $^{35}$S-GTPγS binding assay similar to that used by Lazareno and Birdsall (*Br. J. Pharmacol.* 109: 1120, 1993), in which the test compound's ability to affect the binding of $^{35}$S-GTPγS to membranes containing cloned human 5HT$_{1A}$ receptors was determined. Agonists produce an increase in binding whereas antagonists produce no increase but rather reverse the effects of the standard agonist 8-OHDPAT. The test compound's maximum inhibitory effect is represented as the $I_{max}$, while its potency is defined by the IC$_{50}$.

The results of the three standard experimental test procedures described in the preceding three paragraphs were as follows:

| Compound | 5-HT Transporter Affinity KI (nM) | 5-HT$_{1A}$ Receptor Affinity KI (nM) | 5-HT1A Function IC$_{50}$ (nM) (I$_{max}$) |
|---|---|---|---|
| Example 1 | 31.00 | 2.03 | 88.6 (80.3) |
| Example 2 | 34.00 | 19.89 | 49.4 (37.0) |
| Example 3 | 0.41 | 0.27 | 10.6 (98.7) |
| Example 4 | 47.00 | 4.19 | 909.1 (58.0) |
| Example 5 | 0.96 | 0.64 | 92.5 (76.8) |
| Example 6 | 3.57 | 0.39 | 31.3 (86.6) |

-continued

| Compound | | 5-HT Transporter Affinity KI (nM) | 5-HT$_{1A}$ Receptor Affinity KI (nM) | 5-HT1A Function IC$_{50}$ (nM) (I$_{max}$) |
|---|---|---|---|---|
| Example 7 | | 0.38 | 3.43 | 73.9 (100) |
| Example 8 | | 2.07 | 0.22 | 25.8 (94.1) |
| Example 9 | | 4.70 | 0.46 | 23.7 (95.2) |
| Example 10 | | 1.29 | 1.78 | 71.1 (61.5) |
| Example 11 | Isomer A | 1.62 | 1.68 | 27.8 (78.3) |
| | Isomer B | 0.43 | 4.65 | |
| Example 12 | | 13.00 | 1.55 | 137.6 (81.6) |
| Example 13 | | 1.05 | 0.32 | 64.6 (95.0) |
| Example 14 | | 1.00 | 1.03 | 507.3 (100) |
| Example 15 | | 1.60 | 5.16 | 411.8 (100) |
| Example 16 | | 1.80 | 2.51 | 125.1 (100) |
| Example 17 | | 46.00 | 0.63 | 52.0 (78.0) |
| Example 18 | | 6.60 | 0.35 | 10.4 (59.3) |
| Example 19 | | 14.60 | 0.20 | 50.1 (95.4) |
| Example 20 | | 2.82 | 0.38 | 188.3 (100) |
| Example 21 | | 62.00 | 0.60 | 25.9 (37.5) |
| Example 22 | | 4.30 | 7.12 | 878.0 (85.5) |
| Example 23 | | 1.85 | 0.70 | 19.3 (85.8) |
| Example 24 | | 1.40 | 4.45 | 156.9 (100) |
| Example 25 | | 0.60 | 5.47 | 43.5 (94.0) |
| Example 26 | | 5.90 | 3.26 | 180.4 (90.2) |
| Example 27 | | 6.70 | 52.85 | 340.6 (100) |
| Example 28 | | 5.50 | 0.28 | |
| Example 29 | | 0.90 | 1.64 | 55.8 (94.0) |
| Example 30 | | 1.80 | 5.35 | 68.0 (73.1) |
| Example 31 | | 2.40 | 35.30 | 205.4 (97.7) |
| Example 32 | | 1.00 | 5.46 | 232.7 (100) |
| Example 33 | | 2.20 | 21.21 | 200.1 (73.5) |
| Example 34 | | 8.10 | 0.29 | 193.1 (100) |
| Example 35 | | 2.40 | 0.56 | 66.6 (78.9) |
| Example 36 | | 1.90 | 16.29 | 486.2 (91.9) |
| Example 37 | | 2.60 | 1.12 | 21.4 (100) |
| Example 38 | | 1.31 | 0.06 | 25.8 (85.5) |
| Example 39 | | 0.50 | 0.85 | 263.2 (78.5) |
| Example 40 | | 7.00 | 17.67 | 1980.0 (100) |
| Example 41 | | 0.24 | 20.99 | |
| Example 42 | | 2.75 | 35.96 | |
| Example 43 | | 0.50 | 13.09 | 343.7 (100) |
| Example 44 | | 3.40 | 9.99 | 372.3 (100) |
| Example 45 | | 1.00 | 108.11 | 1086.0 (100) |
| Example 46 | | 6.70 | 0.05 | 31.4 (85.6) |
| Example 47 | | 1.00 | 4.42 | 191.1 (75.2) |
| Example 48 | | 4.20 | 24.66 | 500.0 (100) |
| Example 49 | | 23.0 | 0.73 | 99 (33) |
| Example 50 | | 9.7 | 0.45 | 69 (50) |
| Example 51 | | 2.35 | 0.78 | 19 (82) |
| Example 52 | | nd | 2.08 | EC$_{50}$ = 526 (E$_{max}$ = 97) |

Like the antidepressants fluoxetine, paroxetine and sertraline, the compounds of this invention have the ability to potently block the reuptake of the brain neurotransmitter serotonin. They are thus useful for the treatment of diseases commonly treated by the administration of serotonin selective reuptake inhibitor (SSRI) antidepressants, such as depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorders (including but not limited to trichotillomania), obsessive compulsive spectrum disorders (including but not limited to autism), social anxiety disorder, generalized anxiety disorder, obesity, eating disorders such as anorexia nervosa, bulimia nervosa, vasomotor flushing, cocaine and alcohol addiction, sexual dysfunction (including but not limited to premature ejaculation), incontinence (including, but not limited to fecal incontinence, urge incontinence, overflow incontinence, passive incontinence, reflex incontinence, stress urinary incontinence urinary exertional incontinence and urinary incontinence), and pain (including, but not limited to migraine, chronic back pain, phantom limb pain, neuropathic pain such as diabetic neuropathy, and post herpetic neuropathy) and related illnesses. Moreover, the compounds of this invention have potent affinity for and antagonist activity at brain $5HT_{1A}$ serotonin receptors. Recent clinical trials employing drug mixtures (e.g., fluoxetine and pindolol) have demonstrated a more rapid onset of antidepressant efficacy for a treatment combining SSRI activity and $5HT_{1A}$ antagonism (Blier and Bergeron, 1995; F. Artigas, et al., 1996; M. B. Tome, et al., 1997). The compounds of the invention are thus exceedingly interesting and useful for treating depressive illnesses.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remington's Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions that are sterile solutions or suspensions can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide, as used herein, means either directly administering a compound or composition of the present invention, or administering a prodrug, derivative or analog which will form an equivalent amount of the active compound or substance within the body.

The present invention includes prodrugs of compounds of Formula I, Ia and Ib. Prodrug, as used herein, means a compound which is convertible in vivo by metabolic means (e.g. by hydrolysis) to a compound of Formula I. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). *Design and Application of Prodrugs, Textbook of Drug Design and Development*, Chapter 5, 113–191 (1991), Bundgaard, et al., *Journal of Drug Deliver Reviews*, 8:1–38 (1992), Bundgaard, *J. of Pharmaceutical Sciences*, 77:285 et seq. (1988); and Higuchi and Stella (eds.) *Prodrugs as Novel Drug Delivery Systems*, American Chemical Society (1975).

The following examples illustrate the production of representative compounds of this invention.

INTERMEDIATE 1

3-Allyloxy-4-methoxynitrobenzene 97.5 g (0.51 mole) of the sodium salt of 5-nitroguaiacol was dissolved in one liter of DMF and 1.5 equivalents of allyl bromide added. The reaction was heated to 65° C. for two hours, after which time much of the dark color had discharged and tlc (1:1 $CH_2Cl_2$/hexane) indicated loss of starting material. The solvent was concentrated in vacuum and the residue washed with water. The product was isolated by filtration and dried in a vacuum. This gave 112 g of pale yellow solid. A sample recrystallized from methanol, gave m.p. 93–94° C.

INTERMEDIATE 2

2-Allyloxy-4-nitrothenol

To one liter of dimethyl sulfoxide was added 750 mL of 2 N aqueous sodium hydroxide and the mixture was heated to 65° C. The pale yellow solid 3-allyloxy-4-methoxynitrobenzene prepared above was added in portions over a 30 minute period and then the temperature was raised to 95° C. and maintained for 3 hours, after which time the starting material had been consumed. The mixture was allowed to cool and poured into a mixture of 1 L ice and 1 L 2 N HCl. 73 Grams of crude but homogeneous (by tlc 1:1 $CH_2Cl_2$/hexane) desired product was isolated as a light brown solid by filtration. This material was subsequently dissolved in 1:1 hexane/methylene chloride and filtered through silica gel to give 68 g of pale yellow solid, which, when recrystallized from ethyl/acetate/hexane, gave m.p. 61–62° C. The aqueous mother liquors from the initial crystallization above were extracted with 2 L of ethyl acetate. This was dried over sodium sulfate, filtered and evaporated to a dark oil. Column chromatography on silica with 1:1 $CH_2Cl_2$/hexane gave an additional 12 g of the title compound as a yellow solid. Elution with 2% MeOH in $CHCl_3$ gave 12 g of a dark oil which slowly crystallized in vacuum. This proved to be the Claisen product, 3-allyl-4-nitrocatechol.

INTERMEDIATE 3

2-(2-Allyoxy-4-nitrophonoxymethyl)-oxirane 20 g (0.50 mole) of 60% NaH/mineral oil was placed in a two liter flask and washed with 500 mL of hexane. 1 L of DMF was added, followed by 77 g (0.40 mole) of the 2-allyloxy-4-nitrophenol prepared in the previous step. Addition of the phenol was performed in portions under argon. After stirring the mixture for 30 minutes at room temperature under argon, 108 g (0.48 moles) of (R)-glycidyl tosylate was added and the mixture heated at 70–75° C. under nitrogen overnight. Upon cooling, the DMF was removed in vacuum and replaced with one liter of methylene chloride. This was washed with 500 mL portions of 2 N HCl, saturated sodium bicarbonate and saturated brine and dried over sodium sulfate. The mixture was filtered, concentrated to an oil in vacuum and column chromatographed on silica gel using 1:1 hexane/methylene chloride as eluant. This gave 43 g of product contaminated with traces of the two starting materials, followed by 21 g of pure product as a pale yellow solid. The impure material was recrystallized from 1.2 L of 10% ethyl acetate/hexane to give 34 g of pure (homogeneous on silica gel tlc with 1:1 hexane/methylene chloride) (R)-2-(2-allyloxy-4-nitrophenoxymethyl)-oxirane (m.p. 64° C.).

Elemental Analysis for: $C_{12}H_{13}NO_5$

Calc'd: C, 57.37; H, 5.21; N, 5.58. Found: C, 57.50; H, 5.21; N, 5.43.

INTERMEDIATE 4

(8-Allyl-7-nitro-2,3-dihydro-benz (1,4)di xin-2-yl)-m than I (R)-2-(2-Allyloxy-4-nitrophenoxymethyl)-oxirane (20 g, 80 mmol) prepared as above was heated at 155° C. in mesitylene for 24 hours under nitrogen. Filtration of the black solid that formed gave 1.5 g of very polar material. Evaporation of the solvent in vacuum followed by column chromatography on silica gel with methylene chloride as eluant gave 10 g of recovered starting material and 7.5 g of the desired rearranged (S)-(8-allyl-7-nitro-2,3-dihydro-benzo(1,4)dioxin-2-yl)-methanol, which slowly crystallized on standing in vacuum (m.p. 67° C.). The yield based on recovered starting material is 75%.

Elemental Analysis for: $C_{12}H_{13}NO_5$

Calc'd: C, 57.37; H, 5.21; N, 5.58. Found: C, 57.26; H, 5.20; N, 5.35.

INTERMEDIATE 5

Toluene-4-sulfonic acid 8-allyl-7-nitro-2,3-dihydro-benzo(1,4)dioxin-2-ylmethyl ester 9.55 g (38.0 mmol) of (S)-(8allyl-7-nitro-2,3-dihydro-benzo(1,4)dioxin-2-yl)-methanol was dissolved in 465 mL of pyridine, 29.0 g (152 mmol) of p-toluenesulfonyl chloride was added and the mixture stirred at room temperature under nitrogen overnight. Water was then added to quench the excess tosyl chloride and the solvent was removed in vacuum and replaced with methylene chloride. This solution was washed with 2 N HCl, with saturated sodium bicarbonate, and with saturated brine, and dried over magnesium sulfate. Filtration, evaporation in vacuum and column chromatography on silica gel with 1:1 hexane/methylene chloride as eluant gave 12.6 g (92%) of toluene-4-sulfonic acid (R)-allyl-7-nitro-2,3-benzo(1,4)dioxin-2-ylmethyl ester, which slowly crystallized to a tan solid (m.p. 60–62° C.) upon standing.

Elemental Analysis for: $C_{19}H_{19}NO_7S$

Calc'd: C, 56.29; H, 4.72; N, 3.45. Found: C, 56.13; H, 4.58; N, 3.44.

INTERMEDIATE 6

{7-Nitro-8-[1-propenyl]-2,3-dihydro-1,4-benzodioxin-2-yl}methyl 4-methylbenzenesulfonate To a solution of 10.0 g (24.0 mmol) of (R)-[8-allyl-7-nitro-2,3-dihydro-1,4-benzodioxin-2-yl]methyl 4-methylbenzenesulfonate in 700 mL of benzene was added 1.03 g of bis(acetonitrile)dichloropalladium (II) and the mixture was refluxed under nitrogen for 48 hours. The catalyst was then removed by filtration and the filtrate concentrated in vacuum to a brown oil. Column chromatography on silica gel with methylene chloride as eluent gave 7.2 g of the title compound as a mixture of E and Z isomers. A sample of {(2R)-7-nitro-8[(E)-1-propenyl]-2,3-dihydro-1,4-benzodioxin-2-yl}methyl 4-methylbenzenesulfonate was obtained as a yellow solid (m.p. 105–106° C.) by evaporation of a pure E isomer-containing fraction.

Elemental Analysis for: $C_{19}H_{19}NO_7S$

Calc'd: C, 56.29; H, 4.72; N, 3.45. Found: C, 56.12; H, 4.64; N, 3.39.

INTERMEDIATE 7

{7-Nitro-8-[3-oxo-1-propenyl]-2,3-dihydro-1,4-benzodioxin-2-yl}methyl 4-methylbenzenesulfonate {(2R)-7-nitro-8-[1-propenyl]-2,3-dihydro-1,4-benzodioxin-2-yl}methyl 4-methylbenzenesulfonate (6.15 g, 15.2 mmol) was dissolved in 180 mL of dioxane. Selenium dioxide (4.20 g, 37.9 mmol) was then added, followed by 0.70 mL of water. The heterogeneous mixture was heated at reflux under nitrogen for 5 hours. Upon cooling, the reaction was filtered and concentrated in vacuum to yield a dark yellow solid. This was dissolved in minimal ethyl acetate and column chromatographed on silica gel using 30% ethyl acetate in hexane as eluant to give 5.75 g of the (R)-enantiomer of the title compound as a light yellow solid (m.p. 138–140° C.).

Elemental Analysis for: $C_{19}H_{17}NO_8S$

Calc'd: C, 54.41; H, 4.09; N, 3.34. Found: C, 54.10; H, 3.85; N, 3.31.

INTERMEDIATE 8

2,3-Dihydro[1,4]dioxino[2,3-f]quinolin-2-ylmethyl 4-methylbenzenesulfonate

To a solution of {(2R)-7-nitro-8-[3oxo-1-propenyl]-2,3-dihydro-1,4-benzodioxin-2-yl}methyl 4-methylbenzenesulfonate (3.50 g, 8.35 mmol) in 200 mL of acetic acid/ethanol (1:1) was added 2.35 g (42.1 mmol) of iron powder and the mixture was heated at reflux under nitrogen for 8 hours. After the reaction was complete, 150 mL of water was added and the mixture filtered through a pad of celite. The filtrate was neutralized with saturated sodium bicarbonate and extracted with ethyl acetate. The extract was dried over magnesium sulfate, filtered and evaporated in vacuum. The residue was column chromatographed on silica gel using a gradient elution commencing with 20% ethyl acetate/hexane and ending with 70% ethyl acetate/hexane to give 1.85 g of the (R)-enantiomer of the title compound as a yellow oil. $^1$H-NMR (CDCl$_3$): doublet 8.8 δ (1 H); doublet 8.2 δ (1 H); doublet 7.8 δ (2 H); doublet 7.6 δ (1 H); multiplet 7.35 δ (1 H); multiplet 7.25 δ (3 H); multiplet 4.6 δ (1 H); multiplet 4.3–4.4 8 δ (3 H); multiplet 4.2 δ (1 H); singlet 2.4 δ (3 H).

INTERMEDIATE 9

(8-Formyl-7-nitro-2,3-dihydro-1,4-benzodioxin-2-yl) methyl 4-methylbenzenesulfonate {(2R)-7-Nitro-8-[1-propenyl]-2,3-dihydro-1,4-benzodioxin-2-yl}methyl 4-methylbenzenesulfonate (10.5 g, 25.9 mmol) dissolved in 400 mL of methylene chloride was treated with excess ozone at −78° C. Diisopropylethylamine (11.5 mL, 66.0 mmol) was then added dropwise over 30 minutes and the mixture allowed to come to room temperature and stir overnight under a nitrogen atmosphere. The mixture was then diluted to 600 mL with methylene chloride, washed three times with 100 mL portions of 2N HCl (aq), twice with 200 mL portions of saturated aqueous sodium bicarbonate and with 200 mL of saturated brine. The solution was dried over magnesium sulfate, filtered and concentrated in vacuum to a crude brown oil, which was column chromatographed on silica gel with 10% hexane/methylene chloride to give 7.52 g of the (R)-enantiomer of the title compound as a yellow solid. $^1$H-NMR (CDCl$_3$): doublet 7.8 δ (2 H); doublet 7.62 δ (1 H); doublet 7.4 δ (2 H); doublet 7.0 δ (1 H); multiplet 4.4–4.6 δ (2 H); multiplet 4.2 δ (3 H); singlet 2.4 δ (3 H).

INTERMEDIATE 10

{7-Nitro-8-[(E)-3-oxo-1-butenyl]-2,3-dihydro-1,4-benzodioxin-2-yl}methyl 4-methylbenzenesulfonate To a solution of 3.00 g (7.37 mmol) of [(2R)-8-formyl-7-nitro-2,3-dihydro-1,4-benzodioxin-2-yl]methyl 4-methylbenzenesulfonate in 250 mL of toluene was added 2.90 g (9.10 mmol) of 1-triphenylphosphorylidene-2-propanone. The mixture was stirred at room temperature under nitrogen for 5 hours, during which time some product precipitated from solution. The solvent was removed in vacuum and the crude residue was column chromatographed on silica gel with methylene chloride as eluant to give 3.0 g of the (R)-enantiomer of the title compound as a yellow solid. $^1$H-NMR (CDCl$_3$): doublet 7.8 δ (2 H); doublet 7.6 δ (1 H); doublet 7.5 δ (2 H); doublet 7.4 δ (2 H); doublet 6.95 δ (1 H); doublet 6.6 δ (1 H); multiplet 4.5 δ (1 H); doublet of doublets 4.0 δ (1 H); multiplet 4.2 δ (3 H); singlet 2.45 δ (3 H); singlet 2.4 δ (3 H).

INTERMEDIATE 11

(8-Methyl-2,3-dihydro[1,4]dioxino[2,3-f]quinolin-2-yl)methyl 4-methylbenzenesulfonate To a solution of {(2R)-7-nitro-8-[(E)-3-oxo-1-butenyl]-2,3-dihydro-1,4-benzodioxin-2-yl}methyl 4-methylbenzenesulfonate (3.40 g, 7.83 mmol) in 200 mL of acetic acid/ethanol (3:2) was added 2.25 g (40.2 mmol) of iron powder and the mixture was heated at reflux under nitrogen for 8 hours. After the reaction was complete, 150 mL of water was added and the mixture filtered through a pad of celite. The filtrate was neutralized with saturated aqueous sodium bicarbonate and extracted with ethyl acetate. The extract was dried over magnesium sulfate, filtered and evaporated in vacuum. The residue was column chromatographed on silica gel using a gradient elution commencing with 20% ethyl acetate/hexane and ending with 70% ethyl acetate/hexane to give 2.5 g of the (R)-enantiomer of the title compound as a yellow oil. $^1$H-NMR (CDCl$_3$): doublet 8.1 δ (1 H); doublet 7.6 δ (2 H); doublet 7.45 δ (1 H); multiplet 7.2 δ (4 H); multiplet 4.6 δ (1 H); multiplet 4.3 δ (3 H); multiplet 4.1 δ (1 H); singlet 2.5 δ (3H); singlet 2.4 δ (3 H).

INTERMEDIATE 12

{7-Nitro-8-[(E)-3-oxo-1-pentenyl]-2,3-dihydro-1,4-benzodioxin-2-yl}methyl 4-methylbenzenesulfonate To a solution of 5.00 g (12.2 mmol) of [(2R)-8-formyl-7-nitro-2,3-dihydro-1,4-benzodioxin-2-yl]methyl 4-methylbenzenesulfonate in 200 mL of toluene was added 5.10 g (15.3 mmol) of 1-triphenylphosphorylidene-2-butanone. The mixture was stirred at room temperature under nitrogen for 5 hours, after which time the solvent was removed in vacuum and the crude residue was column chromatographed on silica gel with methylene chloride as eluant to give 5.0 g of the (R)-enantiomer of the title compound as a yellow solid (m.p. 114° C.).

Elemental Analysis for: $C_{17}H_{15}NO_8S$

Calc'd: C, 56.37; H, 4.73; N, 3.13. Found: C, 56.81; H, 4.60; N, 3.01.

INTERMEDIATE 13

(8-Ethyl-2,3-dihydro[1,4]dioxino[2,3-f]quinolin-2-yl)methyl 4-methylbenzenesulfonate To a solution of {(2R)-7-nitro-8-[(E)-3-oxo-1-pentenyl]-2,3-dihydro-1,4-benzodioxin-2-yl}methyl 4-methylbenzenesulfonate (1.57 g, 3.50 mmol) in 100 mL of acetic acid/ethanol (1:1) was added 1.00 g (17.9 mmol) of iron powder and the mixture was heated at reflux under nitrogen for 8 hours. After the reaction was complete, 150 mL of water was added and the mixture filtered through a pad of celite. The filtrate was neutralized with saturated aqueous sodium bicarbonate and extracted with ethyl acetate. The extract was dried over magnesium sulfate, filtered and evaporated in vacuum. The residue was column chromatographed on silica gel using a gradient elution commencing with 20% ethyl acetate/hexane and ending with 70% ethyl acetate/hexane to give 0.94 g of the (R)-enantiomer of the title compound as a yellow oil. $^1$H-NMR (CDCl$_3$): doublet 8.2 δ (1 H); doublet 7.8 δ (2 H); doublet 7.55 δ (1 H); 7.2–7.3 δ (4 H); multiplet 4.6 δ (1 H); multiplet 4.2–4.4 δ (3 H); multiplet 4.1 δ (1 H); quartet 3.0 δ (2 H); singlet 2.4 δ (3 H); triplet 1.4 δ (3 H).

INTERMEDIATE 14

1-[5-Hydroxy-3-(hydroxymethyl)-2,3-dihydro-1,4-benzodioxin-6-yl]-1-ethanone

To a solution of 2',3',4'-trihydroxyacetophenone (10.6 g, 63.0 mmol) in DMF (75 mL) was added potassium carbonate (17.4 g, 126 mmol). After 5 minutes (R)-glycidyl tosylate (9.67 g, 42.3 mmol) was added, then the heterogeneous mixture was heated to 70° C. for 3 hours. After removal of the solvent in vacuum, the residue was taken into water (800 mL) and was then extracted with ethyl acetate (4×300 mL). The combined organic layers were dried over magnesium sulfate, filtered and evaporate to dryness in vacuum. The crude brown oil thus obtained was column chromatographed on silica gel with 40% hexane/ethyl acetate as eluant to give the (S)-enantiomer of the title compound as a yellow oil which solidifies upon standing (7.5 g, 78%). MS (ESI) m/z 223 (M−H)−.

Elemental Analysis for: $C_{11}H_{12}O_5$.0.10 $H_2O$

Calc'd: C, 58.46; H, 5.44. Found: C, 58.02; H, 5.09.

INTERMEDIATE 15

1-[5-Hydroxy-3-(hydroxymethyl)-2,3-dihydro-1,4-benzodioxin-6-yl]-1-ethanone oxime A solution of hydroxylamine hydrochloride (2.38 g, 34.2 mmol) in 1:1 ethanol/pyridine (100 mL) was added to a solution of 1-[(3S)-5-hydroxy-3-(hydroxymethyl)-2,3-dihydro-1,4-benzodioxin-6-yl]-1-ethanone (1.92 g, 8.57 mmol) in ethanol (200 mL). It was then heated to reflux under nitrogen for 5 hours. Upon cooling, the solvent was removed and replaced with ethyl acetate. The solution was then washed with water (200 mL) and with aqueous 2N HCl (100 mL), dried over magnesium sulfate, filtered and evaporated in vacuum to give 1.89 g (93%) of the (S)-enantiomer of the title compound as a gray solid, m.p. 162° C. MS (ESI) m/z 240 (M+H)+.

Elemental Analysis for: $C_{11}H_{13}NO_5$.0.35 $H_2O$

Calc'd: C, 53.81; H, 5.62; N, 5.71. Found: C, 53.51; H, 5.30; N, 5.58.

INTERMEDIATE 16

[2-Methyl-7,8-dihydro[1,4]dioxino[2,3-g][1,3]benzoxazol-8-yl]methanol 3.03 g (12.6 mmol) of 1-[(3S)-5-hydroxy-3-(hydroxymethyl)-2,3-dihydro-1,4-benzodioxin-6-yl]-1-ethanone oxime was dissolved in a mixture of 1:3 N,N-dimethylacetamide/acetonitrile (100 mL). The solution was cooled in an ice/water bath and a solution of phosphorus oxychloride (1.26 mL, 35 mmol) in 1:3 N,N-dimethylacetamide/acetonitrile (30 mL) was added. The reaction mixture was stirred under nitrogen over a period of 48 hours. It was then added to an ice cold, saturated solution of sodium acetate, extracted with ethyl acetate, dried over magnesium sulfate, filtered and evaporated in vacuum. The resulting crude oil was column chromatographed on silica gel with 60% hexane/ethyl acetate to remove impurities and the product eluted with 40% hexane/ethyl acetate. After evaporation of the solvent in vacuum, 2.08 g (75%) of the (S)-enantiomer of the title compound was obtained as a white solid, m.p. 120° C. MS (ESI) m/z 222 (M+H)+.

Elemental Analysis for: $C_{11}H_{11}NO_4$.0.20 $H_2O$

Calc'd: C, 58.77; H, 5.11; N, 6.23. Found: C, 58.93; H, 4.91; N, 6.14.

INTERMEDIATE 17

[2-Methyl-7,8-dihydro[1,4]dioxino[2,3-g][1,3]benzoxazol-8-yl]methyl 4-methylbenzenesulfonate To a solution of [(8S)-2-methyl-7,8-dihydro[1,4]dioxino[2,3-g][1,3]benzoxazol-8-yl]methanol (1.80 g, 8.14 mmol) in methylene chloride (100 mL) was added p-toluenesulfonyl chloride (3.90 g, 20.4 mmol). The mixture was cooled in an ice bath and a solution of diisopropylethylamine (3.55 mL, 20.4 mmol) in methylene chloride (20 mL) was then added dropwise, followed by 4-dimethylaminopyridine (0.65 g, 5.30 mmol). The solution was allowed to warm to room temperature and was stirred under nitrogen overnight. The reaction was diluted to 500 mL in volume with methylene chloride, then washed with aqueous 2 N HCl (200 mL), with saturated aqueous sodium bicarbonate (200 mL), and with brine (150 mL), dried over magnesium sulfate, filtered and evaporated in vacuum to a yellow oil. The crude oil was column chromatographed on silica gel using methylene chloride to remove impurities and 3% methanol/methylene chloride to elute the (R)-enantiomer of the title compound, which becomes a white solid under vacuum (2.56 g, 84%), m.p. 123° C. MS (ESI) m/z 376 (M+H)+.

Elemental Analysis for: $C_{18}H_{17}NO_6S$.0.20 $H_2O$

Calc'd: C, 57.04; H, 4.63; N, 3.70. Found: C, 56.75; H, 4.62; N, 3.51.

INTERMEDIATE 18

5-Bromo-6-methoxy-2-methylquinoline

A solution of 6-methoxy-2-methylquinoline (177 g, 1.02 mol) in acetonitrile (1.77 L) was cooled to 0–3° C. followed by portion-wise addition of N-bromo-succinimide (200 g, 1.12 mol) over a period of 30 minutes while maintaining the same temperature. The resulted brown slurry was warmed to ambient temperature and stirred for an additional 6 hours. The reaction was then quenched by a 10% NaHSO$_3$ solution (211 mL). The reaction mixture was concentrated to a volume of 600 mL then slowly poured into 0.1 N NaOH (2.5 L). The slurry (pH=9) was stirred at room temperature for 1 hour then filtered, washed with water (2×1 L) and dried in a vacuum oven to give 253 g (98.6%) of the title compound as a brown solid. R$_f$=0.39 (3:7) ethyl acetate:heptane; $^1$H NMR (DMSO) δ 8.30 (d, J=6.5 Hz, 1H), 7.98 (d, J=6.9 Hz, 1H), 7.70 (d, J=7.0 Hz, 1H), 7.47 (d, J=6.5 Hz, 1H), 4.02 (s, 3H), 2.66 (s, 3H);

Elemental Analysis for: $C_{11}H_{10}NOBr$

Calc'd: C, 52.40; H, 3.97; N, 5.56. Found: C, 52.13; H, 3.94; N, 5.61.

INTERMEDIATE 19

5-Bromo-2-m thyl-6-quinolinol

A mixture of 5-bromo-2-methyl-6-methoxyquinoline (30 g, 0.12 mol) in 48% HBr (135 mL) was heated to reflux for 7 hours then cooled to 5° C. in 1 hour to give a brown and thick slurry. The slurry was stirred at 0–5° C. for 1 hour then filtered, washed with ethyl acetate (2×50 mL) and dried in a vacuum oven to give 34.9 g (92%) of the hydrobromide of the title compound as a brown solid. $^1$H NMR (DMSO) δ 8.26 (d, J=8.7 Hz, 1H), 7.85 (d, J=9.1 Hz, 1H), 7.56 (d, J=9.1 Hz, 1H), 7.45 (d, J=8.7 Hz, 1H), 2.64 (s, 3H). A slurry of the hydrobromide salt of 5-bromo-2-methyl-6-quinolinol (3.4 g, 10.5 mmol) and Amberlyst A-21 ion-exchange resin (1.7 g, pre-washed with MeOH then dried in oven) in MeOH (35 mL) was stirred at room temperature for 3 h. The mixture was then filtered and concentrated in vacuo to give 2.5 g (100%) of a yellow solid. $R_f$=0.36 (1:1) Ethyl acetate:heptane; $^1$H NMR (DMSO) δ 8.26 (d, J=8.4 Hz, 1H), 7.82 (d, J=9.3 Hz, 1H), 7.47 (t, J=9.1 Hz, 2H ), 2.66 (s, 3H).

INTERMEDIATE 20

(2S)-1-(Benzyloxy)-3-[(5-bromo-2-methyl-quinolinyl)oxy]-2-propanol

A solution of 5-bromo-2-methyl-6-quinolinol (30.1 g, 126 mmol), (R)-benzyl glycidyl ether (24.9 g, 152 mmol) and triethylamine (17.4 g, 172 mmol) in DMA (200 mL) was heated in a 95–98° C. oil bath for 2 days. The solution was cooled and poured into water (300 mL) while stirring. The tan precipitate formed was filtered, washed with water (100 mL) and dried in a vacuum oven to give 37 g (73%) of the title compound as a tan solid. $R_f$=0.35 (ethyl acetate); $^1$H NMR (DMSO) δ 8.31 (d, J=8.8 Hz, 1H), 7.96 (d, J=9.2 Hz, 1H), 7.72 (d, J=9.3 Hz, 1H), 7.74 (d, J=8.7 Hz, 1H), 7.25–7.36 (m, 5H), 5.28 (d, J=5.1 Hz, 1H), 4.56 (s, 2H), 4.22–4.29 (m, 2H), 4.08–4.15 (m, 1H), 3.61–3.73 (m, 2H), 2.66 (s, 3H); Specific rotation=+6.2° (c=1, $CH_3OH$);

Elemental Analysis for: $C_{20}H_{20}BrNO_3$

Calc'd: C, 59.66; H, 4.97; N, 3.48. Found: C, 59.43; H, 4.97; N, 3.55.

INTERMEDIATE 21

(2S)-2[(Benzyloxy)methyl-8-methyl-2,3-dihydro[1,4]dioxino-[2,3-f]quinolin

To a mixture of (2S)-1-(benzyloxy)-3-[5-bromo-2-methyl-6-quinolinyl)oxyl]-2-propanol (100 g, 0.249 mol) and copper (I) iodide (47.4 g, 0.249 mol) in toluene (2 L), NaH (10.9 g, 0.45 mol) was added in portions at 30–35° C. over 20 minutes. The reaction mixture was kept at 35° C. for 30 minutes then heated to 110° C. slowly. After 30 minutes, the reaction was cooled to 60° C., additional NaH (10.9 g, 0.45 mol) was added. This was warmed to 110° C. for an additional 2 hours then cooled to rt before dropwise addition of water (200 mL). After stirring for 15 minutes, the mixture was filtered through a bed of celite then washed with toluene (3×50 mL) and water (50 mL). The two layers were separated. The organic layer was extracted with water (100 mL), $NH_4OH$ (100 mL), 25% NaCl (100 mL) and concentrated in vacuo to give 387.6 g of the crude product as a brown syrup. The crude product was carried through to the debenzylation step before purification.

INTERMEDIATE 22

[(2R)-8-Methyl-2,3-dihydro[1,4]dioxino[2,3-f]quinolin-2-yl]methanol

To a solution of (2S)-2[(benzyloxy)methyl-8-methyl-2,3-dihydro[1,4]dioxino[2,3-f]quinoline (0.16 g, 0.5 mmol) in EtOH (1 mL) was added cyclohexene (0.5 mL) then 10% Pd/C (0.016 g, 10 mol %). The mixture was heated to reflux under $N_2$ for 18 hours then cooled and filtered. The catalyst was rinsed with methanol and the filtrate was concentrated in vacuo to afford 0.113 g (98%) of the title alcohol as an off-white solid. $^1$H NMR ($CD_3OD$) δ 8.46 (m, 1H), 7.47 (m, 1H), 7.38–7.31 (m, 2H), 4.40 (m, 1H), 4.36 (m, 1H), 4.18 (m, 1H), 3.91 (m, 2H), 2.68 (s, 3H).

INTERMEDIATE 23

[(2R)-8-M thyl-2,3-dihydro[1,4]dioxino[2,3-f]quinolin-2-yl]methyl 4-bromobenzenesulfonate A solution of [(2S)-8-methyl-2,3-dihydro[1,4]dioxino[2,3-f]quinolin-2-yl]-methanol (4.0 g, 17.3 mmol), brosyl chloride (4.86 g, 19.0 mmol), dimethylamino pyridine (20 mg, 0.16 mmol) and triethylamine (3.62 mL, 25.8 mmol) in toluene (40 mL) was stirred at 60° C. for 6 hours. The reaction mixture was cooled to room temperature then water (20 mL) was added. After 30 minutes, the two layers were separated. The organic layer was extracted with 8% $NaHCO_3$ (20 mL) and $H_2O$ (20 mL), dried over $Na_2SO_4$, filtered and concentrated in vacuo. The solid obtained was dissolved in isopropyl alcohol (50 mL) and toluene (10 mL) at 80° C., cooled to room temperature over 1 hour then filtered, washed with (5:1) IPA: toluene (2×5 mL) and dried in a vacuum oven to give 5.99 g (76.9%) of the title compound as an off-white solid. $^{13}$C NMR ($CDCl_3$) δ 157.9, 144.3, 138.1, 134.7, 132.9, 129.7, 129.6, 129.0, 122.4, 121.7, 121.3, 118.8, 70.7, 67.6, 64.5, 25.4

INTERMEDIATE 24

C-(8-Methyl-2,3-dihydro-[1,4]dioxino[2,3-f]quinolin-2-yl)-methylamine

A mixture of [(2R)-8-methyl-2,3-dihydro[1,4]dioxino[2,3-f]quinolin-2-yl]methyl 4-bromobenzenesulfonate (0.45 g, 1.0 mmol) and sodium azide (0.33 g, 5.0 mmol) in 50 mL of DMF was heated at 60° C. under nitrogen for 15 hours. The solvent was removed in vacuum and the residue redissolved in 300 mL of methylene chloride and washed with 300 mL portions of water and saturated brine, dried over magnesium sulfate, filtered and concentrated in vacuum to 0.25 g of a yellow oil. The oil was redissolved in 100 mL of methanol into which 100 mg of 10% Pd/C and 0.3 mL conc. HCl had been added. The mixture was treated with hydrogen at 50 psi in a Parr apparatus for 6 hours, then filtered through celite and concentrated in vacuum. Recrystallization of the residue from ethanol gave 0.18 g of the (S)-enantiomer of the title compound as a yellow dihydrochloride, m.p. >250° C.

Elemental Analysis for $C_{13}H_{14}N_2O_2$.2 $HCl.H_2O$

Calc'd: C, 48.61; H, 5.65; N, 8.72. Found: C, 48.59; H, 5.51; N, 8.62.

INTERMEDIATE 25

3-(3-Bromopropyl)benzofuran

To a 0° C. solution of triphenylphosphine (2.07 g, 7.90 mmol) in methylene chloride (20 mL) was added bromine (0.4 mL, 7.90 mmol) dropwise. To the resulting cloudy mixture was added a solution of 3-benzofuran-3-yl-propan-1-ol (1.16 g, 6.58 mmol) and pyridine (1.07 mL, 13.2 mmol) in methylene chloride (10 mL). The reaction was stirred at room temperature for 4 hours, then was diluted with diethyl ether (100 mL) and filtered. The ethereal solution was washed with 1 M aqueous potassium hydrogen sulfate (50 mL), then with saturated aqueous sodium bicarbonate (50 mL), and finally with brine (50 mL), then was dried over anhydrous magnesium sulfate, filtered, and concentrated in vacuum. Flash chromatography on $SiO_2$ ($CH_2Cl_2$) afforded 1.5 g (96%) of the title compound: $^1$H NMR ($CDCl_3$, 400 MHz) δ 7.56 (d, J=7.8 Hz, 1 H), 7.47 (d, J=8.1 Hz, 1 H), 7.46 (s, 1 H), 7.7.22–7.35 (m, 2 H), 3.45 (t, J=6.4 Hz, 2 H), 2.87 (t, J=7.1 Hz, 2 H), 2.25 (quint, J=7.2 Hz, 2 H).

INTERMEDIATE 26

3-(2-Bromoethyl)-7-methoxybenzofuran

This compound was prepared by the same method as for intermediate 25, using 4.15 g (21.6 mmol) of 2-(7-methoxybenzofuran-3-yl)-ethanol, 6.8 g (25.9 mmol) of triphenylphosphine, 1.34 mL (25.9 mmol) of bromine, and 3.5 mL (43.2 mmol) of pyridine in 70 mL of $CH_2Cl_2$, to afford 2.87 g (52%) of the title compound after flash chromatography on $SiO_2$ (25% $CH_2Cl_2$/hexanes to 100% $CH_2Cl_2$ gradient): MS (ESI) m/z 254 $[M]^+$.

Elemental Analysis for: $C_{11}H_{11}BrO_2$

Calc'd: C, 51.79; H, 4.35. Found: C, 52.11; H, 4.07.

INTERMEDIATE 27

4-B nzo[b]thloph n-3-yl-butyronitril

To a solution of 3-(3-bromopropyl)-benzo[b]thiophene (1.78 g, 6.97 mmol) in anhydrous DMF (7 mL) under a nitrogen atmosphere was added sodium cyanide (0.683 g, 13.9 mmol). The reaction was allowed to stir at ambient temperature for 2 days, then was poured into $H_2O$ (100 mL) and extracted with diethyl ether (3×100 mL). The combined organic layers were washed with 1:1 brine/$H_2O$ (2×100 mL) and brine (100 mL), then were dried over anhydrous magnesium sulfate, filtered and concentrated in vacuo, to afford 1.27 g (91%) of the title compound as a yellow oil.

INTERMEDIATE 28

3-Benzofuran-3-yl-propionitrile

This compound was prepared by the same method as for intermediate 27, using 1.98 g (8.8 mmol) of 3-(2-bromoethyl)benzofuran and 0.86 g (17.6 mmol) of NaCN, to afford 1.5 g (quant.) of the title compound: MS (ESI) m/z 171 $[M]^+$.

Elemental Analysis for: $C_{11}H_9NO$

Calc'd: C, 77.17; H, 5.30; N, 8.18. Found: C, 77.14; H, 5.45; N, 8.19.

INTERMEDIATE 29

3-(7-Methoxybenzofuran-3-yl)-propionitrile

This compound was prepared by the same method as for intermediate 27, using 2.87 g (11.25 mmol) of 3-(2-bromoethyl)-7-methoxybenzofuran and 1.1 g (22.5 mmol) of sodium cyanide, to afford 2.2 g (97%) of the title compound: MS (ESI) m/z 201 $[M]^+$.

Elemental Analysis for: $C_{12}H_{11}NO_2$

Calc'd: C, 71.63; H, 5.51; N, 6.96. Found: C, 71.57; H, 5.33; N, 6.62.

INTERMEDIATE 30

3-Benzofuran-3-yl-propylamine

A mixture of 3-benzofuran-3-yl-propionitrile (0.87 g, 5.08 mmol) and 300 mg of 5% rhodium on alumina in concentrated ammonium hydroxide (60 mL) and ethanol (100 mL) was hydrogenated at 50 psi overnight. The catalyst was removed by vacuum filtration through celite, washing with excess ethanol. The filtrate was concentrated in vacuum. The residue was diluted with ethyl acetate, the aqueous phase was removed, and the organic layer was dried over anhydrous magnesium sulfate, then filtered and concentrated in vacuum. Flash chromatography on $SiO_2$ (1/2/97 to 3/2/95 methanol/2M $NH_3$ in methanol/$CH_2Cl_2$ gradient) afforded 700 mg (85%) of the title compound: $^1$H NMR ($CDCl_3$, 400 MHz): δ 7.53 (d, J=8.1 Hz, 1H), 7.43 (d, J=8.0 Hz), 7.18–7.30 (m, 2H), 2.78 (t, J=7.0 Hz, 2H), 2.71 (t, J=8.0 Hz, 2H), 1.85 (quint, J=7.2 Hz, 2 H).

INTERMEDIATE 31

4-Benzofuran-3-yl-butylamine

This compound was prepared by the same method as for intermediate 30, using 4-benzofuran-3-yl-butyronitrile (1.05 g, 5.67 mmol), 420 mg of 5% rhodium on alumina, 100 mL of ammonium hydroxide, and 150 mL of ethanol, to afford 770 mg (72%) of the title compound after chromatography: $^1$H NMR ($CDCl_3$, 400 MHz) δ 7.52 (d, J=8.2 Hz, 1 H), 7.43 (d, J=8.1 Hz, 1 H), 7.38 (s, 1 H), 7.18–7.27 (m, 2 H), 2.72 (t, J=7.0 Hz, 2 H), 2.67 (t, J=7.3 Hz, 2 H), 1.73 (quint, J=7.9 Hz, 2 H).

INTERMEDIATE 32

3-(7-Methoxybenzofuran-3-yl)-propylamine

This compound was prepared by the same method as for intermediate 30, using 3-(7-methoxybenzofuran-3-yl)-propionitrile (1.0 g, 4.97 mmol), 400 mg of 5% rhodium on alumina, 100 mL of ammonium hydroxide, and 150 mL of ethanol, to afford 770 mg (76%) of the title compound after chromatography: MS (ESI) m/z 206 $[M+H]^+$.

Elemental Analysis for: $C_{12}H_{15}NO_2 \cdot 0.4 H_2O$

Calc'd: C, 67.84; H, 7.50; N, 6.59. Found: C, 68.06; H, 5.42; N, 6.49.

EXAMPLE 1

N-[2-(5-Methoxy-1H-indol-3-yl)-ethyl]-N-8-methyl-2,3-dihydro[1,4]dioxino[2,3-f]quinolin-2-ylmethyl)-amine To a mixture of [(2R)-8-methyl-2,3-dihydro[1,4]dioxino[2,3-f]quinolin-2-yl]methyl 4-bromobenzenesulfonate (0.80 g, 1.8 mmol) and 2-(5-methoxy-1H-indol-3-yl)-ethylamine (1.05 g, 5.50 mmol) was added 10 mL of DMSO. The mixture was stirred at 85° C. for 4.5 hours. The solvent was evaporated at reduced pressure. The residue was partitioned between 500 mL each of ethyl acetate and saturated aqueous sodium bicarbonate. The ethyl acetate layer was washed with water 5 times (250 mL) and dried over anhydrous magnesium sulfate. Filtration and concentration in vacuum gave 0.87 g of oil. This was chromatographed on silica gel with gradient elution commencing with 1:1 ethyl acetate/hexane and ending with ethyl acetate to give 0.39 g of the free base as an oil. The oil was dissolved in ethanol and added to a solution of oxalic acid dihydrate (0.135 g, 1.07 mmol) in ethanol. Filtration gave 0.426 g of the (S)-enantiomer of the title compound as an off-white oxalate, m.p. dec>240° C.

Elemental Analysis for: $C_{24}H_{25}N_3O_3 \cdot C_2H_2O_4 \cdot 2/3 H_2O$

Calc'd: C, 61.77; H, 5.65; N, 8.31. Found: C, 61.85; H, 5.41; N, 8.23.

EXAMPLE 2

N-[2-5-Chloro-1H-indol-3-yl)ethyl]-N-(8-methyl-2, 3-dihydro-[1,4]dioxino[2,3-f]quinolin-2-ylmethyl) amine To a mixture of [(2R)-8-methyl-2,3-dihydro[1,4]dioxino [2,3-f]quinolin-2-yl]methyl 4-bromobenzenesulfonate (0.648 g, 1,48 mmol) and 2-(5-chloro-1H-indol-3-yl)-ethylamine (0.956 g, 4.14 mmol) was added sodium carbonate (0.87 g, 8.2 mmol) and 10 mL of DMSO. The mixture was stirred at 85° C. for 4.5 hours. The solvent was evaporated at reduced pressure. The residue was partitioned between 500 mL each of ethyl acetate and saturated aqueous sodium bicarbonate. The ethyl acetate layer was washed with water 5 times (250 mL) and dried over anhydrous magnesium sulfate. Filtration and concentration in vacuum gave 0.91 g of crude material. This was chromatographed on silica gel with gradient elution commencing with 1:1 ethyl acetate/hexane and ending with ethyl acetate to give 0.19 g of the free base as an oil. This was dissolved in ethanol and added to a solution of oxalic acid dihydrate (0.066 g, 0.520 mmol) in ethanol. Filtration gave 0.203 g of the (S)-enantiomer of the title compound as an off-white oxalate, m.p. dec>240° C.

Elemental Analysis for: $C_{23}H_{22}ClN_3O_2 \cdot C_2H_2O_4 \cdot 3/4 H_2O$

Calc'd: C, 58.71; H, 5.03; N, 8.22. Found: C, 58.71; H, 4.60; N, 7.79.

EXAMPLE 3

N-[3-(5-Fluoro-1H-Indolyl-3-yl)propyl]-N-(8-methyl-2,3-dihydro-[1,4]dioxino[2,3-f]quinolin-2-ylmethyl)amine To a mixture of [(2R)-8-methyl-2,3-dihydro[1,4]dioxino [2,3-f]quinolin-2-yl]methyl 4-bromobenzenesulfonate (6.78 g, 15.1 mmol) and 2-(5-fluoro-1H-indol-3-yl)-propylamine (5.48 g, 28.5 mmol) was added sodium carbonate (5.07 g, 47.8 mmol) and 30 mL of DMSO. The mixture was stirred at 80° C. for 18 hours. The solvent was evaporated at reduced pressure. The residue was partitioned between 500 mL each of ethyl acetate and water. The ethyl acetate layer was washed with water 3 times (250 mL) and dried over anhydrous magnesium sulfate. Filtration and concentration in vacuum gave 9.00 g of crude material. This was chromatographed on silica gel with gradient elution commencing with 1:1 ethyl acetate/hexane and ending with ethyl acetate to give 3.77 g of the free base as a light tan oil. The oil was dissolved in ethanol and added to a warm solution of fumaric acid (1.18 g, 10.2 mmol) in ethanol. Filtration gave 4.22 g of the (S)-enantiomer of the title compound as a white fumarate, m.p. 207–209° C.

Elemental Analysis for: $C_{24}H_{24}FN_3O_2 \cdot C_4H_4O_4$

Calc'd: C, 64.48; H, 5.41; N, 8.06. Found: C, 64.37; H, 5.55; N, 7.98.

EXAMPLE 4

N-[2-(5-Fluoro-1H-indol-3-yl)ethyl]-N-(8-methyl-2, 3-dihydro-[1,4]dioxino[2,3-f]quinolin-2-ylmethyl) amine To a mixture of [(2R)-8-methyl-2,3-dihydro[1,4]dioxino [2,3-f]quinolin-2-yl]methyl 4-bromobenzenesulfonate (0.71 g, 1.5 mmol) and 2-(5-fluoro-1H-indol-3-yl)-ethylamine (1.06 g, 4.94 mmol) was added sodium carbonate (1.05 g, 9.91 mmol) and 10 mL of DMSO. The mixture was stirred at 85° C. for 5 hours. The solvent was evaporated at reduced pressure. The residue was partitioned between 500 mL each of ethyl acetate and water. The ethyl acetate layer was washed with water twice (250 mL) and dried over anhydrous magnesium sulfate. Filtration and concentration in vacuum gave 0.75 g of oil. This was chromatographed on silica gel with 0–5% methanol/ethyl acetate to give 0.14 g of the free base as a pure oil. This was dissolved in ethanol and added to a solution of oxalic acid dihydrate (0.050 g, 0.40 mmol) in ethanol. Filtration gave 0.135 g of the (S)-enantiomer of the title compound as a light yellow oxalate, m.p. dec. >245° C.

Elemental Analysis for: $C_{23}H_{22}FN_3O_2 \cdot C_2H_2O_4 \cdot 6/10 H_2O$

Calc'd: C, 61.00; H, 5.16; N, 8.54. Found: C, 60.98; H, 5.24; N, 8.48.

EXAMPLE 5

N-[3-(5-Fluoro-1H-Indol-3-yl)propyl]-N-(8-ethyl-2, 3-dihydro-[1,4]dioxino[2,3-f]quinolin-2-ylmethyl) amine To a mixture [(2R)-8-ethyl-2,3-dihydro[1,4]dioxino[2,3-f]quinolin-2-yl]methyl 4-toluenesulfonate (0.46 g, 1.2 mmol) and 2-(5-fluoro-1H-indol-3-yl)-ethylamine (0.428 g, 2.23 mmol) was added sodium carbonate (0.392 g, 3.70 mmol) and 1.5 mL of DMSO. The mixture was stirred at 80° C. for 18 hours. The solvent was evaporated at reduced pressure. The residue was partitioned between 500 mL each of ethyl acetate and water. The ethyl acetate layer was washed twice with water (250 mL), once with saturated brine (250 mL) and dried over anhydrous magnesium sulfate. Filtration and concentration in vacuum gave 0.81 g of crude oil. This was chromatographed on silica gel with a gradient of ethyl acetate and methanol to give 0.26 g of the free base. This was dissolved in ethanol and added to a solution of oxalic acid dihydrate (0.076 g, 0.60 mmol) in ethanol. Filtration gave 0.256 g of the (S)-enantiomer of the title compound as a white oxalate, m.p. dec. >230° C.

Elemental Analysis for: $C_{25}H_{26}FN_3O_2 \cdot C_2H_2O_4$

Calc'd: C, 63.61; H, 5.54; N, 8.24. Found: C, 63.31; H, 5.48; N, 8.06.

EXAMPLE 6

N-[3-(1H-Indol-3-yl)propyl]-N-(8-methyl-2,3-dihydro-[1,4]dioxino[2,3-f]quinolin-2-ylmethyl) amine To a mixture of [(2R)-8-methyl-2,3-dihydro[1,4]dioxino [2,3-f]quinolin-2-yl]methyl 4-bromobenzenesulfonate (1.29 g, 2.86 mmol) and 2-(1H-indol-3-yl)-propylamine (0.97 g, 5.6 mmol) was added sodium carbonate (0.96 g, 9.1 mmol) and 5 mL of DMSO. The mixture was stirred at 85° C. for 18 hours and then allowed to stand at room temperature for 2 days. The solvent was evaporated at reduced pressure. The residue was partitioned between 500 mL each of ethyl acetate and water. The ethyl acetate layer was washed with water 3 times (250 mL) and dried over anhydrous magnesium sulfate. Filtration and concentration in vacuum gave 1.61 g of dark oil. This was chromatographed on silica gel with 15% methanol in ethyl acetate. The cleanest fractions were combined and evaporated to give 0.36 g of the free base compound as an oil. This was dissolved in ethanol and added to a solution of fumaric acid (0.120 g, 1.04 mmol) in ethanol. Filtration gave 0.399 g of the (S)-enantiomer of the title compound as a tan fumarate, m.p. 202–203° C.

Elemental Analysis for: $C_{24}H_{25}N_3O_2 \cdot C_4H_4O_4$

Calc'd: C, 66.79; H, 5.80; N, 8.34. Found: C, 66.79; H, 5.91; N, 8.22.

EXAMPLE 7

N-[3-(5-Fluoro-1H-indol-3-yl)propyl]-N-methyl-N-(8-methyl-2,3-dihydro-[1,4]dioxino[2,3-f]quinolin-2-ylmethyl)amine To a mixture of [(2R)-8-methyl-2,3-dihydro[1,4]dioxino[2,3-f]quinolin-2-yl]methyl 4-bromobenzenesulfonate (1.02 g, 2.27 mmol) and [3-(5-fluoro-1H-indol-3-yl)-propyl]-methyl-amine (0.54 g, 2.6 mmol) was added sodium carbonate (0.30 g, 2.8 mmol) and 7 mL of DMSO. The mixture was stirred at 100° C. for 18 hours and then at room temperature overnight. The solvent was evaporated at reduced pressure. The residue was partitioned between 500 mL each of ethyl acetate and water. The ethyl acetate layer was washed with water 4 times (250 mL) and dried over anhydrous magnesium sulfate. Evaporation of the solvent gave 2.0 g of crude material. This was chromatographed on silica gel with 0–5% methanol/ethyl acetate to give 0.38 g of the free base as an oil. This was dissolved in ethanol and added to a solution of fumaric acid (0.1173 g, 1.011 mmol) in ethanol. Filtration gave 0.374 g of the (S)-enantiomer of the title compound as light yellow fumarate, m.p. 104–120° C.

Elemental Analysis for: $C_{25}H_{26}FN_3O_2 \cdot C_4H_4O_4 \cdot H_2O$

Calc'd: C, 62.92; H, 5.83; N, 7.59. Found: C, 62.71; H, 5.91; N, 7.42.

EXAMPLE 8

N-[3-(7-Fluoro-1H-indol-3-yl)propyl]-N-(8-methyl-2,3-dihydro-[1,4]dioxino[2,3-f]quinolin-2-ylmethyl)amine To a mixture of [(2R)-8-methyl-2,3-dihydro[1,4]dioxino[2,3-f]quinolin-2-yl]methyl 4-bromobenzenesulfonate (1.01 g, 2.24 mmol) and 3-(7-fluoro-1H-indol-3-yl)-propylamine (0.81 g, 4.2 mmol) was added sodium carbonate (0.75 g, 7.1 mmol) and 4.5 mL of DMSO. The mixture was stirred at 108° C. for 18 hours. The solvent was evaporated at reduced pressure. The residue was partitioned between 500 mL each of ethyl acetate and water. The ethyl acetate layer was washed with water 3 times (250 mL) and dried over anhydrous magnesium sulfate. Evaporation of the solvent gave 1.36 g of oil. This was chromatographed on silica gel 0–10% methanol/ethyl acetate to give 0.42 g of the free base as an oil. This was dissolved in ethanol and added to a solution of fumaric acid (0.132 g, 1.14 mmol) in ethanol. Filtration gave 0.367 g of the (S)-enantiomer of the title compound as a white fumarate, m.p. 142–150° C.

Elemental Analysis for $C_{24}H_{24}FN_3O_2 \cdot C_4H_4O_4 \cdot H_2O$

Calc'd: C, 62.33; H, 5.60; N, 7.79. Found: C, 62.10; H, 5.55; N, 7.83.

EXAMPLE 9

N-[4-(1H-indol-3-yl)butyl]-N-(8-methyl-2,3-dihydro-[1,4]dioxino[2,3-f]quinolin-2-ylmethyl)amine To a mixture of [(2R)-8-methyl-2,3-dihydro[1,4]dioxino[2,3-f]quinolin-2-yl]methyl 4-bromobenzenesulfonate (0.87 g, 1.9 mmol) and 4-(1H-indol-3-yl)-butylamine (0.63 g, 3.3 mmol) was added sodium carbonate (0.63 g, 5.9 mmol) and 10 mL of DMSO. The mixture was stirred at 80° C. for 18 hours. The solvent was evaporated at reduced pressure. The residue was partitioned between 500 mL each of ethyl acetate and water. The ethyl acetate layer was washed with water (250 mL) 3 times and dried over anhydrous magnesium sulfate. Filtration and concentration in vacuum gave 1.02 g of oil. This was chromatographed on silica gel with gradient elution commencing with 1:1 ethyl acetate/hexane and ending with ethyl acetate to give 0.38 g of the free base as an oil. This was dissolved in ethanol and added to a solution of fumaric acid (0.115 g, 0.991 mmol) in ethanol. Filtration gave 0.336 g of the (S)-enantiomer of the title compound as white solid hemifumarate, m.p. 208–210° C.

Elemental Analysis for: $C_{25}H_{27}N_3O_2 \cdot 0.5\ C_4H_4O_4 \cdot 0.5\ H_2O$ Calc'd: C, 69.21; H, 6.45; N, 8.97. Found: C, 69.53; H, 6.47; N, 8.83.

EXAMPLE 10

N-[4-(5-Fluoro-1H-indol-3-yl)butyl]-N-(8-methyl-2,3-dihydro-[1,4]dioxino[2,3-f]quinolin-2-ylmethyl)amine To a mixture of [(2R)-8-methyl-2,3-dihydro[1,4]dioxino[2,3-f]quinolin-2-yl]methyl 4-bromobenzenesulfonate (1.63 g, 3.62 mmol) and 4-(5-fluoro-1H-indol-3-yl)-butylamine (1.39 g, 6.74 mmol) was added sodium carbonate (1.18 g, 1.11 mmol) and 8 mL of DMSO. The mixture was stirred at 105° C. for 8 hours. The solvent was evaporated at reduced pressure. The residue was partitioned between 500 mL each of ethyl acetate and water. The ethyl acetate layer was washed with water (250 mL) twice and dried over anhydrous magnesium sulfate. Filtration and concentration in vacuum gave 1.77 g of oil. This was chromatographed on silica gel with 0–10% methanol/ethyl acetate as eluant to give 0.42 g of the free base as an oil. This was dissolved in ethanol and added to a solution of fumaric acid (0.197 g, 1.70 mmol) in ethanol. Filtration gave 0.462 g of the (S)-enantiomer of the title compound as light yellow fumarate, m.p. 138–154° C.

Elemental Analysis for: $C_{25}H_{26}FN_3O_2 \cdot C_4H_4O_4 \cdot H_2O$

Calc'd: C, 62.92; H, 5.83; N, 7.59. Found: C, 62.63; H, 5.87; N, 7.42.

EXAMPLE 11

N-[4-(5-Fluoro-1H-indol-3-yl)-N-(8-methyl-2,3-dihydro-[1,4]dioxino[2,3-f]quinolin-2-ylmethyl)butan-2-amine Isomer A To a solution of 2S-C-(8-methyl-2,3-dihydro-[1,4]dioxino[2,3-f]quinolin-2-yl)-methylamine (0.70 g, 3.0 mmol) and 4-(5-fluoro-1H-indol-3-yl)-butan-2-one (0.66 g, 3.2 mmol) in 30 mL of dichloromethane was added acetic acid (0.35 mL, 0.37 g, 6.1 mmol) and sodium triacetoxyborohydride (0.97 g, 4.6 mmol). The reaction was stirred at room temperature for one day. The reaction mixture was shaken with 30 mL of 1 M NaOH. Water (30 mL) was added to this mixture and it was shaken again. The layers were separated and the aqueous layer was extracted once with 100 mL of methylene chloride. The organic layers were combined and dried over anhydrous magnesium sulfate. Evaporation of the solvent gave 1.49 g of tan oil. A small portion of this was eluted from a Chiralcel AD column with 90% EtOH and 10% hexane which contained 0.1% diethylamine to give as an oil 0.073 g of the first diastereomer to elute. This was dissolved in ethanol and added to a solution of fumaric acid (0.022 g, 0.19 mmol) in ethanol. Filtration gave 0.073 g of the fumarate of one diastereomer of the title compound as white solid, m.p. 145–154° C.

Elemental Analysis for: $C_{25}H_{26}FN_3O_2.C_4H_4O_4.0.3\ H_2O$

Calc'd: C, 64.39; H, 5.70; N, 7.77. Found: C, 64.38; H, 5.83; N, 7.51.

Isomer B

The separation of diastereomers in the last reaction also gave as an oil 0.042 g of the second diastereomer to elute. This was dissolved in ethanol and added to a solution of fumaric acid (0.013 g, 0.11 mmol) in ethanol. This didn't yield any crystals after prolonged standing. The residue after the solvent had been allowed to evaporate was scraped loose, stirred with EtOH and filtered to remove a lump of amorphous solid. Crystals formed in the ethanol solution. Filtration gave 0.017 g of the fumarate of the second diastereomer of the title compound as white solid, m.p. 146–156° C.

Elemental Analysis for: $C_{25}H_{26}FN_3O_2.C_4H_4O_4.H_2O$

Calc'd: C, 62.92; H, 5.83; N, 7.59. Found: C, 62.81; H, 5.81; N, 7.52.

EXAMPLE 12

N-[3-(5-Fluoro-1-methyl-1H-indol-3-yl)propyl]-N-(8-methyl-2,3-dihydro-[1,4]dioxino[2,3-f]quinolin-2-ylmethyl)amine To a mixture of [(2R)-8-methyl-2,3-dihydro[1,4]dioxino[2,3-f]quinolin-2-yl]methyl 4-bromobenzenesulfonate (2.29 g, 5.09 mmol) and 3-(-5-fluoro-1-methyl-1H-indol-3-yl)-propylamine (1.85 g, 8.97 mmol) was added sodium carbonate (1.57 g, 14.8 mmol) and 11 mL of DMSO. The mixture was stirred at 110° C. for 7 hours and then stirred at room temperature overnight. The solvent was evaporated at reduced pressure. The residue was partitioned between 500 mL each of ethyl acetate and water. The ethyl acetate layer was washed with water (250 mL) twice and dried over anhydrous magnesium sulfate. Filtration through Celite and concentration in vacuum gave 3.7 g of oil. This was chromatographed on silica gel 0–10% methanol/ethyl acetate to give 1.32 g of the free base as a yellow oil. This was dissolved in ethanol and added to a solution of fumaric acid (0.407 g, 3.51 mmol) in ethanol. Filtration gave 1.44 g of the (S)-enantiomer of the title compound as nearly white fumarate, m.p. 156–161° C.

Elemental Analysis for: $C_{25}H_{26}FN_3O_2.C_4H_4O_4.0.3\ H_2O$

Calc'd: C, 64.39; H, 5.70; N, 7.77. Found: C, 64.38; H, 5.73; N, 7.68.

EXAMPLE 13

N-[3-(5,7-Difluoro-1H-indol-3-yl)propyl]-N-(8-methyl-2,3-dihydro-[1,4]dioxino[2,3-f]quinolin-2-ylmethyl)amine To a mixture of [(2R)-8-methyl-2,3-dihydro[1,4]dioxino[2,3-f]quinolin-2-yl]methyl 4-bromobenzenesulfonate (2.10 g, 4.66 mmol) and 3-(5,7-difluoro-1H-indol-3-yl)-propylamine (1.72 g, 8.18 mmol) was added sodium carbonate (1.43 g, 13.5 mmol) and 20 mL of DMSO. The mixture was stirred at room temperature for 4 days. The solvent was evaporated at reduced pressure. The residue was partitioned between 500 mL of ethyl acetate and water. The ethyl acetate layer was washed with water (250 mL) twice and dried over anhydrous magnesium sulfate. Filtration and concetration in vacuum gave 2.18 g of oil. This was chromatographed on silica gel with 0–10% methanol/ethyl acetate as elusant to give 1.35 g of the free base as an oil. This was dissolved in ethanol and added to a solution of fumaric acid (0.124 g, 1.07 mmol) in ethanol. Filtration gave 0.506 g of the (S)-enantiomer of the title compound as white fumarate, m.p. 188–195° C.

Elemental Analysis for: $C_{24}H_{23}F_2N_3O_2.C_4H_4O_4.0.5\ C_2H_5OH$

Calc'd: C, 61.92; H, 5.37; N, 7.47. Found: C, 61.79; H, 5.46; N, 7.39.

EXAMPLE 14

N-(2,3-Dihydro-[1,4]dioxino[2,3-f]quinolin-2-ylmthyl)-N-[3-(5-fluoro-1H-indol-3-yl)propyl]amine A solution of (2R)-toluene4-sulfonic acid 2,3-dihydro-[1,4]dioxino[2,3-f]quinolin-2-ylmethyl ester (0.6 g, 1.6 mmol), 3-(5-fluoro-1H-indol-3-yl)propylamine (0.62 g, 3.2 mmol) and triethylamine (0.33 g, 3.2 mmol) in dimethylsulfoxide (20 mL) was heated at 90° C. under nitrogen for 9 hours. The reaction mixture was poured into water (100 mL) and extracted with methylene chloride (3×100 mL). The organic layer was washed with water (3×150 mL), dried over anhydrous sodium sulfate, filtered and the solvent was removed under vacuum. The crude oil was column chromatographed on silica gel (5% methanol/ethyl acetate). The product-containing fractions were concentrated in vacuum to give 0.31 g of the (S)-enantiomer of the title compound as a brown oil. The dihydrochloride salt was prepared in ethyl acetate as a yellow solid, m.p. 196–199° C.

Elemental Analysis for: $C_{23}H_{22}FN_3O_2.2\ HCl.H_2O$

Calc'd: C, 57.27; H, 5.43; N, 8.71. Found: C, 57.32; H, 5.47; N, 8.48.

EXAMPLE 15

N-(2,3-Dihydro-[1,4]dioxino[2,3-f]quinolin-2-ylmethyl)-N-[3-(5-fluoro-1H-indol-3-yl)propyl]-N-methylamine To a solution of (2S)-(2,3-dihydro-[1,4]dioxino[2,3-f]quinolin-2-ylmethyl)-[3-(5-fluoro-1H-indol-3-yl)-propyl]-amine (0.13 g, 0.33 mmol) and formaldehyde (37 wt. % in water, 0.26 g, 3.3 mmol) in methanol (20 mL) was added sodium cyanoborohydride (0.038 g, 0.59 mmol) and acetic acid (0.03 g, 0.5 mmol) at room temperature. The mixture was stirred at room temperature under nitrogen overnight, then quenched with 1N NaOH (5 mL). The mixture was extracted with methylene chloride (3×50 mL). The organic layer was washed with water (3×50 mL), dried over anhydrous sodium sulfate, filtered and the solvent was removed under vacuum. The crude oil was column chromatographed on silica gel (5% methanol-methylene chloride). The product-containing fractions were concentrated in vacuum to give 0.1 g of the (S)-enantiomer of the title compound as a brown oil. The dihydrochloride salt was prepared in ethyl acetate as a yellow solid (decomposed at 78° C.).

Elemental Analysis for: $C_{24}H_{24}FN_3O_2.2\ HCl.3.25\ H_2O$

Calc'd: C, 53.69; H, 6.10; N, 7.83. Found: C, 53.56; H, 6.16; N, 7.49.

EXAMPLE 16

N-[3-(5,7-Difluoro-1H-indol-3-yl)propyl]-N-methyl-N-(8-methyl-2,3-dihydro-[1,4]dioxino[2,3-f]quinolin-2-ylmethyl)amine To a solution of N-[3-(5,7-difluoro-1H-indol-3-yl)propyl]-N-{[(2S)-8-methyl-2,3-dihydro[1,4]dioxino[2,3-f]

quinolin-2-yl]methyl}amine (0.94 g, 2.2 mmol) in 4.3 mL of methanol was added paraformaldehyde (0.0844 g, 2.81 mmol). 4.3 mL of a stock solution of methanol/HCl (1 drop conc HCl in 16 mL of methanol) was added to adjust the pH to approximately 5. Sodium cyanoborohydride (0.225 g, 3.58 mmol) was added. The reaction was stirred at room temperature for 18 hours. One drop of concentrated HCl was added. The solvent was evaporated at reduced pressure. The residue was partitioned between 350 mL each of ethyl acetate and saturated aqueous sodium bicarbonate. The ethyl acetate layer was washed with water (200 mL) twice and saturated brine once. It was dried over anhydrous magnesium sulfate. Filtration and concentration in vacuum gave 1.00 g of crude residue. This was chromatographed on silica gel with gradient elution commencing with 1:1 ethyl acetate/hexane and ending with ethyl acetate to give 0.35 g of the free base as an oil. This was dissolved in ethanol and added to a solution of excess HCl in methanol. Filtration gave 0.343 g of the (S)-enantiomer of the title compound as a yellow dihydrochloride, m.p. dec. >240° C.

Elemental Analysis for: $C_{25}H_{25}F_2N_3O_2 \cdot 2$ HCl·0.2 $H_2O$

Calc'd: C, 58.42; H, 5.37; N, 8.17. Found: C, 58.50; H, 5.44; N, 8.13.

EXAMPLE 17

N-[2-(1-Benzofuran-3-yl) thyl]-N-(8-methyl-2,3-dihydro-]1,4]dioxino[2,3-f]quinolin-2-ylmethyl)amine To a stirred solution of 2-benzofuran-3-yl-ethylamine (390 mg, 2.42 mmol) in 3 mL of anhydrous DMSO was added [(2R)-8-methyl-2,3-dihydro[1,4]dioxino[2,3-f]quinolin-2-yl]methyl 4-bromobenzenesulfonate (363 mg, 0.807 mmol). The reaction mixture was heated to 50° C. overnight. The reaction was diluted with saturated aqueous sodium bicarbonate (10 mL) and extracted with ethyl acetate (3×10 mL). The combined organic layers were washed with brine (3×30 mL), dried over anhydrous magnesium sulfate, filtered, and concentrated in vacuum. Flash chromatography on $SiO_2$ (5% MeOH/$CH_2Cl_2$) afforded 252 mg (83%) of the (S)-enantiomer of the title compound as a yellow oil. The fumarate salt was prepared, yielding 280 mg of a yellow solid, m.p. 210–214° C.; MS (ESI) m/z 375 [M+H]$^+$.

Elemental Analysis for: $C_{23}H_{22}N_2O_3 \cdot 1.5$ $C_4H_4O_4$

Calc'd: C, 63.50; H, 5.15; N, 5.11. Found: C, 63.21; H, 5.19; N, 4.87.

EXAMPLE 18

N-[3-(1-Benzofuran-3-yl)propyl]-N-(8-methyl-2,3-dihydro-[1,4]dioxino2,3-f]quinolin-2-ylmethyl)amine To a stirred solution of 3-benzofuran-3yl-propylamine (700 mg, 4.34 mmol) in 6 mL of anhydrous DMSO was added [(2R)-8-methyl-2,3-dihydro[1,4]dioxino[2,3-f]quinolin-2-yl]methyl 4-bromobenzenesulfonate (652 mg, 1.45 mmol). The reaction mixture was heated to 50° C. overnight. The reaction was diluted with saturated aqueous sodium bicarbonate (10 mL) and extracted with ethyl acetate (3×10 mL). The combined organic layers were washed with brine (3×30 mL), dried over anhydrous magnesium sulfate, filtered, and concentrated in vacuum. Flash chromatography on $SiO_2$ (5% MeOH/$CH_2Cl_2$) afforded 510 mg (90%) of the (S)-enantiomer of the title compound as a yellow oil. The fumarate salt was prepared, yielding 93 mg of a yellow solid, m.p. 165–170° C.; MS (ESI) m/z 389 [M+H]$^+$.

Elemental Analysis for: $C_{24}H_{24}N_2O_3 \cdot C_4H_4O_4$

Calc'd: C, 66.66; H, 5.59; N, 5.55. Found: C, 64.56; H, 5.67; N, 5.05.

EXAMPLE 19

N-[3-(7-Methoxy-1-benzofuran-3-yl)propyl]-N-(8-methyl-2,3-dihydro-[1,4]dioxino[2,3-f]quinolin-2-ylmethyl)amine To a stirred solution of 3-(7-methoxy-benzofuran-3-yl)-propylamine (770 mg, 3.75 mmol) in 5 mL of anhydrous DMSO was added [(2R)-8-methyl-2,3-dihydro[1,4]dioxino[2,3-f]quinolin-2-yl]methyl 4-bromobenzenesulfonate (563 mg, 1.25 mmol). The reaction mixture was heated to 50° C. overnight. The reaction was diluted with saturated aqueous sodium bicarbonate (10 mL) and extracted with ethyl acetate (3×10 mL). The combined organic layers were washed with brine (3×30 mL), dried over anhydrous magnesium sulfate, filtered, and concentrated in vacuum. Flash chromatography on $SiO_2$ (5% MeOH/$CH_2Cl_2$) afforded 120 mg (23%) of the (S)-enantiomer of the title compound as a yellow oil. The fumarate salt was prepared, yielding 132 mg of a beige solid, m.p. 155–160° C.; MS (ESI) m/z 419 [M+H]$^+$.

Elemental Analysis for: $C_{25}H_{26}N_2O_4 \cdot C_4H_4O_4 \cdot 0.16$ $C_4H_8O_2 \cdot 0.09$ $H_2O$ Calc'd: C, 64.7; H, 5.76; N, 5.09. Found: C, 64.3; H, 5.55; N, 5.04.

EXAMPLE 20

N-[3-Benzothien-3-yl)propyl]-N-(8-methyl-2,3-dihydro-[1,4]dioxino[2,3-f]quinolin-2-ylmethyl)amine To a stirred solution of 3-benzo[b]thiophen-3-yl-propylamine (382 mg, 2.0 mmol) in 1 mL of anhydrous DMSO was added [(2R)-8-methyl-2,3-dihydro[1,4]dioxino[2,3-f]quinolin-2-yl]methyl 4-bromo-benzenesulfonate (300 mg, 0.67 mmol). The reaction mixture was heated at 40° C. for 18 hours. The reaction was diluted with $H_2O$ (10 mL), poured into saturated aqueous sodium bicarbonate (25 mL) and extracted with ethyl acetate (3×25 mL). The combined organic layers were washed with 1:1 $H_2O$/brine (40 mL) and brine (40 mL), then were dried over magnesium sulfate, filtered, and concentrated in vacuo. Flash chromatography (2×20 cm $SiO_2$, $CH_2Cl_2$ to 3% MeOH/$CH_2Cl_2$ gradient) afforded 221 mg (81%) of the (S)-enantiomer of the title compound as a thick gum. The fumarate salt was prepared by treating the amine in ethyl acetate with a solution of fumaric acid (63 mg, 0.54 mmol) in methanol. The precipitated salt weighed 238 mg (m.p. 185–186° C.); MS (ESI) m/z 405 [M+H]$^+$.

Elemental Analysis for: $C_{24}H_{24}N_2O_2S \cdot C_4H_4O_4$

Calc'd: C, 64.60; H, 5.42; N, 5.38. Found: C 64.29; H, 5.30; N, 5.23.

EXAMPLE 21

N-[2-(1-Benzothien-3-yl)ethyl]-N-(8-methyl-2,3-dihydro-[1,4]dioxino[2,3-f]quinolin-2-ylmethyl)amine To a stirred solution of 2-benzo[b]thiophen-3yl-ethylamine (354 mg, 2.0 mmol) in 1 mL of anhydrous DMSO was added [(2R)-8-methyl-2,3-dihydro[1,4]dioxino[2,3-f]quinolin-2-yl]methyl 4-bromo-benzenesulfonate (300 mg, 0.67 mmol). The reaction mixture was stirred at ambient temperature for 4 days. The reaction was diluted with $H_2O$ (10 mL), poured into saturated aqueous sodium bicarbonate (25 mL) and extracted with ethyl acetate (3×25 mL). The combined organic layers were washed with 1:1 $H_2O$/brine (40 mL) and brine (40 mL), then were dried over anhydrous magnesium sulfate, filtered, and concentrated in vacuum. Flash chromatography (2×20 cm $SiO_2$, $CH_2Cl_2$ to 3% MeOH/$CH_2Cl_2$ gradient) afforded 225 mg (86%) of the (S)-enantiomer of the title compound as a thick oil. The fumarate salt was prepared by treating the amine in ethyl acetate with a solution of 66 mg (0.57 mmol) fumaric acid in methanol. The precipitated salt, a pale yellow solid, weighed 190 mg (m.p. 124–127° C.); MS (ESI) m/z 391 [M+H]$^+$.

Elemental Analysis for: $C_{23}H_{22}N_2O_2S.C_4H_4O_4.0.50$ $H_2O$

Calc'd: C, 62.90; H, 5.28; N, 5.43. Found: C, 62.55; H, 5.23; N, 5.34.

EXAMPLE 22

N-[3-(1-Benzothien-3-yl)propyl]-N-methyl-N-(8-m thyl-2,3-dihydro-[1,4]dioxino[2,3-f]quinolin-2-ylm thyl)amin To a stirred solution of N-[3-(1-benzothien-3-yl)propyl]-N-{[(2S)-8-methyl-2,3-dihydro[1,4]dioxino[2,3-f]quinolin-2-yl]methyl}amine (340 mg, 0.84 mmol) in 5 ml of anhydrous THF was added formaldehyde (484 µL), acetic acid (96 µL, 1.68 mmol), and sodium triacetoxyborohydride (1,46 g, 6.9 mmol). The reaction mixture was stirred at ambient temperature for 3 days. The reaction was quenched with 1 M aqueous NaOH (10 mL), diluted with $H_2O$ (20 mL), made basic with more 1 M aqueous NaOH, and extracted with methylene chloride (3×40 mL). The combined organic layers were washed with brine (3×120 mL), dried over magnesium sulfate, filtered, and concentrated in vacuum. Flash chromatography on $SiO_2$ (5% MeOH/$CH_2Cl_2$) afforded 270 mg (77%) of the (S)-enantiomer of the title compound as a yellow oil. The fumarate salt was prepared, yielding 189 mg of a beige solid, m.p. 123–127° C.; MS (ESI) m/z 419 [M+H]$^+$.

Elemental Analysis for: $C_{25}H_{26}N_2O_2S.C_4H_4O_4.0.75$ $H_2O$

Calc'd: C, 63.55; H, 5.79; N, 5.11. Found: C, 63.40; H, 5.58; N, 4.81.

EXAMPLE 23

N-[3-(5-Fluoro-1H-indol-3-yl)propyl]-N-(2-methyl-7,8-dihydro-[1,4]dioxino[2,3-g][1,3]benzoxazol-8-ylmethyl)amine A solution of (2R)-toluene-4-sulfonic acid 2-methyl-7,8-dihydro-1,6,9-trioxa-3-aza-cyclopenta[a]-napthalen-8ylmethyl)-ester (0.4 g, 1.1 mmol), 3-(5-fluoro-1H-indol-3-yl)propylamine (0.41 g, 2.2 mmol) and triethylamine (0.29 g, 2.2 mmol) in dimethylsulfoxide (20 mL) was heated at 90° C. under nitrogen for 9 hours. The reaction mixture was poured into water (100 mL) and extracted with methylene chloride (3×80 mL). The organic layer was washed with water (3×100 mL), dried over anhydrous sodium sulfate, filtered and the solvent was removed under vacuum. The crude oil was column chromatographed on silica gel (5% methanol-methylene chloride). The product-containing fractions were concentrated in vacuum to give 0.14 g of the (S)-enantiomer of the title compound as a yellow oil. The hydrochloride salt was prepared in ethyl acetate as an off-white solid, m.p. 91–93° C.

Elemental Analysis for: $C_{22}H_{22}FN_3O_2O_2.1.5$ HCl.1.25 $H_2O$

Calc'd: C, 55.91; H, 5.54; N, 8.89. Found: C, 56.04; H, 5.74: N, 8.59.

EXAMPLE 24

N-[3-(5-Fluoro-1H-indol-3-yl)propyl]-N-methyl-N-(2-methyl-7,8-dihydro[1,4]dioxino[2,3-g][1,3]benzoxazol-8-ylmethyl)amine To a solution of [3-(5-fluoro-1H-indol-3-yl)-propyl]-(2-methyl-7,8-dihydro-1,6,9-trioxa-3-aza-cyclopenta[a] napthalen-8-ylmethyl)-amine (0.05 g, 0.13 mmol) and formaldehyde (37 wt. % in water, 0.1 g, 1.3 mmol) in methanol (10 mL) was added sodium cyanoborohydride (0.014 g, 0.23 mmol) and acetic acid (0.01 g, 0.26 mmol) at room temperature. The mixture was stirred at room temperature under nitrogen overnight, then quenched with 1N NaOH (5 mL). The mixture was extracted with methylene chloride (3×40 mL). The organic layer was washed with water (3×30 mL), dried over anhydrous sodium sulfate, filtered and the solvent was removed under vacuum. The crude oil was column chromatographed on silica gel (5% methanol-methylene chloride). The product-containing fractions were concentrated in vacuum to give 48 mg of the (S)-enantiomer of the title compound as a brown oil. The dihydrochloride salt was prepared in ethyl acetate as a white solid, m.p. 136–139° C.

Elemental Analysis for: $C_{23}H_{24}FN_3O_3.2$ HCl.$H_2O$

Calc'd: C, 55.21; H, 5.64; N, 8.40. Found: C, 55.40; H, 5.44; N, 8.29.

EXAMPLE 25

N-Ethyl-N-[3-(5-Fluoro-1H-indol-3-yl)propyl]-N-(8-methyl-2,3-dihydro-[1,4]dioxino[2,3-f]quinolin-2-ylmethyl)amine N-[3-(5-Fluoro-1H-indol-3-yl)propyl]-N-{[(2S)-8-methyl-2,3-dihydro[1,4]dioxino[2,3-f]quinolin-2-yl]methyl}amine (0.931 g, 2.30 mmol) was dissolved in 4.6 mL of methanol with heat. The solution was then cooled in an ice-bath. Acetaldehyde (0.20 mL, 0.16 g, 3.6 mmol) was added. 4.6 mL of a stock solution of HCl/methanol (one drop of conc HCl in 16 mL of methanol) was added to adjust the pH to approximately 5. Sodium cyanoborohydride (0.266 g, 4.23 mmol) was added. The reaction was stirred at room temperature and was complete in 4 hours. One drop of concentrated HCl was added. The solvent was evaporated at reduced pressure. The residue was partitioned between 350 mL each of ethyl acetate and saturated aqueous sodium bicarbonate. The ethyl acetate layer was washed with water (200 mL) twice and saturated brine once. It was dried over anhydrous magnesium sulfate. Filtration and concentration in vacuum gave 1.00 g of yellow oil. This was chromatographed on silica gel with gradient elution commencing with 1:1 ethyl acetate/hexane and ending with ethyl acetate to give 0.18 g of the free base as a clear colorless oil. Another 0.26 g was collected contaminated with one impurity. The pure portion was dissolved in ethanol and excess EtOH/HCl added. Filtration gave 0.075 g of the (S)-enantiomer of the title compound as a yellow dihydrochloride, m.p. 158–175° C.

Elemental Analysis for: $C_{26}H_{28}FN_3O_2.2$ HCl.1.5 $H_2O$

Calc'd: C, 58.54; H, 6.23; N, 7.88. Found: C, 58.55; H, 5.99; N, 7.56.

EXAMPLE 26

N-[3-(5,7-Difluoro-1-methyl-1H-indol-3-yl)propyl]-N-(8-methyl-2,3-dihydro-[1,4]dioxino[2,3-f]quinolin-2-ylmethyl)amine To a mixture of [(2R)-8-methyl-2,3-dihydro[1,4]dioxino[2,3-f]quinolin-2-yl]methyl 4-bromobenzenesulfonate (0.645 g, 1,43 mmol) and 3-(5,7-difluoro-1-methyl-1H-indol-3-yl)-propylamine (1.01 g, 4.50 mmol) was added sodium carbonate (0.66 g, 6.2 mmol) and 12 mL of DMSO. The mixture was stirred at 50° C. for 21 hours. The solvent was evaporated at reduced pressure. The residue was partitioned between 500 mL each of ethyl acetate and water. The ethyl acetate layer was washed with water (300 mL) twice and dried over anhydrous magnesium sulfate. Filtration and concentration in vacuum gave 1.60 g of oil. This was chromatographed on silica gel with 0–5% methanol in ethyl acetate to give 0.83 g of the free base as an oil. A 0.23 g portion was dissolved in ethanol. Saturated HCl/ethanol was added in excess. Filtration gave 0.204 g of the (S)-enantiomer of the title compound as a white solid dihydrochloride, m.p. dec. >239° C.

Elemental Analysis for: $C_{25}H_{25}F_2N_3O_2 \cdot 2$ HCl.1/3 $H_2O$

Calc'd: C, 58.15; H, 5.40; N, 8.14. Found: C, 58.09; H, 5.28; N, 8.01.

EXAMPLE 27

N-[3-(5,7-Difluoro-1-methyl-1H-indol-3-yl)propyl]-N-methyl-N-(8-methyl-2,3-dihydro-[1,4]dioxino[2,3-f]quinolin-2-ylmethyl)amine To 3-(5,7-difluoro-1-methyl-1H-indol-3-yl)-N-{[(2S)-8-methyl-2,3-dihydro[1,4]dioxino[2,3-f]quinolin-2-yl]methyl)propan-1-amine (0.57 g, 1.3 mmol) was added a warm suspension of paraformaldehyde (0.0625 g, 2.08 mmol) in 2,3 mL of methanol. 2,3 mL of a stock solution of HCl/methanol (one drop conc HCl in 16 mL of methanol) was added to adjust the pH to approximately 5. Sodium triacetoxyborohydride (0.48 g, 2.3 mmol) was added and the mixture was stirred at room temperature till the evolution of gas ceased. There was still starting material present. Excess HCl/methanol (2.3 mL) was added. NaBH₄ (0.42 g, 11 mmol) was added slowly. Sufficient methanol was added to allow efficient stirring. The reaction was stirred at room temperature for 1 day. HCl was added dropwise until no more gas was evolved. The solvent was evaporated in vacuum. The residue was partitioned between 500 mL each of ethyl acetate and saturated aqueous sodium bicarbonate. The ethyl acetate portion was washed with water (350 mL) twice. Drying over magnesium sulfate, filtration and evaporation of the solvent gave 0.65 g of oil. This was chromatographed on silica gel with a gradient of ethyl acetate and methanol to give 0.53 g of the free base as a colorless oil. This was dissolved in ethanol. An excess of saturated HCl/ethanol was added. Filtration gave 0.542 g of the (S)-enantiomer of the title compound as a yellow solid dihydrochloride, m.p. 190–204° C.

Elemental Analysis for: $C_{26}H_{27}F_2N_3O_2 \cdot 2$ HCl.1.25 $H_2O$

Calc'd: C, 57.10; H, 5.80; N, 7.68. Found: C, 57.05; H, 5.81; N, 7.59.

EXAMPLE 28

N-[4-(1-Benzofuran-3-yl)butyl]-N-(8-methyl-2,3-dihydro-[1,4]dioxino[2,3-f]quinolin-2-ylmethyl)amine To a stirred solution of 4-benzofuran-3-yl-butylamine (770 mg, 4.07 mmol) in 6 mL of anhydrous DMSO was added [(2R)-8-methyl-2,3-dihydro[1,4]dioxino[2,3-f]quinolin-2-yl]methyl 4-bromobenzenesulfonate (611 mg mg, 1.36 mmol). The reaction mixture was heated to 50° C. overnight. The reaction was diluted with saturated aqueous sodium bicarbonate (10 mL) and extracted with ethyl acetate (3×10 mL). The combined organic layers were washed with brine (3×30 mL), dried over anhydrous magnesium sulfate, filtered, and concentrated in vacuum. Flash chromatography on $SiO_2$ (5% $MeOH/CH_2Cl_2$) afforded 403 mg (74%) of the (S)-enantiomer of the title compound as a yellow oil. The fumarate salt was prepared, yielding 285 mg of a beige solid, m.p. 127–130° C.; MS (ESI) m/z 403 [M+H]⁺.

Elemental Analysis for: $C_{25}H_{26}N_2O_3 \cdot 0.8$ $C_4H_4O_4$

Calc'd: C, 68.38; H, 5.94; N, 5.66. Found: C, 68.06; H, 5.95; N, 6.04.

EXAMPLE 29

3-{3-[(8-Methyl-2,3-dihydro-[1,4]dioxino[2,3-f]quinolin-2-ylmethyl)-amino]-propyl}-1H-indole-5-carbonitrile A solution of (2R)-4-bromobenzenesulfonic acid 2,3-dihydro-[1,4]dioxino[2,3-f]quinolin-2-ylmethyl ester (1.13 g, 2.5 mmol), 3-(5-cyano-1H-indol-3-yl)propylamine (0.65 g, 3.2 mmol) and triethylamine (0.7 mL, 5.0 mmol) in dimethylsulfoxide (40 mL) was heated at 90° C. under nitrogen for 16 hours. The reaction mixture was quenched with 1N sodium hydroxide and extracted with methylene chloride (3×100 mL). The organic layer was washed with water (3×150 mL), dried over anhydrous sodium sulfate, filtered and the solvent was removed under vacuum. The crude oil was column chromatographed on silica gel (10% methanol-ethyl acetate). The product-containing fractions were concentrated in vacuum to give 0.54 g of the (S)-enantiomer of the title compound as a brown oil. The dihydrochloride salt was prepared in ethyl acetate as a yellow solid, m.p. 170–174° C.

Elemental Analysis for: $C_{25}H_{24}N_4O_2 \cdot 2$ HCl.1.75 $H_2O$

Calc'd: C, 58.09; H, 5.75; N, 10.84. Found: C, 58.00; H, 5.91; N, 10.82.

EXAMPLE 30

3-{3-[(2-Methyl-7,8-dihydro-[1,4]dioxino[2,3-g][1,3]benzoxazol-8-ylmethyl)amino]-propyl}-1H-indole-5-carbanitrile A solution of (2R)-toluene-4-sulfonic acid 2-methyl-7,8-dihydro-[1,6,9-trioxa-3-aza-cyclopenta[a]-napthalen-8-ylmethyl)-ester (1.0 g, 2.7 mmol), 3-(5-cyano-1H-indol-3-yl)propylamine (0.7 g, 3.5 mmol) and triethylamine (0.75 mL, 5.4 mmol) in dimethylsulfoxide (20 mL) was heated at 90° C. under nitrogen for 16 hours. The reaction mixture was quenched with 1N sodium hydroxide and extracted with methylene chloride (3×100 mL). The organic layer was washed with water (3×150 mL), dried over anhydrous sodium sulfate, filtered and the solvent was removed under vacuum. The crude oil was column chromatographed on silica gel (10% methanol-ethyl acetate). The product-containing fractions were concentrated in vacuum to give 0.56 g of the (S)-enantiomer of the title compound as a brown oil. The hydrochloride salt was prepared in ethyl acetate as an white solid, m.p. 148–151° C.

Elemental Analysis for: $C_{23}H_{22}N_4O_3 \cdot 1.5$ HCl.0.75 $H_2O$

Calc'd: C, 58.70; H, 5.35; N, 11.90. Found: C, 58.90; H, 5.72; N, 11.77.

EXAMPLE 31

3-{3-[M thyl-(2-methyl-7,8-dihydro-[1,4]dioxino[2,3[-g][1,3]benzoxazol-8-ylmethyl)-amino]-propyl)}-1H-indole-5-carbonitrile To a solution of [3-(5-fluoro-1H-indol-3-yl)-propyl]-(2-methyl-7,8-dihydro-1,6,9-trioxa-3-aza-cyclopenta[a]napthalen-8-ylmethyl)-amine (0.45 g, 0.11 mmol) and formaldehyde (37 wt. % in water, 0.9 g, 1.1 mmol) in methanol (20 mL) was added sodium cyanoborohydride (0.13 g, 0.2 mmol) and acetic acid (0.13 mL, 2.2 mmol) at room temperature. The mixture was stirred at room temperature under nitrogen overnight, then quenched with 1N NaOH (5 mL). The mixture was extracted with methylene chloride (3×60 mL). The organic layer was washed with water (3×60 mL), dried over anhydrous sodium sulfate, filtered and the solvent was removed under vacuum. The crude oil was column chromatographed on silica gel (5% methanol-ethyl acetate). The product-containing fractions were concentrated in vacuum to give 0.23 g of the (S)-enantiomer of the title compound as a brown oil. The hydrochloride salt was prepared in ethyl acetate as a white solid, m.p. 140° C. (d).

Elemental Analysis for: $C_{24}H_{24}N_4O_3.1.5\ HCl.H_2O$

Calc'd: C, 58.93; H, 5.67; N, 11.45. Found: C, 59.20; H, 5.90; N, 11.40.

EXAMPLE 32

3-{3-Methyl-(8-methyl-2,3-dihydro-[1,4]dioxino[2,3-f]quinolin-2-ylmethyl)-amino]propyl}-1H-indole-5-carbonitrile To a solution of (2S)-3-{3-[(8-methyl-2,3-dihydro-[1,4]dioxino[2,3-f]quinolin-2-ylmethyl)-amino]-proyl}-1H-indole-5-carbonitrile (0.2 g, 0.48 mmol) and formaldehyde (37 wt. % in water, 0.39 g, 4.8 mmol) in methanol (20 mL) was added sodium cyanoborohydride (0.05 g, 0.72 mmol) and acetic acid (0.06 mL, 0.96 mmol) at room temperature. The mixture was stirred at room temperature under nitrogen for 4 hours, then quenched with 1N NaOH (5 mL). The mixture was extracted with methylene chloride (3×60 mL). The organic layer was washed with water (3×50 mL), dried over anhydrous sodium sulfate, filtered and the solvent was removed under vacuum. The crude oil was column chromatographed on silica gel (5% methanol-ethyl acetate). The product-containing fractions were concentrated in vacuum to give 0.18 g of the (S)-enantiomer of the title compound as a brown oil. The dihydrochloride salt was prepared in ethyl acetate as a yellow solid (decomposed at 158° C.).

Elemental Analysis for: $C_{26}H_{26}N_4O_2.2\ HCl.3\ H_2O$

Calc'd: C, 56.42; H, 6.19; N, 10.12. Found: C, 56.15; H, 6.09; N, 9.89.

EXAMPLE 33

[3-(6-Fluoro-indol-1-yl)-propyl]-(8-methyl-2,3-dihydro-[1,4]dioxino[2,3-f]quinolin-2-ylmethyl)amine A solution of [(2R)-8-methyl-2,3-dihydro[1,4]dioxino[2,3-f]quinolin-2-yl]methyl 4-bromobenzenesulfonate (0.56 g, 1.2 mmol) in 35 mL of dimethyl sulfoxide and 0.35 mL of triethylamine was added to 3-(6-fluoro-indol-1-yl)-propylamine (0.6 g, 3.1 mmol). The mixture was heated under nitrogen at 90° C. for 4 hours. The mixture was cooled to room temperature, made basic with 1N sodium hydroxide and then extracted with 400 mL of methylene chloride. The methylene chloride phase was washed with 300 mL each of water and saturated brine, dried over magnesium sulfate, filtered and concentrated in vacuum. The residue was then column chromatographed on silica gel using first 3.5 L of 55% ethyl acetate/45% hexane to remove the impurities. The product was then eluted using 5% methanol in 95% methylene chloride. The product-containing fractions were then concentrated under vacuum to give 0.83 g of a light brown oil, which was dissolved in ethyl acetate and treated with excess hydrochloric acid in ether to give 0.050 g of the (S)-enantiomer of the title compound as a tan solid dihydrochloride, m.p. 154–156° C.

Elemental Analysis for: $C_{24}H_{24}FN_3O_2.3.25\ H_2O.2\ HCl$

Calc'd: C, 53.69; H, 6.10; N, 7.83. Found: C, 53.67; H, 5.81; N, 7.73.

EXAMPLE 34

[3-(6-Fluoro-indol-1-yl)-propyl]-methyl-(8-methyl-2,3-dihydro-[1,4]dioxino[2,3-f]quinolin-2-ylmethyl)-amine A solution of [3-(6-fluoro-indol-1-yl)-propyl]-[(2S)-8-methyl-2,3-dihydro-[1,4]dioxino[2,3-f]quinolin-2-ylmethyl]-amine (0.53 g, 1.3 mmol) in 1.05 mL of formaldehyde, 0.11 mL of acetic acid and 20 mL of methanol was added to 95% sodium cyanoborohydride (0.13 g, 1.9 mmole). The mixture was allowed to stir at room temperature under nitrogen overnight. The mixture was partitioned between 400 mL each of methylene chloride and water. The organic portion was washed with saturated brine, dried over magnesium sulfate, filtered and concentrated in vacuum. The residue was then column chromatographed on silica gel using 55% ethyl acetate/44% hexane/1% methanol as eluant. The product-containing fractions were concentrated under vacuum to give a yellow oil, which was dissolved in ethyl acetate and treated with excess HCl in ether to give 0.040 g of the (S)-enantiomer of the title compound as a yellow hydrochloride, m.p. 75.9–83.7° C.

Elemental Analysis for: $C_{25}H_{26}FN_3O_2.0.7\ H_2O.3.0\ HCl$

Calc'd: C, 55.31; H, 6.24; N, 7.74. Found: C, 55.56H, 5.95; N, 7.30.

EXAMPLE 35

[4-(5-Fluoro-1-methyl-1H-indol-3-yl)-butyl]-(8-methyl-2,3-dihydro-[1,4]dioxino[2,3-f]quinolin-2-ylmethyl)-amine To a mixture of [(2R)-8-methyl-2,3-dihydro[1,4]dioxino[2,3-f]quinolin-2-yl]methyl 4-bromobenzenesulfonate (3.69 g, 8.19 mmol) and 4-(5-fluoro-1-methyl-1H-indol-3-yl)-butylamine (2.21 g, 10.0 mmol) was added sodium carbonate (2.47 g, 23.3 mmol) and 20 mL of DMSO. The mixture was stirred at room temperature for 4 days. The solvent was evaporated at reduced pressure. The residue was partitioned between 500 mL each of ethyl acetate and water. The ethyl acetate layer was washed with water (250 mL) 3 times and dried over anhydrous magnesium sulfate. Filtration and concentration in vacuum gave 3.49 g of oil. This was chromatographed on silica gel with 0–10% methanol/ethyl acetate to give 1.29 g of the free base as a clear, colorless oil. A 0.49 g portion was dissolved in ethanol. An excess of saturated HCl/ethanol was added. Filtrabon gave 0.256 g of the (S)-enantiomer of the title compound as a yellow dihydrochloride, m.p. 229–235° C.

Elemental Analysis for: $C_{26}H_{28}FN_3O_2.2\ HCl.0.9\ H_2O$

Calc'd: C, 59.75; H, 5.96; N, 8.04. Found: C, 59.71; H, 6.17; N, 7.93.

EXAMPLE 36

Ethyl-[3-(5-fluoro-1H-indol-3-yl)-propyl]-(2-methyl-7,8-dihydro-[1,4]dioxino[2,3-g][1,3]benzoxazol-8-ylmethyl)-amine To a solution of [3-(5-fluoro-1H-indol-3-yl)-propyl]-(2-methyl-7,8-dihydro-1,6,9trioxa-3-aza-cyclopenta[a]

napthalen-8-ylmethyl)-amine (0.13 g, 0.32 mmol) and acetaldehyde (0.18 mL, 3.2 mmol) in methanol (20 mL) was added sodium cyanoborohydride (0.07 g, 0.57 mmol) and acetic acid (0.04 mL, 0.32 mmol) at room temperature. The mixture was stirred at room temperature under nitrogen overnight, then quenched with 1N NaOH (5 mL). The mixture was extracted with methylene chloride (3×50 mL). The organic layer was washed with water (3×50 mL), dried over anhydrous sodium sulfate, filtered and the solvent was removed under vacuum. The crude oil was column chromatographed on silica gel (5% methanol-methylene chloride). The product-containing fractions were concentrated in vacuum to give 145 mg of the (S)-enantiomer of the title compound as a yellow oil. The dihydrochloride salt was prepared in ethyl acetate as a white solid, m.p. 115° C. d.

Elemental Analysis for: $C_{24}H_{24}FN_3O_3.2$ HCl.0.25 $H_2O$

Calc'd: C, 57.55; H, 5.73; N, 8.39. Found: C, 57.83; H, 5.76; N, 8.28.

EXAMPLE 37

1-Methyl-3-{3-[(8-methyl-2,3-dihydro-[1,4]dioxino [2,3-f]quinolin-2-ylmethyl)-amino]-proyl}-1H-indole-5-carbonitrile A solution of (2R)-4-bromobenzenesulfonic acid-8-methyl-2,3-dihydro-[1,4]dioxino[2,3-f]quinolin-2-ylmethyl ester (0.5 g, 1.1 mmol), 3-(5-cyano-1-methyl-indol-3-yl) propylamine (0.33 g, 1,4 mmol) and triethylamine (0.23 mL, 2.2 mmol) in dimethylsulfoxide (20 mL) was heated at 90° C. under nitrogen for 16 hours. The reaction mixture was quenched with 1N sodium hydroxide and extracted with methylene chloride (3×100 mL). The organic layer was washed with water (3×150 mL), dried over anhydrous sodium sulfate, filtered and the solvent was removed under vacuum. The crude oil was column chromatographed on silica gel (10% methanol-ethyl acetate). The product-containing fractions were concentrated in vacuum to give 0.2 g of the (S)-enantiomer of the title compound as a brown oil. The dihydrochloride salt was prepared in ethyl acetate as a yellow solid (decomposed at 148° C.).

Elemental Analysis for: $C_{26}H_{26}N_4O_2.2$ HCl.2.75 $H_2O$

Calc'd: C, 56.88; H, 6.15; N, 10.21. Found: C, 56.72; H, 5.93; N, 10.08.

EXAMPLE 38

[4-(6-Fluoro-indol-1-yl)-butyl]-(8-methyl-2,3-dihydro-[1,4]dioxino[2,3-f]quinolin-2-ylmethyl)-amine A solution of [(2R)-8-methyl-2,3-dihydro[1,4]dioxino[2, 3-f]quinolin-2-yl]methyl 4-bromobenzenesulfonate (1.57 g, 3.5 mmol) in 105 mL of dimethyl sulfoxide and 0.97 mL of triethylamine was added to 4-(6-fluoro-indol-1-yl)-butylamine (1.8 g, 7.3 mmol). The mixture was heated under nitrogen at 90° C. for 4 hours. The mixture was cooled to room temperature, made basic with 1N sodium hydroxide and then extracted with 400 mL of methylene chloride. The organic portion was washed with 300 mL each of water and saturated brine, dried over magnesium sulfate, filtered and concentrated in vacuum. The residue was column chromatographed on silica gel using first 55% ethyl acetate/44% hexane (1% methanol to wash off some impurities and then 5% methanol/methylene chloride to elute the product off the column. The product-containing fractions were then concentrated under vacuum to give 0.225 g of a yellow oil. The oil was dissolved in ethyl acetate and treated with excess ethereal HCl to give 0.060 g of the (S)-enantiomer of the title compound as a yellow dihydrochloride, m.p. 122–127° C.

Elemental Analysis for: $C_{25}H_{26}FN_3O_2.2$ HCl.0.50 $H_2O$

Calc'd: C, 59.88; H, 5.83; N, 8.38. Found: C, 59.55; H, 5.87; N, 8.05.

EXAMPLE 39

3-{4-[(8-Methyl-2,3-dihydro-[1,4]dioxino[2,3-f] quinolin-2-ylm thyl)-amino]-butyl}-1H-indole-5-carbonitrile A solution of (2R)-4-bromobenzenesulfonic acid 8-methyl-2,3-dihydro-[1,4]dioxino[2,3-f]quinolin-2-ylmethyl ester (0.84 g, 1.8 mmol), 3-(5-cyano-1H-indol-3-yl)butylamine (0.6 g, 2.8 mmol) and triethylamine (0.52 mL, 3.6 mmol) in dimethylsulfoxide (40 mL) was heated at 90° C. under nitrogen overnight. The reaction mixture was quenched with 1N sodium hydroxide and extracted with methylene chloride (3×100 mL). The organic layer was washed with water (3×150 mL), dried over anhydrous sodium sulfate, filtered and the solvent was removed under vacuum. The crude oil was column chromatographed on silica gel (10% methanol-ethyl acetate). The product-containing fractions were concentrated in vacuum to give 0.25 g of the (S)-enantiomer of the title compound as a brown oil. The dihydrochloride salt was prepared in ethyl acetate as a yellow solid (decomposed at 105° C.).

Elemental Analysis for: $C_{26}H_{26}N_4O_2.2$ HCl.2.25 $H_2O$

Calc'd: C, 57.83; H, 6.07; N, 10.38. Found: C, 57.81; H, 5.93; N, 10.34.

EXAMPLE 40

1-Methyl-3-{3-[methyl-(8-methyl-2,3-dihydro-[1,4] dioxino[2,3-f]quinolin-2-ylmethyl)-amino]-propyl}-1H-indole-5-carbonitrile To a solution of (2S)-1-methyl-3-{3-[(8-methyl-2,3-dihydro-[1,4]dioxino[2,3-f]quinolin-2-ylmethyl)-amino]-proyl}-1H-indole-5-carbonitrile (0.1 g, 0.23 mmol) and formaldehyde (37 wt. % in water, 0.19 g, 2.3 mmol) in methanol (20 mL) was added sodium cyanoborohydride (0.026 g, 0.41 mmol) and acetic acid (0.027 mL, 0.46 mmol) at room temperature. The mixture was stirred at room temperature under nitrogen for 2 hours, then quenched with 1N NaOH (5 mL). The mixture was extracted with methylene chloride (3×50 mL). The organic layer was washed with water (3×50 mL), dried over anhydrous sodium sulfate, filtered and the solvent was removed under vacuum. The crude oil was column chromatographed on silica gel (5% methanol-ethyl acetate). The product-containing fractions were concentrated in vacuum to give 0.1 g of the (S)-enantiomer of the title compound as a brown oil. The dihydrochloride salt was prepared in ethyl acetate as a yellow solid (decomposed at 165° C.).

Elemental Analysis for: $C_{27}H_{28}N_4O_2.2$ HCl.4 $H_2O$

Calc'd: C, 55.39; H, 6.54; N, 9.57. Found: C, 55.51; H, 6.35; N, 9.57.

EXAMPLE 41

3-{4-[Methyl-(8-methyl-2,3-dihydro-[1,4]dioxino[2, 3-f]quinolin-2-ylmethyl)-amino]-butyl}-1H-indole-5-carbonitrile To a solution of (2S)-3-{4-[(8-methyl-2,3-dihydro-[1,4] dioxino[2,3-f]quinolin-2-ylmethyl)-amino]-butyl}-1H- indole-5-carbonitrile (0.13 g, 0.30 mmol) and formaldehyde (37 wt. % in water, 0.24 g, 3.0 mmol) in methanol (20 mL) was added sodium cyanoborohydride (0.35 g, 0.54 mmol) and acetic acid (0.035 mL, 0.6 mmol) at room temperature. The mixture was stirred at room temperature under nitrogen for 4 hours, then quenched with 1N NaOH (5 mL). The mixture was extracted with methylene chloride (3×50 mL). The organic layer was washed with water (3×50 mL), dried over anhydrous sodium sulfate, filtered and the solvent was removed under vacuum. The crude oil was column chromatographed on silica gel (5% methanol-ethyl acetate). The product-containing fractions were concentrated in vacuum to give 0.11 g of the (S)-enantiomer of the title compound as a brown oil. The dihydrochloride salt was prepared in ethyl acetate as a yellow solid (decomposed at 155° C.).

Elemental Analysis for: $C_{27}H_{28}N_4O_2 \cdot 2$ HCl.3 $H_2O$

Calc'd: C, 57.14; H, 6.39; N, 9.87. Found: C, 57.35; H, 6.37; N, 9.76.

EXAMPLE 42

[3-(5-Fluoro-1-methyl-1H-indol-3-yl)-propyl]-methyl-(8-methyl-2,3-dihydro-[1,4]dioxino[2,3-f]quinolin-2-ylmethyl)-amine To a solution of N-[3-(5-fluoro-1-methyl-1H-indol-3-yl)propyl]-N-{[(2S)-8-methyl-2,3-dihydro[1,4]dioxino[2,3-f]quinolin-2-yl]methyl}amine (1.05 g, 2.50 mmol) in 100 mL of methanol was added an aqueous 37% formaldehyde solution (2 mL, 0.8 g, 30 mmol). Acetic acid (0.2 mL, 0.2 g, 3 mmol) and then sodium cyanoborohydride (0.28 g, 4.5 mmol) were added. The reaction was stirred at room temperature for 3 hours. No amine starting material remained. One drop of concentrated HCl was added. The mixture was allowed to stir for 2 days. The solvent was evaporated at reduced pressure. The residue was partitioned between 500 mL each of ethyl acetate and water. The ethyl acetate layer was washed with water (250 mL) twice. Saturated brine was added as needed to break up the emulsion. Drying over anhydrous magnesium sulfate, filtration and evaporation of the solvent gave 1.08 g of oil. This was chromatographed on silica gel with gradient elution commencing with 1:1 ethyl acetate/hexane and ending with ethyl acetate to give 0.85 g of the free base as a colorless and almost pure oil. This was dissolved in ethanol. An excess of saturated HCl/ethanol was added. Filtration gave 0.316 g of the (S)-enantiomer of the title compound as a yellow solid dihydrochloride, m.p. 274–275° C.

Elemental Analysis for: $C_{26}H_{28}FN_3O_2 \cdot 2$ HCl

Calc'd: C, 61.66; H, 5.97; N, 8.30. Found: C, 62.26; H, 5.93; N, 8.21.

EXAMPLE 43

[4-(5-Fluoro-1H-indol-3-yl)-butyl]-methyl-(8-methyl-2,3-dihydro-[1,4]dioxino[2,3-f]quinolin-2-ylmethyl}-amine To a mixture of N-[4-(5-fluoro-1H-indol-3-yl)butyl]-N-{[(2S)-8-methyl-2,3-dihydro[1,4]dioxino[2,3-f]quinolin-2-yl]methyl}amine (0.87 g, 2.1 mmol) and N-[4-(5-fluoro-1H-indol-3-yl)butyl]-N-{[(2S)-8-methyl-2,3-dihydro[1,4]dioxino[2,3-f]quinolin-2-yl]methyl}amine dihydrochloride (0.46 g, 9.3 mmol) in 100 mL of methanol was added an aqueous 37% formaldehyde solution (2,39 mL, 0.964 g, 32.1 mmol). Acetic acid (0.1 mL, 0.1 g, 2 mmol) and then sodium cyanoborohydride (0.25 9, 4.0 mmol) were added. The reaction was stirred at room temperature for 18 hours. The solvent was evaporated at reduced pressure. The residue was partitioned between 500 mL each of ethyl acetate and water. The ethyl acetate layer was washed with water (250 mL) 3 times. Drying over anhydrous magnesium sulfate, filtration and evaporation of the solvent gave 1.64 g of oil. This was chromatographed on silica gel with gradient elution commencing with 1:1 ethyl acetate/hexane and ending with ethyl acetate to give 0.86 g of the free base as a colorless oil. This was dissolved in ethanol. An excess of saturated HCl/ethanol was added. Filtration gave 0.771 g of the (S)-enantiomer of the title compound as a yellow solid dihydrochloride, m.p. 274–275° C.

Elemental Analysis for: $C_{26}H_{28}FN_3O_2 \cdot 2$ HCl.0.5 $H_2O$

Calc'd: C, 60.58; H, 6.06; N, 8.15. Found: C, 60.78; H, 5.84; N, 7.95.

EXAMPLE 44

[4-(5-Fluoro-1-methyl-1H-indol-3-yl)-butyl]-methyl-(8-methyl-2,3-dihydro-[1,4]dioxino[2,3-f]quinolin-2-ylmethyl)-amine To a solution of N-[4-(5-fluoro-1H-indol-3-yl)butyl]-N-{[(2S)-8-methyl-2,3-dihydro[1,4]dioxino[2,3-f]quinolin-2-yl]methyl}amine (0.83 g, 2.0 mmol) in 79 mL of methanol was added an aqueous 37% formaldehyde solution (1.6 mL, 0.65 g, 21 mmol). Acetic acid (1.5 mL, 1.6 g, 26 mmol) and then sodium cyanoborohydride (0.22 g, 3.5 mmol) were added. The reaction was stirred at room temperature for 5 days. Only a trace of amine starting material remained. The solvent was evaporated at reduced pressure. The residue was partitioned between 500 mL each of ethyl acetate and water. The ethyl acetate layer was washed with water (250 mL) twice. Drying over anhydrous magnesium sulfate, filtration and evaporation of the solvent gave 0.79 g of oil. This was chromatographed on silica gel with ethyl acetate and then 2.5% methanol in ethyl acetate to give 0.74 g of the free base as an oil. This was dissolved in ethanol. An excess of saturated HCl/ethanol was added. Filtration gave 0.760 g of the (S)-enantiomer of the title compound as a yellow solid dihydrochloride, m.p. 275–276° C.

Elemental Analysis for: $C_{27}H_{30}FN_3O_2 \cdot 2$ HCl

Calc'd: C, 62.31; H, 6.20; N, 8.07. Found: C, 62.11; H, 6.04; N, 7.93.

EXAMPLE 45

[3-(5-Fluoro-1H-indol-3-yl)-propyl]-(8-methyl-2,3-dihydro-[1,4]dioxino[2,3-f]quinolin-2-ylmethyl)-propyl-amine To a solution of N-[3-(5-fluoro-1H-indol-3-yl)propyl]-N-{[(2S)-8-methyl-2,3-dihydro[1,4]dioxino[2,3-f]quinolin-2-yl]methyl}amine (0.39 g, 0.96 mmol) in 4.9 mL of methanol was added propionaldehyde (0.15 mL, 0.12 g, 2.1 mmol). 4.9 mL of a stock solution of HCl/methanol (one drop conc HCl in 16 mL of methanol) was added to adjust the pH to approximately 5. Sodium cyanoborohydride (0.12 g, 1.9 mmol) was added. The reaction was stirred at room temperature and was complete in 3 hours. One drop of concentrated HCl was added. The mixture was stirred overnight. The solvent was evaporated at reduced pressure. The residue was partitioned between 500 mL each of ethyl acetate and water. The ethyl acetate layer was washed with water (250 mL) twice. Saturated brine was added as needed to break up the emulsion. Drying over anhydrous magnesium sulfate, filtration and evaporation of the solvent gave 0.39 g of yellow oil. This was chromatographed on silica gel with gradient elution commencing with 1:1 ethyl acetate/hexane and ending with ethyl acetate to give 0.27 g of the free base as a clear oil. This was dissolved in ethanol. An excess of saturated HCl/ethanol was added. Filtration gave 0.234 g of the (S)-enantiomer of the title compound as a yellow solid dihydrochloride, m.p. 164–170° C.

Elemental Analysis for: $C_{27}H_{30}FN_3O_2.2$ HCl.2.75 $H_2O$

Calc'd: C, 56.89; H, 6.63; N, 7.37. Found: C, 56.81; H, 6.35; N, 7.29.

EXAMPLE 46

[3-(4-Fluoro-indol-1-yl)-propyl]-(8-methyl-2,3-dihydro-[1,4]dioxino[2,3-f]quinolin-2-ylmethyl)-amine A solution of [(2R)-8-methyl-2,3-dihydro[1,4]dioxino[2,3-f]quinolin-2-yl]methyl 4-bromobenzenesulfonate_(1.56 g, 3.5 mmol) in 97.5 mL of dimethyl sulfoxide and 0.97 mL of triethylamine was added to 3-(4-fluoro-indol-1-yl)-propylamine (1.67 g, 8.7 mmol). The mixture was heated under nitrogen at 90° C. for 5 hours. The mixture was cooled to room temperature, made basic with 1N sodium hydroxide and then diluted with 400 mL of methylene chloride. The mixture was washed with 300 mL portions of water and saturated brine, dried over magnesium sulfate, filtered and concentrated in vacuum. The residue was column chromatographed on silica gel using 70% ethyl acetate/25% hexane/5% methanol to elute the product off the column. The product-containing fractions were then combined and concentrated under vacuum to give a clear oil. The oil was dissolved in ethyl acetate and treated with excess ethereal HCl to give 0.088 g of the (S)-enantiomer of the title compound as a white hydrochloride, m.p. 203–206° C.

Elemental Analysis for: $C_{24}H_{24}FN_3O_2.HCl.0.25$ $H_2O$

Calc'd: C, 53.66; H, 5.43; N, 7.45. Found: C, 53.67; H, 5.81; N, 7.73.

EXAMPLE 47

[4-(6-Fluoro-indol-1-yl)-butyl]-methyl-(8-methyl-2,3-dihydro-[1,4]dioxino[2,3-f]quinolin-2-ylmethyl)-amine A solution of [4-(6-fluoro-indol-1-yl)-butyl]-[(2S)-8-methyl-2,3-dihydro-[1,4]dioxino[2,3-f]quinolin-2-ylmethyl]-amine (0.23 g, 0.5 mmol) in 0.45 mL of formaldehyde, 0.05 mL of acetic acid and 10 mL of methanol was added to 95% sodium cyanoborohydride (0.05 g, 0.5 mmol). The mixture was allowed to stir at room temperature under nitrogen for 4.5 hours. The mixture was partitioned between 400 mL each of ethyl acetate and water. The organic portion was washed with saturated brine, dried over magnesium sulfate, filtered and concentrated in vacuum. The residue was column chromatographed on silica gel using 15% methanol in ethyl acetate as eluant. The product-containing fractions were concentrated under vacuum to give a yellow oil. The oil was dissolved in ethyl acetate and treated with excess ethereal HCl to give 0.40 g of the (S)-enantiomer of the title compound as a yellow solid dihydrochloride, m.p. 182–188° C.

Elemental Analysis for: $CH_{26}H_{28}FN_3O_2.2.0$ HCl.3.0 $H_2O$

Calc'd: C, 55.72; H, 5.47; N, 7.50. Found: C, 53.67; H, 6.07; N, 7.46.

EXAMPLE 48

[3-(4-Fluoro-indol-1-yl)-propyl]-methyl-(8-methyl-2,3-dihydro-[1,4]dioxino2,3-f]quinolin-2-ylmethyl)-amine A solution of [3-(4-fluoro-indol-1-yl)-propyl]-(8-methyl-2,3-dihydro-[1,4]dioxino[2,3-f]quinolin-2-ylmethyl)-amine (0.19 g, 0.5 mmol) in 0.71 mL of formaldehyde, 0.07 mL of acetic acid and 18 mL of methanol was added to 95% sodium cyanoborohydride (0.09 g, 1.3 mmol). The mixture was allowed to stir at room temperature under nitrogen for 4 hours. The mixture was diluted to 400 mL with methylene chloride, washed with 300 mL each of water and saturated brine, dried over magnesium sulfate, filtered and concentrated in vacuum to a yellow oil. The residue was column chromatographed on silica gel using 75% ethyl acetate and 25% hexane as eluant. The product-containing fractions were concentrated under vacuum to give a yellow oil and the oil was dissolved in ethyl acetate and treated with excess ethereal HCl to give 0.060 g of the (S)-enantiomer of the title compound as a yellow dihydrochloride, m.p. 125–137° C.

Elemental Analysis for: $C_{24}H_{24}FN_3O_2.2.0$ HCl.1.0 $H_2O.0.2$ $C_4H_8O_2$ Calc'd: C, 58.75; H, 5.98; N, 8.09. Found: C, 58.78; H, 5.91; N, 8.04.

EXAMPLE 49

N-[4[(5-Chloro-1-b nzothl n-3-yl)butyl]-N-{[(2S)-8-m thyl-2,3-dihydro[1,4]dioxino[2,3-f]quinolin-2-yl]methyl}amine A mixture of [(2R)-8-methyl-2,3-dihydro[1,4]dioxino[2,3-f]quinolin-2-yl]methyl 4-bromobenzenesulfonate (250 mg, 0.556 mmol) and 4-(5-chloro-benzo[b]thiophen-3-yl)-butylamine (400 mg, 1.67 mmol) in anhydrous dimethylsulfoxide (3 mL) was heated at 40° C. for three days. The cooled reaction was diluted with saturated aqueous sodium bicarbonate (20 mL) and extracted with ethyl acetate (3×20 mL). The combined organic layers were washed with brine (30 mL), dried over anhydrous sodium sulfate, filtered, and concentrated in vacuo. Flash chromatography on silica gel (3/97 2 M ammonia in methanol/methylene chloride) did not provide clean product. Re-chromatography on silica gel (90/5/5 ethyl acetate/hexane/triethylamine) afforded 236 mg (94%) of the title compound as a yellow viscous oil, which was converted to its fumarate salt as a yellow solid: mp 140–144° C.; MS (ES) m/z 453 [M+H]$^+$; $[\alpha]_D$ −28.9° (c 1.0, DMSO).

Elemental Analysis for: $C_{25}H_{25}ClN_2O_2S.C_4H_4O_4.0.1$ $C_4H_8O_2.H_2O$

Calc'd: C, 59.26; H, 5.38; N, 4.70. Found: C, 59.05; H, 5.07; N, 4.35.

EXAMPLE 50

N-[3-(5-Chloro-1-benzothien-3-yl)propyl]-N-{[(2S)-8-methyl-2,3-dihydro[1,4]dioxino[2,3-f]quinolin-2-yl)]methyl}amine A mixture of [(2R)-8-methyl-2,3-dihydro[1,4]dioxino[2,3-f]quinolin-2-yl]methyl 4-bromobenzenesulfonate (406 mg, 0.90 mmol) and 3-(5-chloro-benzo[b]thiophen-3-yl)-propylamine (610 mg, 2.7 mmol) in anhydrous dimethylsulfoxide (4 mL) was heated at 40° C. overnight. The cooled reaction was diluted with saturated aqueous sodium bicarbonate (25 mL) and extracted with ethyl acetate (3×25 mL). The combined organic layers were washed with brine (40 mL), dried over anhydrous sodium sulfate, filtered, and concentrated in vacuo. Flash chromatography on silica gel (3/2/95-methanol/2 M ammonia in methanol/methylene chloride) afforded 340 mg (86%) of the title compound as a yellow viscous oil, which was converted to its fumarate salt as a yellow solid: mp 193–196° C.; MS (ES) m/z 439 [M+H]$^+$; $[\alpha]_D$ −26.9° (c 1.0, DMSO)

Elemental Analysis for: $C_{24}H_{23}ClN_2O_2S \cdot C_4H_4O_4 \cdot 0.7$ $C_4H_8O_2 \cdot H_2O$ Calc'd: C, 58.28; H, 5.49; N, 4.41. Found: C, 57.91; H, 5.28; N, 4.44.

EXAMPLE 51

N-[3-(5-Fluoro-1-benzothien-3-yl)propyl]-N-{[(2S)-8-methyl-2,3-dihydro[1,4]dioxino[2,3-f]quinolin-2-yl]methyl}amine A mixture of [(2R)-8-methyl-2,3-dihydro[1,4]dioxino[2,3-f]quinolin-2-yl]methyl 4-bromobenzenesulfonate (151 mg, 0.669 mmol) and 3-(5-fluoro-benzo[b]thiophen-3-yl)-propylamine (140 mg, 0.335 mmol) in anhydrous dimethylsulfoxide (7 mL) was stirred at ambient temperature for three days without any apparent reaction occurring. The reaction was then heated at 40° C. for two days, resulting in complete conversion. The cooled reaction was diluted with saturated aqueous sodium bicarbonate (35 mL) and extracted with ethyl acetate (3×35 mL). The combined organic layers were washed with brine (40 mL), dried over anhydrous sodium sulfate, filtered, and concentrated in vacua. Flash chromatography on silica gel (2/2/96 methanol/2 M ammonia in methanol/methylene chloride) afforded 90 mg (63%) of the title compound as a yellow viscous oil, which was converted to its fumarate salt as a yellow solid: mp 117–120° C.; MS (ES) m/z 423 [M+H]$^+$; [α]$_D$ −29.1° (c 0.94, DMSO)

Elemental Analysis for: $C_{24}H_{23}FN_2O_2S \cdot C_4H_4O_4 \cdot 0.5$ $H_2O$

Calc'd: C, 61.41; H, 5.15; N, 5.12. Found: C, 61.07; H, 5.03; N, 4.89.

EXAMPLE 52

N-[4-(1-Benzofuran-3-yl)butyl]-N-ethyl-N-{[(2S)-8-methyl-2,3-dihydro[1,4]dioxino[2,3-f]quinolin-2-yl]methyl}amine To a solution of N-[3-(1-benzofuran-3-yl)propyl]-N-{[(2S)-8-methyl-2,3-dihydro-[1,4]dioxino[2,3-f]quinolin-2-yl]methyl}amine (206 mg, 0.512 mmol) in anhydrous tetrahydrofuran (3 mL) was added acetaldehyde (206 μL, 3.67 mmol), sodium triacetoxyborohydride (445 mg, 2.1 mmol), and glacial acetic acid (41 μL, 0.716 mmol). The reaction was allowed to stir at ambient temperature overnight, then was quenched with 1 M aqueous sodium hydroxide (5 mL) and diluted with water (10 mL). The aqueous mixture was extracted with methylene chloride (3×25 mL). The combined organic layers were washed with brine (50 mL), dried over anhydrous sodium sulfate, filtered, and concentrated in vacuo. Flash chromatography on silica gel (50/45/5 ethyl acetate/hexane/triethylamine) afforded 120 mg (55%) of the title compound as an orange oil, which was converted to its fumarate salt as a brown solid: mp 87–92° C.; MS (ES) m/z 431 [M+H]$^+$; [α]$_D$ −8.58° (c 1.0, DMSO).

Elemental Analysis for: $C_{27}H_{30}N_2O_3 \cdot 1.3$ $C_4H_4O_4 \cdot 0.7$ $H_2O$ Calc'd: C, 65.10; H, 6.21; N, 4.72. Found: C, 65.56; H, 6.43; N, 4.33.

When ranges are used herein for physical properties, such as molecular weight, or chemical properties, such as chemical formulae, all combinations and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of Formula I:

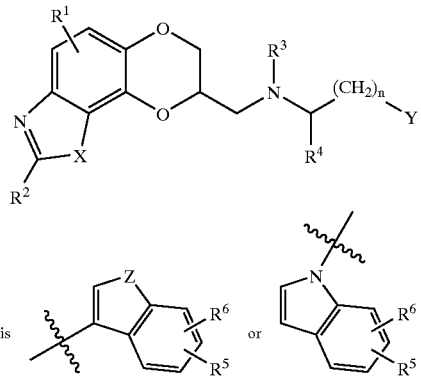

wherein Y is 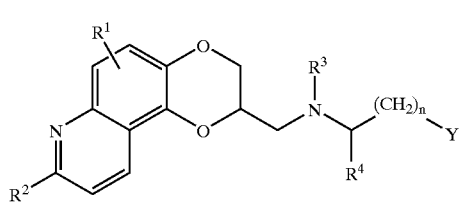

X is O, N=CH, CR$^7$=CH or CR$^7$=N, in which R$^7$ is hydrogen or alkyl of 1 to 6 carbon atoms;

Z is O, S or NR$^8$, in which R$^8$ is hydrogen or alkyl of 1 to 6 carbon atoms;

R$^1$, R$^5$ and R$^6$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyl of 2 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, alkanesulfonyl of 1 to 6 carbon atoms or alkanesulfonamido of 1 to 6 carbon atoms;

R$^2$ is hydrogen, halo, amino, mono- or di-alkylamino in which each alkyl group has 1 to 6 carbon atoms or alkyl of 1 to 6 carbon atoms;

R$^3$ and R$^4$ are, independently, hydrogen or alkyl of 1 to 6 carbon atoms;

n is 1, 2 or 3;

or a pharmaceutically acceptable salt thereof.

2. A compound according to claim 1, wherein X is CR$^7$=CH where R$^7$ is hydrogen or alkyl of 1 to 3 carbon atoms.

3. A compound according to claim 1 of Formula Ia:

Ia or a pharmaceutically acceptable salt thereof.

4. A compound according to claim 1 of Formula Ib:

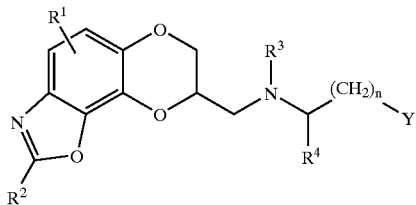

or a pharmaceutically acceptable salt thereof.

5. A compound according to claim 1, wherein $R^1$ is hydrogen, halo, cyano, trifluoromethyl, alkyl of 1 to 6 carbon atoms or alkoxy of 1 to 6 carbon atoms.

6. A compound according to claim 1, wherein $R^1$ is hydrogen, halo or alkoxy of 1 to 6 carbon atoms.

7. A compound according to claim 1, wherein $R^1$ is hydrogen.

8. A compound according to claim 1, wherein $R^2$ is hydrogen, amino or alkyl of 1 to 6 carbon atoms.

9. A compound according to claim 1, wherein $R^2$ is hydrogen or alkyl of 1 to 3 carbon atoms.

10. A compound according to claim 1, wherein $R^3$ and $R^4$ are independently selected from hydrogen or alkyl of 1 to 3 carbon atoms.

11. A compound according to claim 1, wherein $R^4$ is hydrogen.

12. A compound according to claim 1, wherein $R^7$ and $R^8$ are independently selected from hydrogen or alkyl of 1 to 3 carbon atoms.

13. A compound according to claim 1, wherein $R^5$ and $R^6$ are independently selected from hydrogen, hydroxy, halo, cyano, carboxamido, alkyl of 1 to 6 carbon atoms, or alkoxy of 1 to 6 carbon atoms.

14. A compound according to claim 1, wherein $R^5$ and $R^6$ are independently selected from hydrogen, cyano or halogen.

15. A compound according to claim 1, wherein Z is $NR^8$.

16. A compound according to claim 15, wherein $R^8$ is hydrogen or alkyl of 1 to 3 carbon atoms.

17. A compound according to claim 1, wherein n is 2 or 3.

18. A compound according to claim 1, wherein $R^1$ hydrogen, halo, cyano, trifluoromethyl, alkyl of 1 to 6 carbon atoms or alkoxy of 1 to 6 carbon atoms.

19. A compound according to claim 1, wherein $R^1$ is hydrogen, halo or alkoxy of 1 to 6 carbon atoms, $R^2$, $R^3$, $R^7$ and $R^8$ are hydrogen or alkyl of 1 to 3 carbon atoms, $R^4$ is hydrogen, $R^5$ and $R^6$ are independently hydrogen, cyano or halogen, Z is $NR^8$ and n is 2 or 3.

20. A compound according to claim 1, wherein said compound is N-[2-(5-methoxy-1H-indol-3-yl)-ethyl]-N-(8-methyl-2,3-dihydro-[1,4]dioxino[2,3-f]quinolin-2-ylmethyl)-amine or a pharmaceutically acceptable salt thereof.

21. A compound according to claim 1, wherein said compound is N-[2-(5-chloro-1H-indol-3-yl)ethyl]-N-(8-methyl-2,3-dihydro-[1,4]dioxino[2,3-f]quinolin-2-ylmethyl)amine or a pharmaceutically acceptable salt thereof.

22. A compound according to claim 1, wherein said compound is N-[3-(5-fluoro-1H-indol-3-yl)propyl]-N-(8-methyl-2,3-dihydro-[1,4]dioxino[2,3-f]quinolin-2-ylmethyl)amine or a pharmaceutically acceptable salt thereof.

23. A compound according to claim 1, wherein said compound is N-[2-(5-fluoro-1H-indol-3-yl)ethyl]-N-(8-methyl-2,3-dihydro-[1,4]dioxino[2,3-f]quinolin-2-ylmethyl)amine or a pharmaceutically acceptable salt thereof.

24. A compound according to claim 1, wherein said compound is N-[3-(5-fluoro-1H-indol-3-yl)propyl]-N-(8-ethyl-2,3-dihydro-[1,4]dioxino[2,3-f]quinolin-2-ylmethyl)amine or a pharmaceutically acceptable salt thereof.

25. A compound according to claim 1, wherein said compound is N-[3-(1H-indol-3-yl)propyl]-N-(8-methyl-2,3-dihydro-[1,4]dioxino[2,3-f]quinolin-2-ylmethyl)amine or a pharmaceutically acceptable salt thereof.

26. A compound according to claim 1, wherein said compound is N-[3-(5-fluoro-1H-indol-3-yl)propyl]-N-methyl-N-(8-methyl-2,3-dihydro-[1,4]dioxino[2,3-f]quinolin-2-ylmethyl)amine or a pharmaceutically acceptable salt thereof.

27. A compound according to claim 1, wherein said compound is N-[3-(7-fluoro-1H-indol-3-yl)propyl]-N-(8-methyl-2,3-dihydro-[1,4]dioxino[2,3-f]quinolin-2-ylmethyl)amine or a pharmaceutically acceptable salt thereof.

28. A compound according to claim 1, wherein said compound is N-[4-(1H-indol-3-yl)butyl]-N-(8-methyl-2,3-dihydro-[1,4]dioxino[2,3-f]quinolin-2-ylmethyl)amine or a pharmaceutically acceptable salt thereof.

29. A compound according to claim 1, wherein said compound is N-[4-(5-fluoro-1H-indol-3-yl)butyl]-N-(8-methyl-2,3-dihydro-[1,4]dioxino[2,3-f]quinolin-2-ylmethyl)amine or a pharmaceutically acceptable salt thereof.

30. A compound according to claim 1, wherein said compound is N-[4-(5-fluoro-1H-indol-3-yl)-N-(8-methyl-2,3-dihydro-[1,4]dioxino[2,3-f]quinolin-2-ylmethyl)butan-2-amine or a pharmaceutically acceptable salt thereof.

31. A compound according to claim 1, wherein said compound is N-[3-(5-fluoro-1-methyl-1H-indol-3-yl)propyl]-N-(8-methyl-2,3-dihydro-[1,4]dioxino[2,3-f]quinolin-2-ylmethyl)amine or a pharmaceutically acceptable salt thereof.

32. A compound according to claim 1, wherein said compound is N-[3-(5,7-difluoro-1H-indol-3-yl)propyl]-N-(8-methyl-2,3-dihydro-[1,4]dioxino[2,3-f]quinolin-2-ylmethyl)amine or a pharmaceutically acceptable salt thereof.

33. A compound according to claim 1, wherein said compound is N-(2,3-dihydro-[1,4]dioxino[2,3-f]quinolin-2-ylmethyl)-N-[3-(5-fluoro-1H-indol-3-yl)propyl]amine or a pharmaceutically acceptable salt thereof.

34. A compound according to claim 1, wherein said compound is N-(2,3-dihydro-[1,4]dioxino[2,3-f]quinolin-2-ylmethyl)-N-[3-(5-fluoro-1H-indol-3-yl)propyl]-N-methylamine or a pharmaceutically acceptable salt thereof.

35. A compound according to claim 1, wherein said compound is N-[3-(5,7-difluoro-1H-indol-3-yl)propyl]-N-methyl-N-(8-methyl-2,3-dihydro-[1,4]dioxino[2,3-f]quinolin-2-ylmethyl)amine or a pharmaceutically acceptable salt thereof.

36. A compound according to claim 1, wherein said compound is N-[2-(1-benzofuran-3-yl)ethyl]-N-(8-methyl-2,3-dihydro-[1,4]dioxino[2,3-f]quinolin-2-ylmethyl)amine or a pharmaceutically acceptable salt thereof.

37. A compound according to claim 1, wherein said compound is N-[3-(1-benzofuran-3-yl)propyl]-N-(8-methyl-2,3-dihydro-[1,4]dioxino[2,3-f]quinolin-2-ylmethyl)amine or a pharmaceutically acceptable salt thereof.

38. A compound according to claim 1, wherein said compound is N-[3-(7-methoxy-1-benzofuran-3-yl)propyl]-

N-(8-methyl-2,3-dihydro-[1,4]dioxino[2,3-f]quinolin-2-ylmethyl)amine or a pharmaceutically acceptable salt thereof.

39. A compound according to claim 1, wherein said compound is N-[3-(1-benzothien-3-yl)propyl]-N-(8-methyl-2,3-dihydro-[1,4]dioxino[2,3-f]quinolin-2-ylmethyl)amine or a pharmaceutically acceptable salt thereof.

40. A compound according to claim 1, wherein said compound is N-[2-(1-benzothien-3-yl)ethyl]-N-(8-methyl-2,3-dihydro-[1,4]dioxino[2,3-f]quinolin-2-ylmethyl)amine or a pharmaceutically acceptable salt thereof.

41. A compound according to claim 1, wherein said compound is N-[3-(1-benzothien-3-yl)propyl]-N-methyl-N-(8-methyl-2,3-dihydro-[1,4]dioxino[2,3-f]quinolin-2-ylmethyl)amine or a pharmaceutically acceptable salt thereof.

42. A compound according to claim 1, wherein said compound is N-[3-(5-fluoro-1H-indol-3-yl)propyl]-N-(2-methyl-7,8-dihydro-[1,4]dioxino[2,3-g][1,3]benzoxazol-8-ylmethyl)amine or a pharmaceutically acceptable salt thereof.

43. A compound according to claim 1, wherein said compound is N-[3-(5-fluoro-1H-indol-3-yl)propyl]-N-methyl-N-(2-methyl-7,8-dihydro-[1,4]dioxino[2,3-g][1,3]benzoxazol-8-ylmethyl)amine or a pharmaceutically acceptable salt thereof.

44. A compound according to claim 1, wherein said compound is N-ethyl-N-[3-(5-Fluoro-1H-indol-3-yl)propyl]-N-(8-methyl-2,3-dihydro-[1,4]dioxino[2,3-f]quinolin-2-ylmethyl)amine or a pharmaceutically acceptable salt thereof.

45. A compound according to claim 1, wherein said compound is N-[3-(5,7-difluoro-1-methyl-1H-indol-3-yl)propyl]-N-(8-methyl-2,3-dihydro-[1,4]dioxino[2,3-f]quinolin-2-ylmethyl)amine or a pharmaceutically acceptable salt thereof.

46. A compound according to claim 1, wherein said compound is N-[3-(5,7-difluoro-1-methyl-1H-indol-3-yl)propyl]-N-methyl-N-(8-methyl-2,3-dihydro-[1,4]dioxino[2,3-f]quinolin-2-ylmethyl)amine or a pharmaceutically acceptable salt thereof.

47. A compound according to claim 1, wherein said compound is N-[4-(1-benzofuran-3-yl)butyl]-N-(8-methyl-2,3-dihydro-[1,4]dioxino[2,3-f]quinolin-2-ylmethyl)amine or a pharmaceutically acceptable salt thereof.

48. A compound according to claim 1, wherein said compound is 3-{3-[(8-methyl-2,3-dihydro-[1,4]dioxino[2,3-f]quinolin-2-ylmethyl)-amino]-propyl}-1H-indole5-carbonitrile or a pharmaceutically acceptable salt thereof.

49. A compound according to claim 1, wherein said compound is 3-{3-[(2-methyl-7,8-dihydro-[1,4]dioxino[2,3-g][1,3]benzoxazol-8-ylmethyl)amino]-propyl}-1H-indole-5-carbonitrile or a pharmaceutically acceptable salt thereof.

50. A compound according to claim 1, wherein said compound is 3-{3-[methyl-(2-methyl-7,8-dihydro-[1,4]dioxino[2,3-g][1,3]benzoxazol-8-ylmethyl)-amino]-propyl}-1H-indole-5-carbonitrile or a pharmaceutically acceptable salt thereof.

51. A compound according to claim 1, wherein said compound is 3-{3-[methyl-(8-methyl-2,3-dihydro-[1,4]dioxino[2,3-f]quinolin-2-ylmethyl)-amino]-propyl}-1H-indole-5-carbonitrile or a pharmaceutically acceptable salt thereof.

52. A compound according to claim 1, wherein said compound is [3-(6-fluoro-indol-1-yl)-propyl]-(8-methyl-2,3-dihydro-[1,4]dioxino[2,3-f]quinolin-2-ylmethyl)-amine or a pharmaceutically acceptable salt thereof.

53. A compound according to claim 1, wherein said compound is [3-(6-fluoro-indol-1-yl)-propyl]-methyl-(8-methyl-2,3-dihydro-[1,4]dioxino[2,3-f]quinolin-2-ylmethyl)-amine or a pharmaceutically acceptable salt thereof.

54. A compound according to claim 1, wherein said compound is [4-(5-fluoro-1-methyl-1H-indol-3-yl)-butyl]-(8-methyl-2,3-dihydro-[1,4]dioxino[2,3-f]quinolin-2-ylmethyl)-amine or a pharmaceutically acceptable salt thereof.

55. A compound according to claim 1, wherein said compound is ethyl-[3-(5-fluoro-1H-indol-3-yl)-propyl]-(2-methyl-7,8-dihydro-[1,4]dioxino[2,3-g][1,3]benzoxazol-8-ylmethyl)-amine or a pharmaceutically acceptable salt thereof.

56. A compound according to claim 1, wherein said compound is 1-methyl-3-(3-[(8-methyl-2,3-dihydro-[1,4]dioxino[2,3-f]quinolin-2-ylmethyl)-amino]-propyl)-1H-indole-5-carbonitrile or a pharmaceutically acceptable salt thereof.

57. A compound according to claim 1, wherein said compound is [4-(6-fluoro-indol-1-yl)-butyl]-(8-methyl-2,3-dihydro-[1,4]dioxino[2,3-f]quinolin-2-ylmethyl)-amine or a pharmaceutically acceptable salt thereof.

58. A compound according to claim 1, wherein said compound is 3-{4-[(8-methyl-2,3-dihydro-[1,4]dioxino[2,3-f]quinolin-2-ylmethyl)-amino]-butyl}-1H-indole-5-carbonitrile or a pharmaceutically acceptable salt thereof.

59. A compound according to claim 1, wherein said compound is 1-methyl-3-{3-[methyl-(8-methyl-2,3-dihydro-[1,4]dioxino[2,3-f]quinolin-2-ylmethyl)-amino]-propyl}-1H-indole-5-carbonitrile or a pharmaceutically acceptable salt thereof.

60. A compound according to claim 1, wherein said compound is 3-{4-[-methyl-(8-methyl-2,3-dihydro-[1,4]dioxino[2,3-f]quinolin-2-ylmethyl)-amino]-butyl}-1H-indole-5-carbonitrile or a pharmaceutically acceptable salt thereof.

61. A compound according to claim 1, wherein said compound is [3-(5-fluoro-1-methyl-1H-indol-3-yl)-propyl]-methyl-(8-methyl-2,3-dihydro-[1,4]dioxino[2,3-f]quinolin-2-ylmethyl)-amine or a pharmaceutically acceptable salt thereof.

62. A compound according to claim 1, wherein said compound is [4-(5-fluoro-1H-indol-3-yl)-butyl]-methyl-(8-methyl-2,3-dihydro-[1,4]dioxino[2,3-f]quinolin-2-ylmethyl)-amine or a pharmaceutically acceptable salt thereof.

63. A compound according to claim 1, wherein said compound is [4-(5-fluoro-1-methyl-1H-indol-3-yl)-butyl]-methyl-(8-methyl-2,3-dihydro-[1,4]dioxino[2,3-f]quinolin-2-ylmethyl)-amine or a pharmaceutically acceptable salt thereof.

64. A compound according to claim 1, wherein said compound is [3-(5-fluoro-1H-indol-3-yl)-propyl]-(8-methyl-2,3-dihydro-[1,4]dioxino[2,3-f]quinolin-2-ylmethyl)-propyl-amine or a pharmaceutically acceptable salt thereof.

65. A compound according to claim 1, wherein said compound is [3-(4-fluoro-indol-1-yl)-propyl]-(8-methyl-2,3-dihydro-[1,4]dioxino[2,3-f]quinolin-2-ylmethyl)-amine or a pharmaceutically acceptable salt thereof.

66. A compound according to claim 1, wherein said compound is [4-(6-fluoro-indol-1-yl)-butyl]-methyl-(8-methyl-2,3-dihydro-[1,4]dioxino[2,3-f]quinolin-2-ylmethyl)-amine or a pharmaceutically acceptable salt thereof.

67. A compound according to claim 1, wherein said compound is [3-(4-fluoro-indol-1-yl)-propyl]-methyl-(8-methyl-2,3-dihydro-[1,4]dioxino[2,3-f]quinolin-2-ylmethyl)-amine or a pharmaceutically acceptable salt thereof.

68. A compound according to claim 1, wherein said compound is N-[4[(5-Chloro-1-benzothien-3-yl)butyl]-N-{[(2S)-8-methyl-2,3-dihydro[1,4]dioxino[2,3-f]quinolin-2-yl]methyl}amine or a pharmaceutically acceptable salt thereof.

69. A compound according to claim 1, wherein said compound is N-[3-(5-Chloro-1-benzothien-3-yl)propyl]-N-{[(2S)-8-methyl-2,3-dihydro[1,4]dioxino[2,3-f]quinolin-2-yl]methyl}amine or a pharmaceutically acceptable salt thereof.

70. A compound according to claim 1, wherein said compound is N-[3-(5-Fluoro-1-benzothien-3-yl)propyl]-N-{[(2S)-8-methyl-2,3-dihydro[1,4]dioxino[2,3-f]quinolin-2-yl]methyl}amine or a pharmaceutically acceptable salt thereof.

71. A compound according to claim 1, wherein said compound is N-[4-(1-Benzofuran-3-yl)butyl]-N-ethyl-N-{[(2S)-8-methyl-2,3-dihydro[1,4]dioxino[2,3-f]quinolin-2-yl]methyl}amine or a pharmaceutically acceptable salt thereof.

72. A compound according to claim 1, wherein said compound is the S enantiomer, substantially free of the R enantiomer of said compound.

73. A method of treating a subject suffering from a condition selected from depression, anxiety, panic disorder, post-traumatic stress disorder, premenstrual dysphoric disorder, attention deficit disorder, obsessive compulsive disorder, social anxiety disorder, generalized anxiety disorder, obesity, eating disorders, vasomotor flushing, cocaine and alcohol addiction, and sexual dysfunction, comprising the step of:

administering to said subject suffering from said condition, a therapeutically effective amount of a compound according to claim 1 or a pharmaceutically acceptable salt thereof.

74. A method according to claim 73, wherein the condition is depression.

75. A method according to claim 73, wherein the condition is selected from the group consisting of obsessive-compulsive disorder, panic attacks, generalized anxiety disorder, and social anxiety disorder.

76. A pharmaceutical composition, comprising:

an effective amount of a compound according to claim 1 or a pharmaceutically acceptable salt thereof; and a pharmaceutically acceptable carrier or excipient.

* * * * *